United States Patent
Brodney et al.

(10) Patent No.: US 7,479,559 B2
(45) Date of Patent: Jan. 20, 2009

(54) BENZYL(IDENE)-LACTAM DERIVATIVES

(75) Inventors: Michael Aaron Brodney, East Lyme, CT (US); Stephane Caron, Stonington, CT (US); Christopher John Helal, East Lyme, CT (US); Jeffrey W. Raggon, North Stonington, CT (US); Yong Tao, Salem, CT (US); Nga M. Do, Groton, CT (US)

(73) Assignee: Pfizer Inc., New York, NY (US)

( * ) Notice: Subject to any disclaimer, the term of this patent is extended or adjusted under 35 U.S.C. 154(b) by 340 days.

(21) Appl. No.: 11/083,188

(22) Filed: Mar. 17, 2005

(65) Prior Publication Data
US 2005/0245521 A1 Nov. 3, 2005

Related U.S. Application Data

(60) Provisional application No. 60/553,808, filed on Mar. 17, 2004.

(51) Int. Cl.
C07D 295/155 (2006.01)
C07D 401/04 (2006.01)
C07D 403/04 (2006.01)
C07D 405/10 (2006.01)
C07D 413/10 (2006.01)
C07D 403/10 (2006.01)

(52) U.S. Cl. .................. 544/121; 540/470; 540/575; 544/364; 544/372; 544/374; 546/194; 546/208; 546/278.4

(58) Field of Classification Search .............. None
See application file for complete search history.

(56) References Cited

U.S. PATENT DOCUMENTS

| 6,656,937 B2 | 12/2003 | Germann et al. |
| 2003/0064987 A1 | 4/2003 | Germann et al. |
| 2004/0048859 A1 | 3/2004 | Germann et al. |

FOREIGN PATENT DOCUMENTS

| WO | WO 9400440 | 1/1994 |
| WO | WO 9421619 | 9/1994 |
| WO | WO 9531988 | 11/1995 |
| WO | WO 9600720 | 1/1996 |
| WO | WO 9736867 | 10/1997 |
| WO | WO 9814433 | 4/1998 |
| WO | WO0153261 A1 | 7/2001 |

OTHER PUBLICATIONS

R. A. Glennon; Serotonin Receptors: Clinical Implications; Neuroscience & Biobehavioral Reviews; vol. 14, pp. 35-47 (1990).
G. Maura, et al.; Serotonin 5-HT1D and 5-HT1A Receptors Respectively Mediate Inhibition of Glutamate Release and Inhibition of Cyclic GMP Production in Rat Cerebellum in Vitro; J. of Neurochemistry; vol. 66, No. 1, pp. 203-209 (1996).
R. A. Glennon, et al.; 5-HT1D Serotonin Receptors: Results of a Structure-Affinity Investigation; Drug Development Research; vol. 22, pp. 22-25 (1991).

*Primary Examiner*—Emily Bernhardt
(74) *Attorney, Agent, or Firm*—Gregg C. Benson; Martha G. Munchhof

(57) ABSTRACT

The present invention relates to novel benzyl(idene)-lactam derivatives, compounds of the formula I

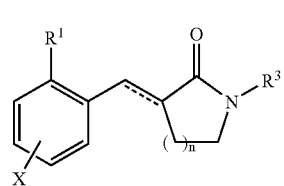

wherein $R^1$ is a group of the formula $G^1$ or $G^2$ depicted below,

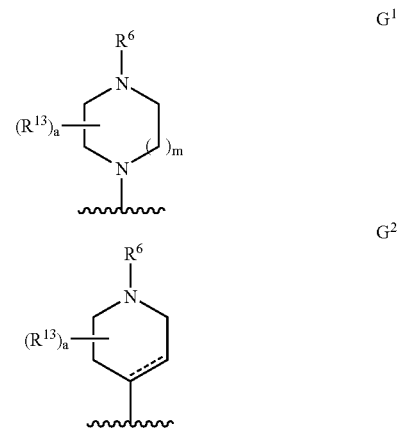

wherein $R^1$, $R^3$, $R^6$, $R^{13}$ X, a, n and m are as defined herein, their pharmaceutically acceptable salts, and pharmaceutical compositions which include selective antagonists, inverse agonists and partial agonists of serotonin 1 (5-HT$_1$) receptors, specifically, of one or both of the 5-HT$_{1A}$ and 5-HT$_{1B}$ receptors. The compounds of the invention are useful in treating or preventing depression, anxiety, obsessive compulsive disorder (OCD) and other disorders for which a 5-HT$_1$ agonist or antagonist is indicated and have reduced potential for cardiac side effects, in particular QTc prolongation.

52 Claims, No Drawings

BENZYL(IDENE)-LACTAM DERIVATIVES

The entire disclosure of parent application 60/553,808 filed Mar. 17, 2004 is fully incorporated herein by reference thereto.

BACKGROUND OF THE INVENTION

The present invention relates to novel benzyl(idene)-lactam derivatives, to intermediates for their preparation, to pharmaceutical compositions containing them and to their medicinal use. The compounds of the present invention include selective antagonists, inverse agonists and partial agonists of serotonin 1 (5-$HT_1$) receptors, specifically, of one or both of the 5-$HT_{1A}$ and 5-$HT_{1B}$ (formerly classified 5-$HT_{1D}$) receptors. They are useful in treating or preventing depression, anxiety, obsessive compulsive disorder (OCD) and other disorders for which a 5-$HT_1$ agonist or antagonist is indicated and have reduced potential for cardiac side effects, in particular QTc prolongation.

European Patent Publication 434,561, published on Jun. 26, 1991, refers to 7-alkyl alkoxy, and hydroxy substituted-1-(4-substituted-1-piperazinyl)-naphthalenes. The compounds are referred to as 5-$HT_1$ agonists and antagonists useful for the treatment of migraine, depression, anxiety, schizophrenia, stress and pain.

European Patent Publication 343,050, published on Nov. 23, 1989, refers to 7-unsubstituted, halogenated, and methoxy substituted-1-(4-substituted-1-piperazinyl)-naphthalenes as useful 5-$HT_{1A}$ ligand therapeutics.

PCT publication WO 94/21619, published Sep. 29, 1994, refers to naphthalene derivatives as 5-$HT_1$ agonists and antagonists.

PCT publication WO 96/00720, published Jan. 11, 1996, refers to naphthyl ethers as useful 5-$HT_1$ agonists and antagonists.

PCT publication WO 97/36867, published Oct. 9, 1997, and WO 98/14433, published Apr. 9, 1998, refer to related benzyl(idene)-lactam derivatives having utility as psychotherapeutic agents.

European Patent Publication 701,819, published Mar. 20, 1996, refers to the use of 5-$HT_1$ agonists and antagonists in combination with a 5-HT re-uptake inhibitor.

Glennon et al. refers to 7-methoxy-1-(1-piperazinyl)-naphthalene as a useful 5-$HT_1$ ligand in their article "5-$HT_{1D}$ Serotonin Receptors", Clinical Drug Res. Dev., 22, 25-36 (1991).

Glennon's article "Serotonin Receptors: Clinical Implications", Neuroscience and Behavioral Reviews, 14, 35-47 (1990), refers to the pharmacological effects associated with serotonin receptors including appetite suppression, thermoregulation, cardiovascular/hypotensive effects, sleep, psychosis, anxiety, depression, nausea, emesis, Alzheimer's disease, Parkinson's disease and Huntington's disease.

PCT publication WO 95/31988, published Nov. 30, 1995, refers to the use of a 5-$HT_{1D}$ antagonist in combination with a 5-$HT_{1A}$ antagonist to treat CNS disorders such as depression, generalized anxiety, panic disorder, agoraphobia, social phobias, obsessive-compulsive disorder, post-traumatic stress disorder, memory disorders, anorexia nervosa and bulimia nervosa, Parkinson's disease, tardive dyskinesias, endocrine disorders such as hyperprolactinaemia, vasospasm (particularly in the cerebral vasculature) and hypertension, disorders of the gastrointestinal tract where changes in motility and secretion are involved, as well as sexual dysfunction.

G. Maura et al., J. Neurochem, 66 (1), 203-209 (1996), have stated that administration of agonists selective for 5-$HT_{1A}$ receptors or for both 5-$HT_{1A}$ and 5-$HT_{1D}$ receptors might represent a great improvement in the treatment of human cerebellar ataxias, a multifaceted syndrome for which no established therapy is available.

European Patent Publication 666,261, published Aug. 9, 1995 refers to thiazine and thiomorpholine derivatives which are claimed to be useful for the treatment of cataracts.

SUMMARY OF THE INVENTION

The present invention relates to benzyl(idene)-lactams of the formula I

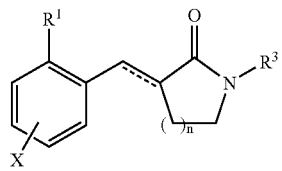

wherein $R^1$ is a group of the formula $G^1$ or $G^2$ depicted below,

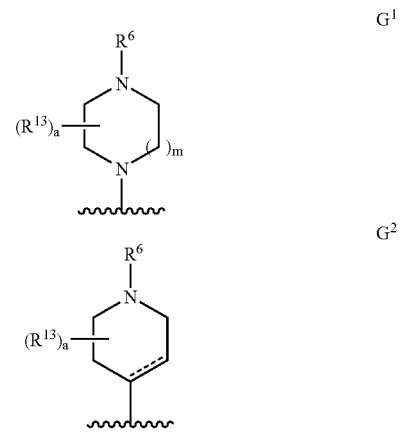

a is zero to eight;

m is one to three;

$R^6$ is selected from the group consisting of hydrogen, ($C_1$-$C_6$)alkyl optionally substituted with ($C_1$-$C_6$)alkoxy or one to three fluorine atoms, or (($C_1$-$C_4$)alkyl)aryl wherein the aryl moiety is phenyl, naphthyl, or heteroaryl-($CH_2$)$_q$—, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chloro, fluoro, bromo, iodo, ($C_1$-$C_6$)alkyl, ($C_1$-$C_6$)alkoxy, trifluoromethyl, cyano and —$SO_t$($C_1$-$C_6$)alkyl, wherein t is zero, one or two;

each $R^{13}$ is, independently, ($C_1$-$C_4$)alkyl or a ($C_1$-$C_4$)alkylene bridge from one of the ring carbons of the piperazine or piperidine ring of $G^1$ or $G^2$, respectively, to the same or another ring carbon or a ring nitrogen of the piperazine or piperidine ring of $G^1$ or $G^2$, respectively, having an available bonding site, or to a ring carbon of $R^6$, when $R^6$ has a ring structure having an available bonding site;

X is hydrogen, chloro, fluoro, bromo, iodo, cyano, $(C_1-C_6)$ alkyl, hydroxy, $(C_1-C_6)$alkoxy, $—SO_t(C_1-C_6)$alkyl wherein t is zero, one or two, $—CO_2R^{10}$ or $—CONR^{11}R^{12}$;

each of $R^{10}$, $R^{11}$ and $R^{12}$ is selected, independently, from hydrogen, $(C_1-C_4)$alkyl, phenyl and naphthyl, wherein said phenyl or naphthyl may optionally be substituted with one or more substituents independently selected from chloro, fluoro, bromo, iodo, $(C_1-C_6)$alkyl, $(C_1-C_6)$ alkoxy, trifluoromethyl, cyano and $—SO_t(C_1-C_6)$alkyl wherein t is zero, one or two; or $R^{11}$ and $R^{12}$, together with the nitrogen to which they are attached, form a 5- to 7-membered heteroalkyl ring that may contain from zero to four heteroatoms selected from nitrogen, sulfur and oxygen;

$R^3$ is vinyl, C(=O)R, wherein R is $C_1-C_8$ straight chain or branched alkyl, $C_3-C_8$ cycloalkyl, or aryl, wherein R is preferably tert-butyl, or, $R^3$ is $—(CH_2)_gB$, wherein g is zero to three and B is hydrogen, phenyl, naphthyl or a 5- to 6-membered heteroaryl ring containing from one to four heteroatoms in the ring selected from oxygen, nitrogen and sulfur, with the proviso that said ring cannot contain two adjacent oxygen atoms or two adjacent sulfur atoms and wherein each of the foregoing phenyl, naphthyl and heteroaryl rings may optionally be substituted with one to three substituents independently selected from $(C_1-C_8)$hydroxyalkyl-, $(C_1-C_8)$alkoxy-$(C_1-C_8)$alkyl-, $(C_3-C_8)$hydroxycycloalkyl-, $(C_3-C_8)$cycloalkoxy-, $(C_1-C_8)$alkoxy-$(C_3-C_8)$ cycloalkyl-, heterocycloalkyl, hydroxyheterocycloalkyl, and $(C_1-C_8)$alkoxy-heterocycloalkyl, wherein each $(C_3-C_8)$cycloalkyl or heterocycloalkyl moiety may be independently substituted with from one to three $(C_1-C_6)$alkyl or benzyl groups;

When B is a phenyl, naphthyl or heteroaryl ring, each said ring may be optionally substituted with one to three substituents independently selected from phenyl, naphthyl and a 5- to 6-membered heteroaryl ring containing from one to four heteroatoms selected from oxygen, nitrogen and sulfur, with the proviso that said heteroaryl ring cannot contain two adjacent oxygen atoms or two adjacent sulfur atoms, and wherein each independently selected phenyl, naphthyl or heteroaryl substituent may itself be substituted with from one to three $(C_1-C_8)$alkyl or $C_3-C_8$ cycloalkyl substituents, wherein examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl; or, When B is a phenyl, naphthyl or heteroaryl ring, each said ring may be optionally substituted with one to three substituents independently selected from (a) lactone formed from $—(CH_2)_tOH$ with an ortho $—COOH$, wherein t is one, two or three; (b) $—CONR^{14}R^{15}$, wherein $R^{14}$ and $R^{15}$ are independently selected from $(C_1-C_8)$alkyl and benzyl, or $R^{14}$ and $R^{15}$ together with the nitrogen to which they are attached form a 5- to 7-membered heteroalkyl ring that may contain from zero to three heteroatoms selected from nitrogen, sulfur and oxygen in addition to the nitrogen of the $—CONR^{14}R^{15}$ group, wherein when any of said heteroatoms is nitrogen it may be optionally substituted with $(C_1-C_8)$alkyl or benzyl, with the proviso that said ring cannot contain two adjacent oxygen atoms or two adjacent sulfur atoms; (c) $—(CH_2)_vNCOR^{16}R^{17}$ wherein v is zero, one, two or three and $—COR^{16}$ and $R^{17}$ taken together with the nitrogen to which they are attached form a 4- to 6-membered lactam ring; and, (d) $—(C1-C8)NR^{18}R^{19}$ where each of $R^{18}$ and $R^{19}$ is selected, independently, from hydrogen and $(C_1-C_4)$ alkyl, or $R^{18}$ and $R^{19}$, together with the nitrogen to which they are attached, form a 4- to 7-membered heteroalkyl ring that may contain from zero to four heteroatoms selected from nitrogen, sulfur and oxygen;

Wherein the broken lines indicate optional double bonds; and, n is one, two, or three; or, a pharmaceutically acceptable salt or optical isomer thereof.

Other embodiments of the invention relate to a compound according to formula I wherein $R^3$ is $(CH_2)_gB$ wherein g is Zero and B is selected from phenyl or pyridyl.

The invention also relates to a compound according to formula I wherein $R^3$ is $(CH_2)_gB$ wherein g is zero and B is selected from phenyl, or pyridyl, wherein said $(C_3-C_8)$cycloalkyl moiety of said $(C_3-C_8)$hydroxycycloalkyl-, $(C_1-C_8)$ alkoxy-$(C_3-C_8)$cycloalkyl-, substituents is selected from cyclopropyl, cyclobutyl, cyclopentyl or cyclohexyl.

The invention also relates to a compound according to formula I wherein $R^3$ is $(CH_2)_gB$ wherein g is zero and B is selected from phenyl, or pyridyl, wherein said heterocycloalkyl moiety having 4 to 8 atoms, of said 1 to 3 optional substituents, is selected from tetrahydropyranyl, morpholinyl, azetidinyl, pyrrolidinyl, piperidyl, piperazinyl, thiomorpholinyl, azepinyl, diazepinyl, oxazepinyl, thiazepinyl, oxetanyl, and tetrahydrofuranyl.

This invention also relates to a compound according to formula I wherein $R^3$ is $(CH_2)_gB$ wherein g is zero and B is selected from phenyl or pyridyl, wherein said alkoxyheterocycloalkyl moiety is selected from tetrahydropyranoxy, tetrahydrofuranoxy, oxetanoxy, azetidinoxy, pyrrolidinoxy, and piperidinoxy.

The invention also relates to a compound according to formula I wherein $R^3$ is $(CH_2)_gB$ wherein g is zero and B is selected from phenyl, or pyridyl, wherein said 5- to 6-membered heteroaryl ring, of said 1 to 3 optional substituents, is selected from pyridyl, pyrrolyl, pyrazolyl, imidazolyl, triazolyl, tetrazolyl, oxazolyl, oxadiazolyl, isoxazolyl, thiazolyl, isothiazolyl, oxadiazolyl, thiadiazolyl, pyrimidinyl, pyrazinyl, and pyridazinyl.

The invention also relates to a compound according to formula I wherein $R^3$ is $(CH_2)_gB$ wherein g is zero and B is selected from phenyl or pyridyl, wherein said $R^{14}$ and said $R^{15}$ groups of said $—CONR^{14}R^{15}$ substituent together with the nitrogen to which they are attached form a 5- to 6-membered heteroalkyl ring selected from piperidine, N—$(C_0-C_6)$ alkylpiperazine and morpholine.

The invention also relates to a compound according to formula I wherein $R^3$ is $(CH_2)_gB$ wherein g is zero and B is selected from phenyl or pyridyl, wherein said $—COR^{16}$ and $R^{17}$ groups of said $—(CH_2)_vNCOR^{16}R^{17}$ substituent together with the nitrogen to which they are attached form a 5- or 6-membered lactam ring, and v is 1.

The invention also relates to a compound according to formula I wherein $R^3$ is $(CH_2)_g B$ wherein g is zero and B is selected from phenyl or pyridyl, wherein a lactone is formed from said —CH$_2$OH substituent, with said ortho —COOH substituent.

Specific examples of the compounds of the present invention are as follows:

3-[5-Fluoro-2-(4-methyl-piperazin-1-yl)-benzyl]-1-[4-(1-hydroxy-1-methyl-ethyl)-phenyl]-pyrrolidin-2-one,
4-{3-[2-(4-Methyl-piperazin-1-yl)-benzyl]-2-oxo-pyrrolidin-1-yl}-benzoic acid ethyl ester,
3-[2-(4-Methyl-piperazin-1-yl)-benzyl]-1-(6-morpholin-4-yl-pyridin-3-yl)-pyrrolidin-2-one,
1-[4-(1-Hydroxy-1-methyl-ethyl)-phenyl]-3-[2-(4-methyl-piperazin-1-yl)-benzyl]-pyrrolidin-2-one,
3-[2-(4-Methyl-piperazin-1-yl)-benzyl]-1-(4-morpholin-4-yl-phenyl)-pyrrolidin-2-one,
1-[4-(1-Hydroxy-cyclopentyl)-phenyl]-3-[2-(4-methyl-piperazin-1-yl)-benzyl]-pyrrolidin-2-one,
1-[4-(1-Hydroxy-cyclohexyl)-phenyl]-3-[2-(4-methyl-piperazin-1-yl)-benzyl]-pyrrolidin-2-one,
1-[4-(1-Ethyl-1-hydroxy-propyl)-phenyl]-3-[2-(4-methyl-piperazin-1-yl)-benzyl]-pyrrolidin-2-one,
1-[3-(1-Hydroxy-1-methyl-ethyl)-phenyl]-3-[2-(4-methyl-piperazin-1-yl)-benzyl]-pyrrolidin-2-one,
1-[4-(2-Hydroxy-2-methyl-propyl)-phenyl]-3-[2-(4-methyl-piperazin-1-yl)-benzyl]-pyrrolidin-2-one,
1-[6-(1-Hydroxy-1-methyl-ethyl)-pyridin-3-yl]-3-[2-(4-methyl-piperazin-1-yl)-benzyl]-pyrrolidin-2-one,
1-[4-(1-Methoxy-1-methyl-ethyl)-phenyl]-3-[2-(4-methyl-piperazin-1-yl)-benzyl]-pyrrolidin-2-one,
1-[4-(2-Methoxy-2-methyl-propyl)-phenyl]-3-[2-(4-methyl-piperazin-1-yl)-benzyl]-pyrrolidin-2-one,
1-[4-(1-Methoxy-cyclobutyl)-phenyl]-3-[2-(4-methyl-piperazin-1-yl)-benzyl]-pyrrolidin-2-one,
3-[2-(4-Methyl-piperazin-1-yl)-benzyl]-1-(4-pyridin-4-yl-phenyl)-pyrrolidin-2-one,
1-[4-(1-Hydroxy-cyclopentyl)-phenyl]-3-(2-piperazin-1-yl-benzyl)-pyrrolidin-2-one,
1-[4-(1-Hydroxy-cyclobutyl)-phenyl]-3-(2-piperazin-1-yl-benzyl)- pyrrolidin-2-one,
1-[4-(1-Hydroxy-cyclohexyl)-phenyl]-3-(2-piperazin-1-yl-benzyl)- pyrrolidin-2-one,
1-[4-(1-Ethyl-1-hydroxy-propyl)-phenyl]-3-(2-piperazin-1-yl-benzyl)-pyrrolidin-2-one,
1-[4-(1-Hydroxy-1-methyl-ethyl)-phenyl]-3-(2-piperazin-1-yl-benzyl)-pyrrolidin-2-one,
1-[4-(1-Hydroxy-1-methyl-ethyl)-phenyl]-3-[2-(4-methyl-piperazin-1-yl)-benzylidene]-pyrrolidin-2-one,
3-[2-(4-Ethyl-piperazin-1-yl)-benzyl]-1-[4-(1-hydroxy-1-methyl-ethyl)-phenyl]-pyrrolidin-2-one,
3-[2-(2,5-Dimethyl-piperazin-1-yl)-benzyl]-1-[4-(1-hydroxy-cyclopentyl)-phenyl]-pyrrolidin-2-one,
3-[2-(4-Methyl-piperazin-1-yl)-benzyl]-1-[6-(tetrahydro-pyran-4-yloxy)-pyridin-3-yl]-pyrrolidin-2-one,
1-[6-(1-Hydroxy-cyclopentyl)-pyridin-3-yl]-3-[2-(4-methyl-piperazin-1-yl)-benzyl]-pyrrolidin-2-one,
1-[4-(1-Hydroxy-cyclobutyl)-phenyl]-3-[2-(4-methyl-piperazin-1-yl)-benzyl]-pyrrolidin-2-one,
1-[5-(1-Hydroxy-1-methyl-ethyl)-pyridin-2-yl]-3-[2-(4-methyl-piperazin-1-yl)-benzyl]-pyrrolidin-2-one, and
1-[5-(1-Hydroxy-cyclopentyl)-pyridin-2-yl]-3-[2-(4-methyl-piperazin-1-yl)-benzyl]-pyrrolidin-2-one, and pharmaceutically acceptable salts and optical isomers thereof.

Specific optical isomers of the compounds of the invention include:

(R)-3-[5-Fluoro-2-(4-methyl-piperazin-1-yl)-benzyl]-1-[4-(1-hydroxy-1-methyl-ethyl)-phenyl]-pyrrolidin-2-one,
(R)-4-{3-[2-(4-Methyl-piperazin-1-yl)-benzyl]-2-oxo-pyrrolidin-1-yl}-benzoic acid ethyl ester,
(R)-3-[2-(4-Methyl-piperazin-1-yl)-benzyl]-1-(6-morpholin-4-yl-pyridin-3-yl)-pyrrolidin-2-one,
(R)-1-[4-(1-Hydroxy-1-methyl-ethyl)-phenyl]-3-[2-(4-methyl-piperazin-1-yl)-benzyl]-pyrrolidin-2-one,
(R)-3-[2-(4-Methyl-piperazin-1-yl)-benzyl]-1-(4-morpholin-4-yl-phenyl)-pyrrolidin-2-one,
(R)-1-[4-(1-Hydroxy-cyclopentyl)-phenyl]-3-[2-(4-methyl-piperazin-1-yl)-benzyl]-pyrrolidin-2-one,
(R)-1-[4-(1-Hydroxy-cyclohexyl)-phenyl]-3-[2-(4-methyl-piperazin-1-yl)-benzyl]-pyrrolidin-2-one,
(R)-1-[4-(1-Ethyl-1-hydroxy-propyl)-phenyl]-3-[2-(4-methyl-piperazin-1-yl)-benzyl]-pyrrolidin-2-one,
(R)-1-[3-(1-Hydroxy-1-methyl-ethyl)-phenyl]-3-[2-(4-methyl-piperazin-1-yl)-benzyl]-pyrrolidin-2-one,
(R)-1-[4-(2-Hydroxy-2-methyl-propyl)-phenyl]-3-[2-(4-methyl-piperazin-1-yl)-benzyl]-pyrrolidin-2-one,
(R)-1-[6-(1-Hydroxy-1-methyl-ethyl)-pyridin-3-yl]-3-[2-(4-methyl-piperazin-1-yl)-benzyl]-pyrrolidin-2-one,
(S)-3-[5-Fluoro-2-(4-methyl-piperazin-1-yl)-benzyl]-1-[4-(1-hydroxy-1-methyl-ethyl)-phenyl]-pyrrolidin-2-one,
(S)-4-{3-[2-(4-Methyl-piperazin-1-yl)-benzyl]-2-oxo-pyrrolidin-1-yl}-benzoic acid ethyl ester,
(S)-3-[2-(4-Methyl-piperazin-1-yl)-benzyl]-1-(6-morpholin-4-yl-pyridin-3-yl)-pyrrolidin-2-one,
(S)-1-[4-(1-Hydroxy-1-methyl-ethyl)-phenyl]-3-[2-(4-methyl-piperazin-1-yl)-benzyl]-pyrrolidin-2-one,
(S)-3-[2-(4-Methyl-piperazin-1-yl)-benzyl]-1-(4-morpholin-4-yl-phenyl)-pyrrolidin-2-one,
(S)-1-[4-(1-Hydroxy-cyclopentyl)-phenyl]-3-[2-(4-methyl-piperazin-1-yl)-benzyl]-pyrrolidin-2-one,
(S)-1-[4-(1-Hydroxy-cyclohexyl)-phenyl]-3-[2-(4-methyl-piperazin-1-yl)-benzyl]-pyrrolidin-2-one,
(S)-1-[4-(1-Ethyl-1-hydroxy-propyl)-phenyl]-3-[2-(4-methyl-piperazin-1-yl)-benzyl]-pyrrolidin-2-one,
(S)-1-[3-(1-Hydroxy-1-methyl-ethyl)-phenyl]-3-[2-(4-methyl-piperazin-1-yl)-benzyl]-pyrrolidin-2-one,
(S)-1-[4-(2-Hydroxy-2-methyl-propyl)-phenyl]-3-[2-(4-methyl-piperazin-1-yl)-benzyl]-pyrrolidin-2-one, and
(S)-1-[6-(1-Hydroxy-1-methyl-ethyl)-pyridin-3-yl]-3-[2-(4-methyl-piperazin-1-yl)-benzyl]-pyrrolidin-2-one,
and pharmaceutically acceptable salts thereof.

Unless otherwise indicated, the term "halo", as used herein, includes fluoro, chloro, bromo and iodo.

Unless otherwise indicated, the term "alkyl", as used herein, includes straight or branched alkyl groups having one to eight carbon atoms.

Unless otherwise indicated the term "cycloalkyl" as used herein includes moieties derived from cyclic hydrocarbons containing from four to seven ring carbon atoms, including cyclic hydrocarbon moieties substituted with straight or branched alkyl moieties.

Unless otherwise indicated the term "heterocycloalkyl" as used herein includes a cyclic hydrocarbon in which one or more of the ring carbon atoms has been replaced with a nitrogen, oxygen or sulfur atom or any combination thereof. Examples of such groups are oxetanyl, tetrahydrofuranyl, pyranyl, azetidinyl, pyrrolidinyl, piperidinyl, morpholinyl, thiomorphlinyl, piperazinyl, and azapinyl.

The term "alkoxy", as used herein, means "alkyl-O—", wherein "alkyl" is defined as above.

The term "alkylene, as used herein, means an alkyl radical having two available bonding sites (i.e., -alkyl-), wherein "alkyl" is defined as above.

The term "alkenyl" is intended to include hydrocarbon chains of either a straight or branched configuration comprising one or more unsaturated carbon-carbon bonds which may occur in any stable point along the chain, such as ethenyl and propenyl. Alkenyl groups typically will have 2 to about 12 carbon atoms, more typically 2 to about 8 carbon atoms.

The term "alkynyl" is intended to include hydrocarbon chains of either a straight or branched configuration comprising one or more triple carbon-carbon bonds which may occur in any stable point along the chain, such as ethynyl and propynyl. Alkynyl groups typically will have 2 to about 12 carbon atoms, more typically 2 to about 8 carbon atoms. The term "aryl" is intended to include groups that, in accordance with the theory of Hucckel, have a cyclic, delocalized (4n+2) pi-electron system containing from five to about twelve ring atoms. Examples of aryl groups include, but are not limited to, arenes and their substitution products, e.g. phenyl, naphthyl and toluyl, among numerous others.

The term "heteroaryl" is intended to include aromatic heterocyclic groups and includes the non-limiting examples thiophenyl, pyridyl, pyrimidyl, pyridazyl, oxazolyl, isooxazolyl, thiazolyl and isothiazolyl, among others.

Unless otherwise indicated, the term "one or more substituents", as used herein, refers to from one to the maximum number of substituents possible based on the number of available bonding sites.

The compounds of formula I may have chiral centers and therefore may occur in different enantiomeric configurations. The invention includes all enantiomers, diastereomers, and other stereoisomers, as well as any possible tautomers of such compounds of formula I, as well as racemic and other mixtures thereof.

The present invention also relates to the pharmaceutically acceptable acid addition salts of the compounds of formula I. Examples of pharmaceutically acceptable acid addition salts of the compounds of formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleic acid, di-p-toluoyl tartaric acid, and mandelic acid.

The present invention also, relates to all radiolabeled forms of the compounds of the formula I. Preferred radiolabeled compounds of formula I are those wherein the radiolabels are selected from as $^{3}H$, $^{11}C$, $^{14}C$, $^{18}F$, $^{123}I$ and $^{125}I$. Such radiolabeled compounds are useful as research and diagnostic tools in metabolism pharmacokinetics studies and in binding assays in both animals and man.

The present invention also relates to a pharmaceutical composition for treating a disorder or condition in a mammal, including a human, selected from depression, anxiety, depression with concomitant anxiety, dysthymia, post traumatic stress disorder, panic phobias, obsessive compulsive disorder (OCD), OCD with comorbid Tourelte's Syndrome, borderline personality disorder, sleep disorder, psychosis, seizures, dyskinesis, symptoms of Huntington's or Parkinson's diseases, spasticity, suppression of seizures resulting from epilepsy, cerebral ischemia, anorexia, faintness attacks, hypokinesia, cranial traumas, chemical dependencies, premature ejaculation, premenstrual syndrome (PMS) associated mood and appetite disorder, inflammatory bowel disease, modification of feeding behavior, blocking carbohydrate cravings, late luteal phase dysphoric disorder, tobacco withdrawal-associated symptoms, panic disorder, bipolar disorder, sleep disorders, jet lag, cognitive dysfunction, hypertension, bulimia, anorexia, obesity, cardiac arrhythmias, chemical dependencies and addictions selected from dependencies on, or addictions to nicotine or tobacco products, alcohol, benzodiazepines, barbiturates, opioids or cocaine; pathological gambling; trichotilomania; headache, stroke, traumatic brain injury (TBI), psychosis, Huntington's Chorea, tardive dyskinesia, hyperkinesia, dyslexia, schizophrenia, multi-infarct dementia, epilepsy, senile dementia of the Alzheimer's type (AD), Parkinson's disease (PD), attention deficit hyperactivity disorder (ADHD) and Tourette's Syndrome, comprising an amount of a compound of the formula I, or a pharmaceutically acceptable salt thereof, and a pharmaceutically acceptable carrier.

The present invention also relates to a method of treating a disorder or condition referred to hereinabove in a mammal, including a human, comprising administering to a mammal in need of such treatment an amount of a compound of the formula I, or a pharmaceutically acceptable salt thereof, that is effective in treating such disorder or condition.

The present invention also relates to a pharmaceutical composition for use in treating a disorder or condition referred to hereinabove in a mammal, comprising an amount of a compound according of the formula I that is an effective antagonist, inverse agonist or partial agonist of $5\text{-}HT_{1B}$ receptors and a pharmaceutically acceptable carrier.

The present invention also relates to a method of treating a disorder or condition referred to hereinabove in a mammal, comprising administering to a mammal in need of such treatment an amount of a compound of the formula I that is an effective antagonist, inverse agonist or partial agonist of $5\text{-}HT_{1B}$ receptors.

As used herein, the term "depression" includes depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias, seasonal affective disorder, or bipolar disorders or manic depression, for example, bipolar I disorder, bipolar II disorder and cyclothymic disorder.

Other mood disorders encompassed within the term "depression" include dysthymic disorder with early or late onset and with or without atypical features; dementia of the Alzheimer's type, with early or late onset, with depressed mood; vascular dementia with depressed mood, disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood.

As used herein, the term "anxiety" includes anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalized anxiety disorders.

"Generalized anxiety" is typically defined as an extended period (e.g. at least six months) of excessive anxiety or worry with symptoms on most days of that period. The anxiety and worry is difficult to control and may be accompanied by restlessness, being easily fatigued, difficulty concentrating, irritability, muscle tension, and disturbed sleep.

"Panic disorder" is defined as the presence of recurrent panic attacks followed by at least one month of persistent concern about having another panic attack. A "panic attack" is a discrete. period in which there is a sudden onset of intense apprehension, fearfulness or terror. During a panic attack, the individual may experience a variety of symptoms including palpitations, sweating, trembling, shortness of breath, chest pain, nausea and dizziness. Panic disorder may occur with or without agoraphobia.

"Phobias" includes agoraphobia, specific phobias and social phobias. "Agoraphobia" is characterized by an anxiety about being in places or situations from which escape might be difficult or embarrassing or in which help may not be available in the event of a panic attack. Agoraphobia may occur without history of a panic attack. A "specific phobia" is characterized by clinically significant anxiety provoked by feared object or situation. Specific phobias include the following subtypes: animal type, cued by animals or insects; natural environment type, cued by objects in the natural environment, for example storms, heights or water; blood-injection-injury type, cued by the sight of blood or an injury or by seeing or receiving an injection or other invasive medical procedure; situational type, cued by a specific situation such as public transportation, tunnels, bridges, elevators, flying, driving or enclosed spaces; and other type where fear is cued by other stimuli. Specific phobias may also be referred to as simple phobias. A "social phobia" is characterized by clinically significant anxiety provoked by exposure to certain types of social or performance circumstances. Social phobia may also be referred to as social anxiety disorder.

Other anxiety disorders encompassed within the term "anxiety" include anxiety disorders induced by alcohol, amphetamines, caffeine, cannabis, cocaine, hallucinogens, inhalants, phencychdine, sedatives, hypnotics, anxiolytics and other substances, and adjustment disorders with anxiety or with mixed anxiety and depression.

DETAILED DESCRIPTION OF THE INVENTION

Except where otherwise stated, $R^1$, $R^3$, X, $G^1$, $G^2$, $R^6$, $R^{13}$, n and m in schemes and discussions that follow are defined as above. Unless otherwise stated reaction conditions for all reaction schemes include an inert atmosphere commonly used in the art such as nitrogen or argon.

Schemes 1 and 1a to 1d refer to general methods suitable for preparing compounds of formula I wherein $R^1=G^1$. In step 1 of Scheme 1 a mixture of 2-substituted benzaldehyde V wherein the substituent at the 2-position, indicated as Z in Scheme 1, is a functional group that has the ability to undergo oxidative addition such as, but not limited to, F, Cl, Br, I, and sulfonate, such as 2-fluorobenzaldehyde, and an N-substituted compound of the formula IV are treated in a solvent selected from water, 1,4-dioxane, n-butanol, N,N-dimethylformamide, dimethyl sulfoxide, acetonitrile or mixtures thereof, preferably water, with a base such as a trialkyl amine or an alkali metal carbonate, preferably potassium carbonate, at a temperature of about 40° C. to about 150° C., preferably about 90° C. to about 120° C. to yield an aldehyde of the formula III. A mixture of the 2-Z-benzaldehyde and N-substituted compound of the formula IV are treated in a solvent selected from toluene, benzene, DME wherein toluene is preferred with a base such as sodium or potassium tert-butoxide, sodium or potassium carbonate, potassium phosphonate preferably sodium tert-butoxide with a palladium source such as tetrakis(triphenylphosphine)palladium, palladium acetate, tris(dibenzyidene-acetone)dipalladium, trans-dichloro-bis(triphenylphospine)palladium or optionally added phosphine ligands where added such as BINAP or triphenylphosphine where palladium acetate and BINAP is preferred at a temperature of about 40° C. to 150° C., preferably about 90° C. to 120° C. to yield an aldehyde of the formula III.

Step 2 of Scheme 1 is an addition reaction of N-substituted lactam II to the aldehyde of formula III, wherein the N-substituent $R^3$ is vinyl or C(=O)R, wherein R is $C_1$-$C_8$ straight chain or branched alkyl, $C_3$-$C_8$ cycloalkyl, aryl, or $CF_3$, wherein R is preferably tert-butyl, using an amine or hydridic metal base such as sodium hydride or sodium bis(trimethylsilylamide), preferably sodium bis(trimethylsilylamide), in a reaction inert reaction solvent, preferably an ethereal solvent selected from diethyl ether, dioxane and tetrahydrofuran, most preferably tetrahydrofuran, at a temperature of from about −30° C. to about 100° C., preferably from about −10° C. to 30° C., to produce a compound of the formula I, wherein the dotted line represents a carbon-carbon double bond, and is designated IB in Scheme 1 (see Sasaki, H. et al. *J. Med. Chem.*, 1991, 34, 628-633). In one embodiment, $R^3$ is removed under the reaction conditions. In other embodiments, e.g., where $R^3$ is vinyl, a separate deprotection step is required. In this case, $R^3$ may be removed using aqueous acid work-up such as trifluoroacetic acid or hydrochloric acid, trifluoroacetic acid being preferred.

Step 3 of Scheme 1 is a catalytic reduction of the carbon-carbon double bond of IB to produce a compound of the formula I, designated IA in Scheme 1. The reduction of this double bond may be effected with hydrogen gas ($H_2$) in a reaction inert solvent such as a lower alcohol, THF, dioxane or ethyl acetate, preferably methanol or ethanol, in the presence of a noble metal catalyst on a solid support such as palladium on carbon (Pd/C), palladium on barium sulfate (Pd/BaSO$_4$), platinum on carbon (Pt/C), or tris(triphenylphosphine) rhodium chloride (Wilkinson's catalyst), preferably about 10% palladium on carbon, at a pressure of from about 1 to about 5 atmospheres, preferably about 3 to about 4 atmospheres, at a temperature of about 10° C. to about 100° C., preferably 40° C. to 60° C. while shaking the reaction mixture. Alternatively, the double bond may be reduced under transfer hydrogenation conditions where a hydride donor such as cyclohexadiene or ammonium formate is used in place of hydrogen, where ammonium formate is preferred, in a reaction inert solvent such as a lower alcohol, THF, dioxane or ethyl acetate, preferably methanol or ethanol, in the presence of a noble metal catalyst on a solid support such as palladium on carbon (Pd/C), palladium on barium sulfate (Pd/BaSO$_4$), platinum on carbon (Pt/C), or tris(triphenylphosphine) rhodium chloride (Wilkinson's catalyst), preferably about 10% palladium on carbon, at a temperature of about 20° C. to 150° C., preferably 40° C. to 80° C. Alternatively, the reduction of the carbon-carbon double bond of 1B to produce a compound of the formula I, designated 1A in Scheme 1 can be accomplished using alternative procedures known to one skilled in the art. Larock, R. C. Comprehensive Organic Transformations. VCN Publishers, 1989. In those cases where $R^6$ is benzyl or another group that is labile under hydrogenation conditions, the corresponding NH derivative (i.e., $R^6$=H) is formed.

Step 4 of Scheme 1 depicts the conversion of a compound of formula IA (the compound of formula I in which the optional double is absent) wherein $R^3$ is hydrogen to a compound of the formula IA' wherein $R^3$ is an optionally substituted aryl or heteroaryl group, by means of N-arylation or N-heteroarylation. The compound of formula IA is treated with an aryl or heteroaryl chloride, bromide, iodide, or sulfonate, preferably the bromide, a base such as potassium phosphate, potassium carbonate, sodium carbonate, thallium carbonate, cesium carbonate, potassium tert-butoxide, lithium tert-butoxide, or sodium tert-butoxide, preferably potassium carbonate, a diamine, such as 1,2-ethylenediamine, N,N'-dimethylethylenediamine, N,N-dimethylethylenediamine, or cis-1,2-diaminocyclohexane, preferably N,N'-dimethylethylenediamine, and cuprous chloride, bromide or iodide or other copper(I) salts, preferably cuprous iodide, in the presence of a small amount of water, preferably about 1% to about 4% water (w/w relative to the compound of formula II), in a reaction inert solvent such as 1,2-dimethoxyethane, diglyme, t-butyl methyl ether, tetrahydrofuran, benzene or toluene, preferably toluene, optionally in the presence of a polar co-solvent such as DMF or dimethyl acetamide in the order of 5-15% vol/vol relative to the first solvent, at a temperature of about 40° C. to about 150° C., preferably about 80° C. to about 120° C. to yield the compound of formula IA' wherein $R^3$ is optionally substituted aryl or heteroaryl.

The N-arylation or N-heteroarylation in step 4 of Scheme 1 may also be accomplished by treating a compound of formula IA (the compound of formula I in which the optional double is absent) wherein $R^3$ is hydrogen with an aryl or heteroaryl chloride, bromide, iodide, or sulfonate, preferably the bromide with a base such as an alkali metal carbonate, an alkali metal amine base, an alkali metal phosphonate, or an alkali metal alkoxide, preferably cesium carbonate, a phosphine ligand, preferably 9,9-dimethyl-4,5-bis(diphenyl-phosphino)xanthene (XANTPHOS), and a palladium species, such as palladium(II)acetate or tris(dibenzylideneacetone)dipalladium(0) or the corresponding chloroform adduct, preferably tris(dibenzylideneacetone)dipalladium(0), in an inert solvent such as 1,4-dioxane or toluene, preferably 1,4-dioxane, at a temperature of about 40° C. to about 160° C., preferably about 80° C. to about 120° C. For compounds of formula I wherein $R^6$ is H further functionalization of the secondary amine can be carried out under standard alkylation or reductive amination conditions known to one skilled in the art.

Alternatively, in step 3a of scheme 1, the compound of formula IB may be converted to the N-aryl or N-heteroaryl derivative having formula 1B' using the procedures of step 4 above. The compound of formula I wherein $R^1$ is $G^1$ and $R^3$ is an optionally substituted aryl or heteroaryl group, designated IA' in Scheme 1 is then prepared in step 4a of Scheme 1 using the procedures of step 3 above.

In those cases where $R^6$ is benzyl or another group that is labile under hydrogenation conditions, the corresponding secondary amine derivative (i.e., $R^6$ is H) is formed. If $R^6$ is H, further functionalization of the secondary amine can be carried out under standard alkylation or reductive amination conditions known to those skilled in the art.

SCHEME I

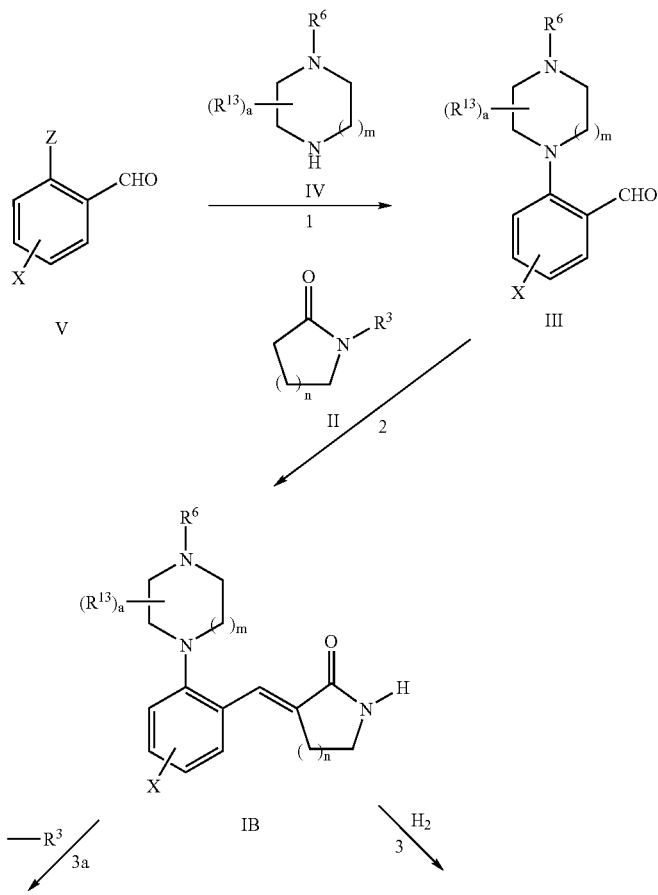

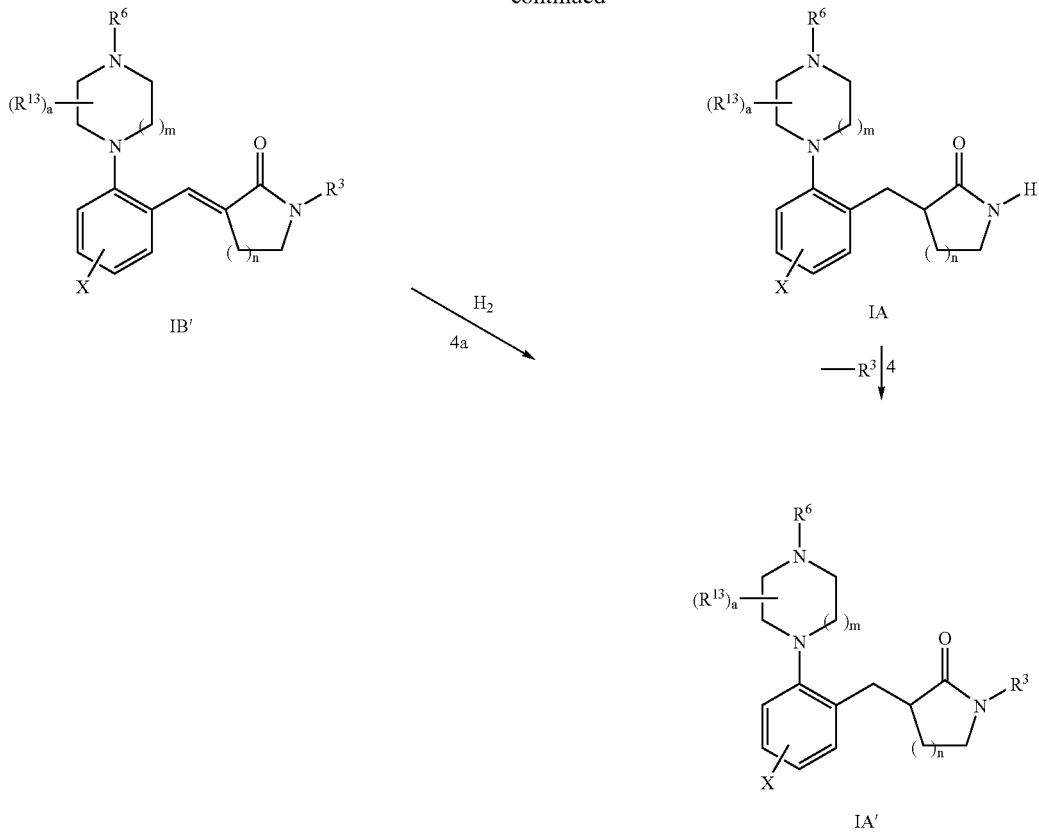

Scheme 1a depicts the preparation of a compound of the formula I, wherein the optional double bond is either present or absent beginning with N-arylation or N-heteroarylation of lactam IIa to form lactam II wherein $R^3$ is an optionally substituted aryl or heteroaryl group.

In step 1 of Scheme 1a lactam IIA is treated with an aryl or heteroaryl chloride, bromide, iodide, or sulfonate, preferably the bromide, a base such as potassium phosphate, potassium carbonate, sodium carbonate, thallium carbonate, cesium carbonate, potassium tert-butoxide, lithium tert-butoxide, or sodium tert-butoxide, preferably potassium carbonate, a diamine, such as 1,2-ethylenediamine, N,N'-dimethylethylenediamine, N,N-dimethylethylenediamine or cis-1,2-diaminocyclohexane, preferably N,N'-dimethyl-ethylenediamine, and cuprous chloride, bromide or iodide, preferably cuprous iodide, in the presence of a small amount of water, preferably about 1% to about 4% water, in a reaction inert solvent such as 1,2-dimethoxyethane, diglyme, t-butyl methyl ether, tetrahydrofuran, benzene or toluene, preferably toluene, at a temperature of about 40° C. to about 150° C., preferably about 80° C. to about 120° C. to yield the lactam of formula II wherein $R^3$ is optionally substituted aryl or heteroaryl.

The N-arylation or N-heteroarylation of step 1, Scheme 1a may also be accomplished by treating a lactam of formula IIA wherein $R^3$ is hydrogen with an aryl or heteroaryl chloride, bromide, iodide, or sulfonate, preferably the bromide with a base such as an alkali metal carbonate, an alkali metal amine base, an alkali metal phosphonate, or an alkali metal alkoxide, preferably cesium carbonate, a phoshpine ligand, preferably 9,9-dimethyl-4,5-bis(diphenylphosphino)xanthene (XANTPHOS), and a palladium species, such as palladium (II) acetate or tris(dibenzylideneacetone)dipalladium(0) or the corresponding chloroform adduct, preferably tris(dibenzylideneacetone)dipalladium(0), in an inert solvent such as 1,4-dioxane or toluene, preferably 1,4-dioxane, at a temperature of about 40° C. to about 160° C., preferably about 80° C. to about 120° C.

In Step 2 of Scheme 1a compound 1B' is prepared by treating aldehyde III, prepared as in Scheme I, with lactam II, wherein $R^3$ is optionally substituted aryl or heteroaryl, using the procedure of step 2 in Scheme 1.

In Step 2 of Scheme 1a, compound 1B' can alternatively be prepared by treating aldehyde III, prepared as in Scheme I, with lactam II, wherein $R^3$ is optionally substituted aryl or heteroaryl, in a solvent such as tetrahydrofuran, tert-butylmethyl ether, or 1,4-dioxane, preferably tetrahydrofuran, in the presence of an alkali metal amine base, such as sodium bis(trimethylsilylamide), potassium bis(trimethylsilylamide), lithium bis(trimethylsilylamide), or lithium diisopropylamide, or an alkali metal hydride, such as sodium hydride or potassium hydride, preferably sodium bis(trimethylsilylamide), which is then followed by the addition of diethylchlorophosphonate at a temperature of about –30° C. to about 100° C., preferably about –10° C. to about 30° C.

In step 3 of Scheme 1a compound IA' is prepared by catalytic hydrogenation of compound IB' using the procedure of step 3 in Scheme 1.

SCHEME IA

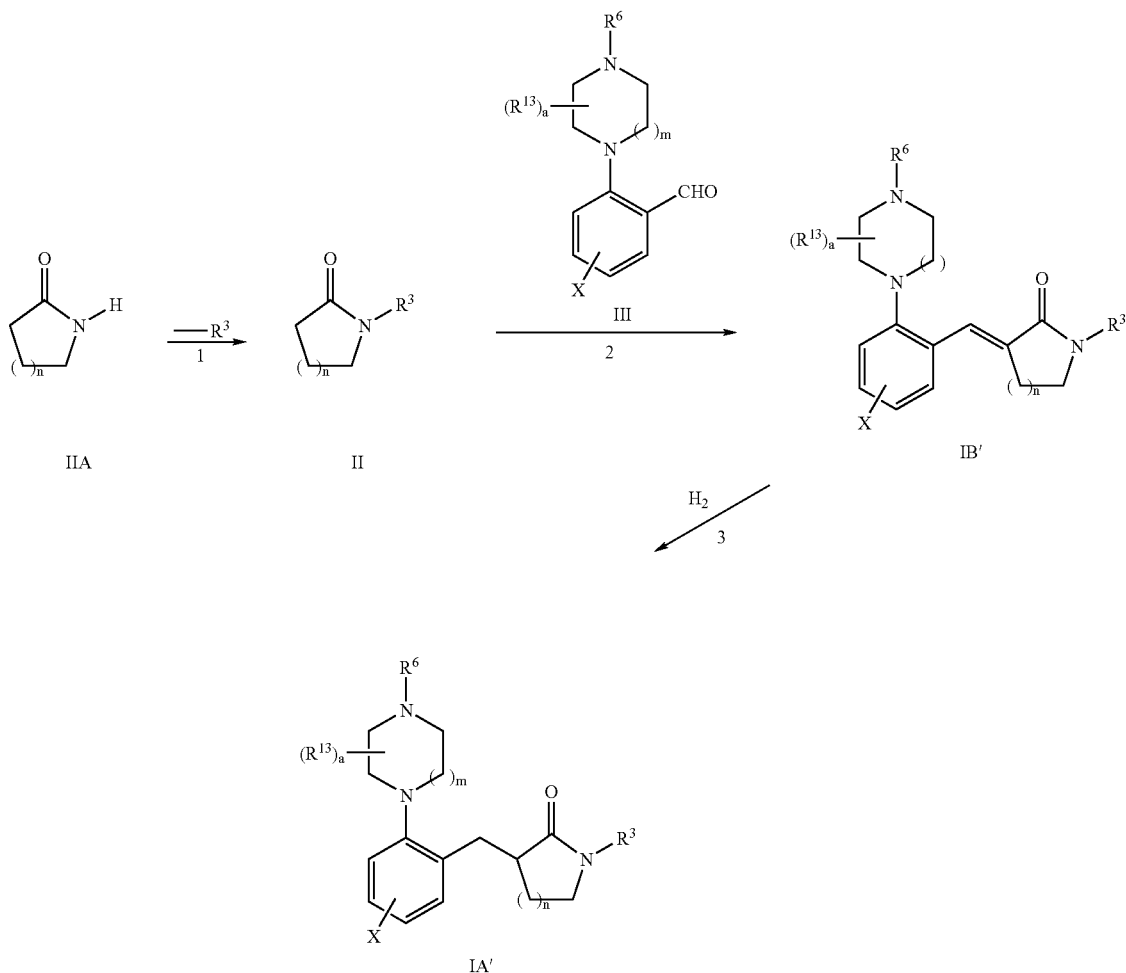

Scheme 1b depicts an alternative preparation of a lactam of formula II wherein $R^3$ is an optionally substituted aryl or heteroaryl group.

In step 1 of Scheme 1b, a compound $R^3$—NH2, wherein $R^3$ is an optionally substituted aryl or heteroaryl group, is treated with a compound of the formula VI wherein, group A of VI is selected from F, Cl, Br, I or an alkyl or aryl sulfonate, preferably Cl, and group B is selected from F, Cl, Br, I, $OC_1$-$C_4$ alkyl, OH, or an activated carboxylic acid group derived from reaction of the corresponding carboxylic acid with a standard carboxylic acid activating reagent such as, but not limited to, a carbodiimide (dicyclohexyl carbodiimide, 1-(3-dimethylaminopropyl)-3-ethylcarbodiimide hydrochloride salt) or tripropylphosphonic anhydride, preferably Cl, in a solvent such as water, acetonitrile, 1,4-dioxane, or tetrahydrofuran, or combinations thereof, preferably tetrahydrofuran, at a temperature of about 10° C. to about 120° C., preferably about 50° C. to about 80° C., in the presence or absence of a base, such as triethylamine, diisopropylethyl amine, an alkali metal hydroxide or an alkali metal carbonate, preferably cesium carbonate.

Compounds IB' and IA' can then be prepared by the procedures of Scheme Ia.

SCHEME IB

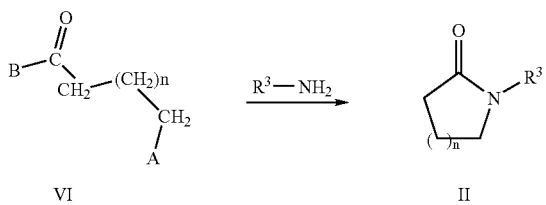

In those cases where $R^6$ is benzyl or another group that is labile under hydrogenation conditions, the corresponding secondary amine derivative (i.e. $R^6$ is H) is formed. If $R^6$ is H, further functionalization of the secondary amine can be carried out under standard alkylation or reductive amination conditions known to those skilled in the art.

Scheme 1c depicts yet another alternative preparation of the compounds of formula IB' and IA' wherein $R^3$ is an optionally substituted aryl or heteroaryl group.

In Step 1 of Scheme 1c a compound of the formula VIII is prepared by treating ortho halo-benzaldehyde VII, wherein D is selected from chloro, bromo, or iodo, preferably bromo, with a lactam of the formula II, wherein $R^3$ is an optionally substituted aryl or heteroaryl group, in a solvent such as tetrahydrofuran, tert-butylmethyl ether, or 1,4-dioxane, preferably tetrahydrofuran, in the presence of an alkali metal amine base, such as sodium bis(trimethylsilylamide), potassium bis(trimethylsilylamide), lithium bis(trimethylsilylamide), or lithium diisopropylamide, or an alkali metal hydride, such as sodium hydride or potassium hydride, preferably sodium bis(trimethylsilylamide).

In Step 2 of Scheme 1c, a compound of the formula IB' is prepared by treating a compound of the formula VIII with an N-substituted compound of the formula IV in a solvent selected from water, 1,4-dioxane, n-butanol, N,N-dimethylformamide, dimethyl sulfoxide, acetonitrile or mixtures thereof, preferably water, with a base such as a trialkyl amine or an alkali metal carbonate, preferably potassium carbonate, at a temperature of about 40° C. to about 150° C., preferably about 90° C. to about 120° C. to yield the compound of the formula IB'. Alternatively, this coupling can be facilitated by use of an transition metal such as palladium and the preferred method is that of Buchwald as described in Buchwald et al. *J. Org. Chem.* 2000,65, p1144-1157 and p1158-1174. A mixture of VIII and N-substituted compound of the formula IV are treated in a solvent selected from toluene, benzene, and DME, wherein toluene is preferred, with a base such as sodium or potassium tert-butoxide, sodium or potassium carbonate, potassium phosphonate, preferably sodium tert-butoxide with a palladium source such as tetrakis(triphenylphosphine)palladium, palladium acetate, tris(dibenzyideneacetone)dipalladium, transdichlorobis(triphenylphospine)palladium or optinally added phospine ligands were added such as BINAP or triphenylphosphine where palladium acetate and BINAP is preferred at a temperature of about 40° C. to 150° C., preferably about 900° C. to 120° C. to yield a compound of formula IB'. The compound of the formula IB' can then be converted to the compound of the formula IA' as described above.

Step 3 of Scheme 1c is a catalytic reduction of the carbon-carbon double bond of IB' to produce a compound of the formula I, designated IA' in Scheme 1. The reduction of this double bond may be effected with hydrogen gas ($H_2$) in a reaction inert solvent such as a lower alcohol, THF, dioxane or ethyl acetate, preferably methanol or ethanol, in the presence of a noble metal catalyst on a solid support such as palladium on carbon (Pd/C), palladium on barium sulfate ($Pd/BaSO_4$), platinum on carbon (Pt/C), or tris(triphenylphosphine) rhodium chloride (Wilkinson's catalyst), preferably about 10% palladium on carbon, at a pressure of from about 1 to about 5 atmospheres, preferably about 3 to about 4 atmospheres, at a temperature of about 10° C. to about 100° C., preferably 40° C. to 60° C. while shaking the reaction mixture. Alternatively, the double bond may be reduced under transfer hydrogenation conditions where a hydride donor such as cyclohexadiene or ammonium formate is used in place of hydrogen, where ammonium formate is preferred, in a reaction inert solvent such as a lower alcohol, THF, dioxane or ethyl acetate, preferably methanol or ethanol, in the presence of a noble metal catalyst on a solid support such as palladium on carbon (Pd/C), palladium on barium sulfate ($Pd/BaSO_4$), platinum on carbon (Pt/C), or tris(triphenylphosphine) rhodium chloride (Wilkinson's catalyst), preferably about 10% palladium on carbon, at a temperature of about 20° C. to 1 50° C., preferably 40° C. to 80° C.

Alternatively, the reduction of the carbon-cabon double bond of 1B to produce a compound of the formula I, designated 1A in Scheme 1 can be accomplished using alternative procedures known to one skilled in the art. Larock, R. C. Comprehensive Organic Transformations. VCN Publishers, 1989.

SCHEME 1C

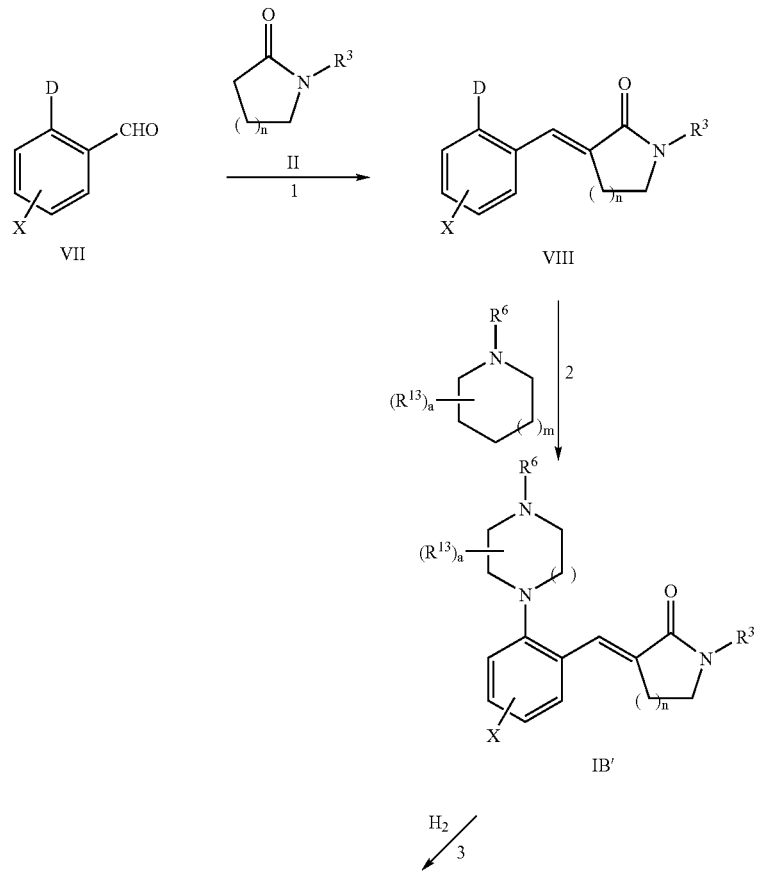

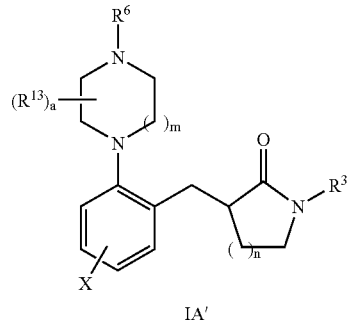

IA'

Schemes 2, 2a and 2b refer to general methods suitable for preparing compounds of formula I wherein $R^1=G^2$.

Step 1 of Scheme 2 illustrates preparation of a compound XI by coupling boronic acid or boronic ester IX wherein L is selected from OH and $O(C_1-C_4)$alkyl or wherein both L substituents together form a 1,3,2-benzodioxaborole derivative, preferably L is OH with halopyridine X, wherein the halo group HI is selected from chloro, bromo or iodo or sulfonate, preferably bromo, in the presence of a palladium catalyst, such as palladium tetrakistriphenylphosphine, dichloropalladium bistriphenylphosphine, or tris(dibenzidene-acetone)dipalladium, preferably palladium tetrakistriphenylphosphine, and an alkali metal base, such as sodium carbonate, potassium carbonate, cesium carbonate, sodium hydroxide, or potassium hydroxide, preferably sodium carbonate, in a solvent system containing dimethoxyethane and a polar protic solvent such as water, methanol, or ethanol, preferably water, at a temperature of from about 10° C. to about 150° C., preferably about 70° C. to about 110C.

In Step 2 of Scheme 2 compound XII is prepared by treating compound XI with N-substituted lactam II wherein the N-substituent $R^3$, is vinyl or C(=O)R, wherein R is $C_1-C_8$ straight chain or branched alkyl, $C_3-C_8$ cycloalkyl, or aryl, CF3, preferably tert-butyl, in the presence of an amine or hydridic metal base such as sodium hydride or sodium bis (trimethylsilylamide), preferably sodium bis(trimethylsilylamide), in a reaction inert reaction solvent, preferably an ethereal solvent selected from diethyl ether, dioxane and tetrahydrofuran, most preferably tetrahydrofuran, at a temperature of from about –30° C. to about 100° C., preferably from about –10° C. to 30° C. In embodiments where $R_3$ is vinyl, aqueous acid, preferably trifluoroacetic acid, is used in the workup to remove $R_3$.

In Step 3 of Scheme 2 compound XIII is prepared by alkylation of the pyridinyl nitrogen of compound XII and partial reduction of the pyridinyl ring. Compound XII is treated with an excess of an alkyl iodide, alkyl methanesulfonate, alkyl arylsulfonate, or alkyl triflate, in a solvent such as acetonitrile or 1,4-dioxane, preferably acetonitrile, at a temperature of about 20° C. to about 150° C., preferably 70° C. to 90° C., for about 10 minutes to about 60 hours, a period of time sufficient to alkylate the pyridine nitrogen, followed by removal of solvent in vacuo, and subsequent addition of a lower alcohol solvent, preferably methanol, followed by the addition of sodium borohydride.

In step 4 of Scheme 2 a compound of the formula I, wherein $R^1$ is $G^2$ and $R^3$ is H, designated IC in Scheme 2 is prepared by catalytic reduction of the carbon-carbon double bond of XIII. The reduction of this double bond may be effected with hydrogen gas ($H_2$) in a reaction inert solvent such as a lower alcohol, THF, dioxane or ethyl acetate, preferably methanol or ethanol, in the presence of a noble metal catalyst on a solid support such as palladium on carbon (Pd/C), palladium on barium sulfate (Pd/BaSO$_4$), platinum on carbon (Pt/C), or tris(triphenylphosphine) rhodium chloride (Wilkinson's catalyst), preferably about 10% palladium on carbon, at a pressure of from about 1 to about 5 atmospheres, preferably about 3 to about 4 atmospheres, at a temperature of about 10° C. to about 100° C., preferably 40° C. to 60° C. while shaking the reaction mixture. Alternatively, the double bond may be reduced under transfer hydrogenation conditions where a hydride donor such as cyclohexadiene or ammonium formate is used in place of hydrogen, where ammonium formate is preferred, in a reaction inert solvent such as a lower alcohol, THF, dioxane or ethyl acetate, preferably methanol or ethanol, in the presence of a noble metal catalyst on a solid support such as palladium on carbon (Pd/C), palladium on barium sulfate (Pd/BaSO$_4$), platinum on carbon (Pt/C), or tris(triphenylphosphine) rhodium chloride (Wilkinson's catalyst), preferably about 10% palladium on carbon, at a temperature of about 20° C. to 150° C., preferably 40° C. to 80° C.

Alternatively, the reduction of the carbon-carbon double bond of XIII to produce a compound of the formula I, designated 1C in Scheme 2 can be accomplished using alternative procedures known to one skilled in the art. Larock, R. C. Comprehensive Organic Transformations. VCN Publishers, 1989.

In Step 5 of Scheme 2 the compound of the formula IC', wherein $R^1$ is $G^2$ and $R^3$ is an optionally substituted aryl or heteroaryl group, is prepared from the compound of formula IC wherein $R^1$ is $G^2$ and $R^3$ is H by means of N-arylation or N-heteroarylation. The compound of formula IC is treated with an aryl or heteroaryl chloride, bromide, iodide, or sulfonate, preferably the bromide, a base such as potassium phosphate, potassium carbonate, sodium carbonate, thallium carbonate, cesium carbonate, potassium tert-butoxide, lithium tert-butoxide, or sodium tert-butoxide, preferably potassium carbonate, a diamine, such as 1,2-ethylenediamine, N,N'-dimethylethylenediamine, N,N-dimethylethylenediamine or cis-1,2-diaminocyclohexane, preferably N,N'-dimethylethylenediamine, and cuprous chloride, bromide or iodide or other Copper (1) sources, preferably cuprous iodide, in the presence of a small amount of water, preferably about 1% to about 4% water, in a reaction inert solvent such as 1,2-dimethoxyethane, diglyme, t-butyl methyl ether, tetrahydrofuran, benzene or toluene, preferably toluene, at a temperature of about 40° C. to about 150° C., preferably about 80° C. to about 120° C. to yield the compound of formula IC' wherein $R^3$ is optionally substituted aryl or heteroaryl.

The N-arylation or N-heteroarylation in Step 5 of Scheme 2 may also be accomplished by treating a compound of formula IC wherein $R^1$ is $G^2$ and $R^3$ is H with an aryl or heteroaryl chloride, bromide, iodide, or sulfonate, preferably the bromide with a base such as an alkali metal carbonate, an alkali metal amine base, an alkali metal phosphonate, or an alkali metal alkoxide, preferably cesium carbonate, a phoshpine ligand, preferably 9,9-dimethyl-4,5-bis(diphenylphosphino)xanthene (XANTPHOS), and a palladium species, such as palladium (II) acetate or tris(dibenzylideneacetone)dipalladium(0) or the corresponding chloroform adduct, preferably tris(dibenzylideneacetone)dipalladium(0), in an inert solvent such as 1,4-dioxane or toluene, preferably 1,4-dioxane, at a temperature of about 40° C. to about 160° C., preferably about 80° C. to about 120° C. For compounds of formula IC or IC' wherein $R^6$ is H further functionalization of the secondary amine can be carried out under standard alkylation or reductive amination conditions known to one skilled in the art.

SCHEME 2

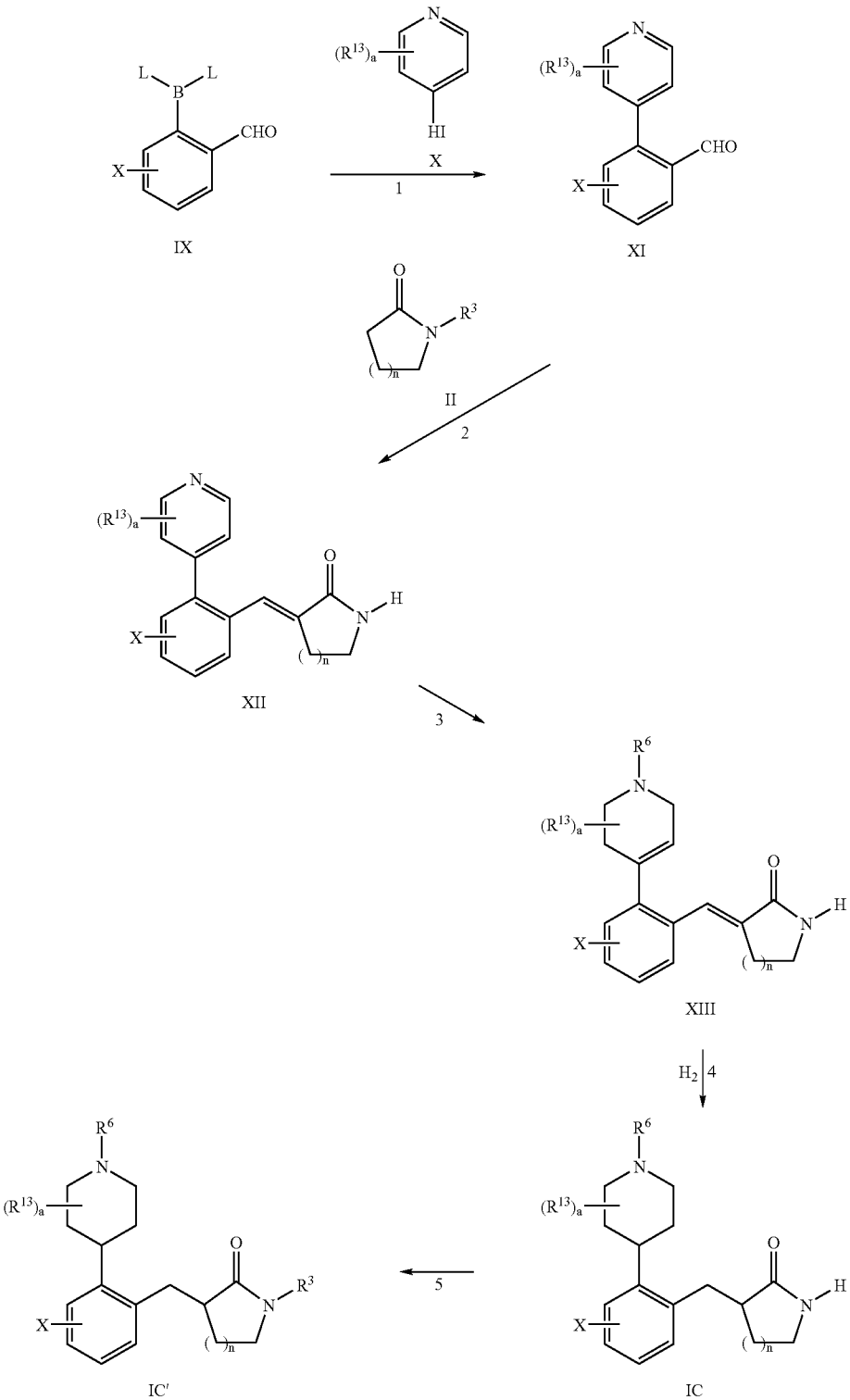

Scheme 2a depicts an alternate route to a compound of the formula IC' wherein $R^1$ is $G^2$. In Step 1 of Scheme 2a, the compound of formula XII is converted to a compound of formula XIV wherein $R^3$ is an optionally substituted aryl or heteroaryl group, by N-arylation or N-heteroarylation. The compound of formula XII is treated with an aryl or heteroaryl chloride, bromide, iodide, or sulfonate, preferably the bromide, a base such as potassium phosphate, potassium carbonate, sodium carbonate, thallium carbonate, cesium carbonate, potassium tert-butoxide, lithium tert-butoxide, or sodium tert-butoxide, preferably potassium carbonate, a diamine, such as 1,2-ethylenediamine, N,N'-dimethylethylenediamine, N,N-dimethyl-ethylenediamine or cis-1,2-diaminocyclohexane, preferably N,N'-dimethylethylenediamine, and cuprous chloride, bromide or iodide, preferably cuprous iodide, in the presence of a small amount of water, preferably about 1% to about 4% water, in a reaction inert solvent such as 1,2-dimethoxyethane, diglyme, t-butyl methyl ether, tetrahydrofuran, benzene or toluene, preferably toluene, at a temperature of about 40° C. to about 150° C., preferably about 80° C. to about 120° C. to yield the compound of formula XIV wherein $R^3$ is optionally substituted aryl or heteroaryl.

The N-arylation or N-heteroarylation in Step 1 of Scheme 2a may also be accomplished by treating a compound of formula XII wherein $R^1$ is $G^2$ and $R^3$ is H with an aryl or heteroaryl chloride, bromide, iodide, or sulfonate, preferably the bromide with a base such as an alkali metal carbonate, an alkali metal amine base, an alkali metal phosphonate, or an alkali metal alkoxide, preferably cesium carbonate, a phosphine ligand, preferably 9,9-dimethyl-4,5-bis(diphenylphosphino)xanthene (XANTPHOS), and a palladium species, such as palladium(II)acetate or tris(dibenzylideneacetone)dipalladium(0) or the corresponding chloroform adduct, preferably tris(dibenzylideneacetone)dipalladium(0), in an inert solvent such as 1,4-dioxane or toluene, preferably 1,4-dioxane, at a temperature of about 40° C. to about 160° C., preferably about 80° C. to about 120° C.

Step 1a of Scheme 2a depicts an alternate route to the preparation of a compound of formula XIV by treating the compound of formula XI with the compound of formula II (from Scheme 1) wherein $R^3$ is an optionally substituted aryl or heteroaryl group, in a solvent such as tetrahydrofuran, tert-butylmethyl ether, or 1,4-dioxane, preferably tetrahydrofuran, with an alkali metal amine base, such as sodium bis(trimethylsilylamide), potassium bis(trimethylsilylamide), lithium bis(trimethylsilylamide), or lithium diisopropylamide, or an alkali metal hydride, such as sodium hydride or potassium hydride, preferably sodium bis(trimethylsilylamide).

In Step 2 of Scheme 2a the compound of the formula XV is prepared by treating the compound of the formula XIV with an excess of an alkyl iodide, alkyl methanesulfonate, alkyl arylsulfonate, or alkyl triflate, in a solvent such as acetonitrile or 1,4-dioxane, preferably acetonitrile, at a temperature of about 20° C. to about 150° C., preferably 70° C. to 90° C., for about 10 minutes to about 60 hours, a period of time sufficient to alkylate the pyridine nitrogen, followed by removal of solvent in vacuo, and subsequent addition of a lower alcohol solvent, preferably methanol, followed by the addition of sodium borohydride.

In Step 3 of Scheme 2a a compound of the formula I, wherein $R^1$ is $G^2$ and $R^3$ is H, designated IC' in Scheme 2 is prepared by catalytic reduction of compound XV in a reaction inert solvent such as a lower alcohol, preferably methanol or ethanol, with a noble metal catalyst, such as platinum or palladium, suspended on a solid support, preferably 10% palladium on carbon, under a hydrogen pressure of about 1 atmosphere to about 5 atmospheres, preferably about 3 atmospheres to about 4 atmospheres, at a temperature of about 10° C. to about 100° C., preferably about 40° C. to about 60° C., while shaking the reaction mixture. Alternatively, the double bond may be reduced under transfer hydrogenation conditions where a hydride donor such as cyclohexadiene or ammonium formate is used in place of hydrogen, where ammonium formate is preferred, in a reaction inert solvent such as a lower alcohol, THF, dioxane or ethyl acetate, preferably methanol or ethanol, in the presence of a noble metal catalyst on a solid support such as palladium on carbon (Pd/C), palladium on barium sulfate (Pd/BaSO$_4$), platinum on carbon (Pt/C), or tris(triphenylphosphine) rhodium chloride (Wilkinson's catalyst), preferably about 10% palladium on carbon, at a temperature of about 20° C. to 150° C., preferably 40° C. to 80° C.

Alternatively, the reduction of the carbon-carbon double bond of XV to produce a compound of the formula 1, designated 1C' in Scheme 2a can be accomplished using alternative procedures known to one skilled in the art. Larock, R. C. Comprehensive Organic Transformations. VCN Publishers, 1989.

SCHEME 2A

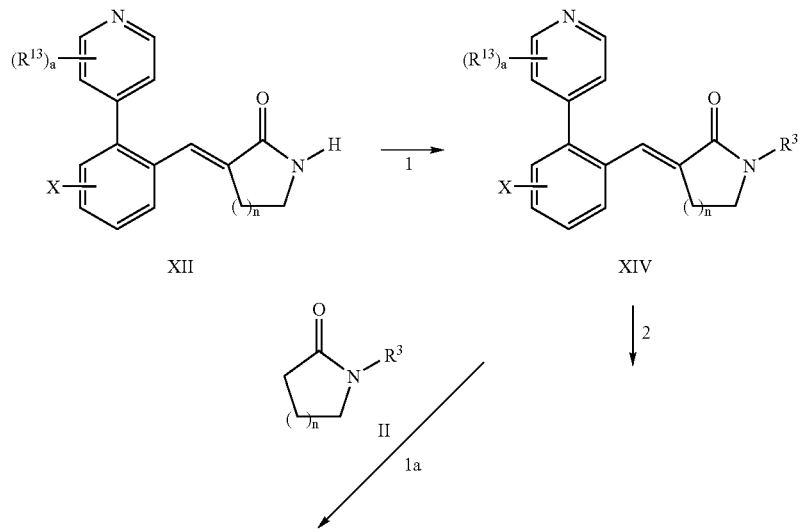

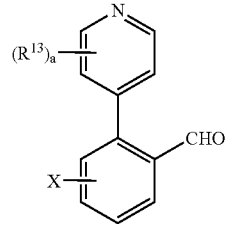

XI

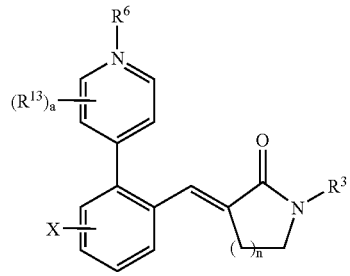

XV

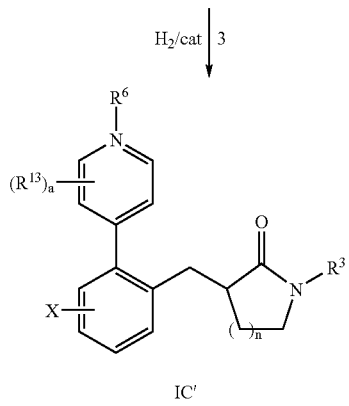

IC'

Scheme 2b depicts yet another route for synthesis of compounds of formula I wherein $R^1$ is $G^2$ and $R^3$ is an optionally substituted aryl or heteroaryl group. In Step 1 of Scheme 2b a compound of the formula XVI wherein $R^1$ is $G^2$ is prepared by catalytic reduction of compound XIV, wherein $R^3$ is an optionally substituted aryl or heteroaryl group, in a reaction inert solvent such as a lower alcohol, preferably methanol or ethanol, with a noble metal catalyst, such as platinum or palladium, suspended on a solid support, preferably 10% palladium on carbon, under a hydrogen pressure of about 1 atmosphere to about 5 atmospheres, preferably about 3 atmospheres to about 4 atmospheres, at a temperature of about 10° C. to about 100° C., preferably about 40° C. to about 60° C., while shaking the reaction mixture. Alternatively, the double bond may be reduced under transfer hydrogenation conditions where a hydride donor such as cyclohexadiene or ammonium formate is used in place of hydrogen, where ammonium formate is preferred, in a reaction inert solvent such as a lower alcohol, THF, dioxane or ethyl acetate, preferably methanol or ethanol, in the presence of a noble metal catalyst on a solid support such as palladium on carbon (Pd/C), palladium on barium sulfate (Pd/BaSO$_4$), platinum on carbon (Pt/C), or tris(triphenylphosphine) rhodium chloride (Wilkinson's catalyst), preferably about 10% palladium on carbon, at a temperature of about 20° C. to 150° C., preferably 40° C. to 80° C.

Alternatively, the reduction of the carbon-carbon double bond of XIV to produce a compound of the formula XVI can be accomplished using alternative procedures known to one skilled in the art. Larock, R. C. 1989.

In Step 2 of Scheme 2b a compound of the formula XVII is prepared by treating the compound of the formula XVI with an excess of an alkyl iodide, alkyl methanesulfonate, alkyl arylsulfonate, or alkyl triflate, in a solvent such as acetonitrile or 1,4-dioxane, preferably acetonitrile, at a temperature of about 20° C. to about 150° C., preferably 70° C. to 90° C., for about 10 minutes to about 60 hours, a period of time sufficient to alkylate the pyridine nitrogen, followed by removal of solvent in vacuo, and subsequent addition of a lower alcohol solvent, preferably methanol, followed by the addition of sodium borohydride.

In Step 3 of Scheme 2b the compound of the formula I, wherein $R^1$ is $G^2$ and $R^3$ is an optionally substituted aryl or heteroaryl group, designated IC' in Scheme 2b, is prepared by catalytic reduction of compound XVII in a reaction inert solvent such as a lower alcohol, preferably methanol or ethanol, with a noble metal catalyst, such as platinum or palladium, suspended on a solid support, preferably 10% palladium on carbon, under a hydrogen pressure of about 1 atmosphere to about 5 atmospheres, preferably about 3 atmospheres to about 4 atmospheres, at a temperature of about 10° C. to about 100° C., preferably about 20° C. to about 50° C., while shaking the reaction mixture. Alternatively, the double bond may be reduced under transfer hydrogenation conditions where a hydride donor such as cyclohexadiene or ammonium formate is used in place of hydrogen, where ammonium formate is preferred, in a reaction inert solvent such as a lower alcohol, THF, dioxane or ethyl acetate, preferably methanol or ethanol, in the presence of a noble metal catalyst on a solid support such as palladium on carbon (Pd/C), palladium on barium sulfate (Pd/BaSO$_4$), platinum on carbon (Pt/C), or tris(triphenylphosphine) rhodium chloride (Wilkinson's catalyst), preferably about 10% palladium on carbon, at a temperature of about 20° C. to 150° C., preferably 40° C. to 80° C.

Alternatively, the reduction of the carbon-carbon double bond of XVII to produce a compound of the formula 1, designated 1C' in Scheme 2b can be accomplished using alternative procedures known to one skilled in the art. Larock, R. C., 1989.

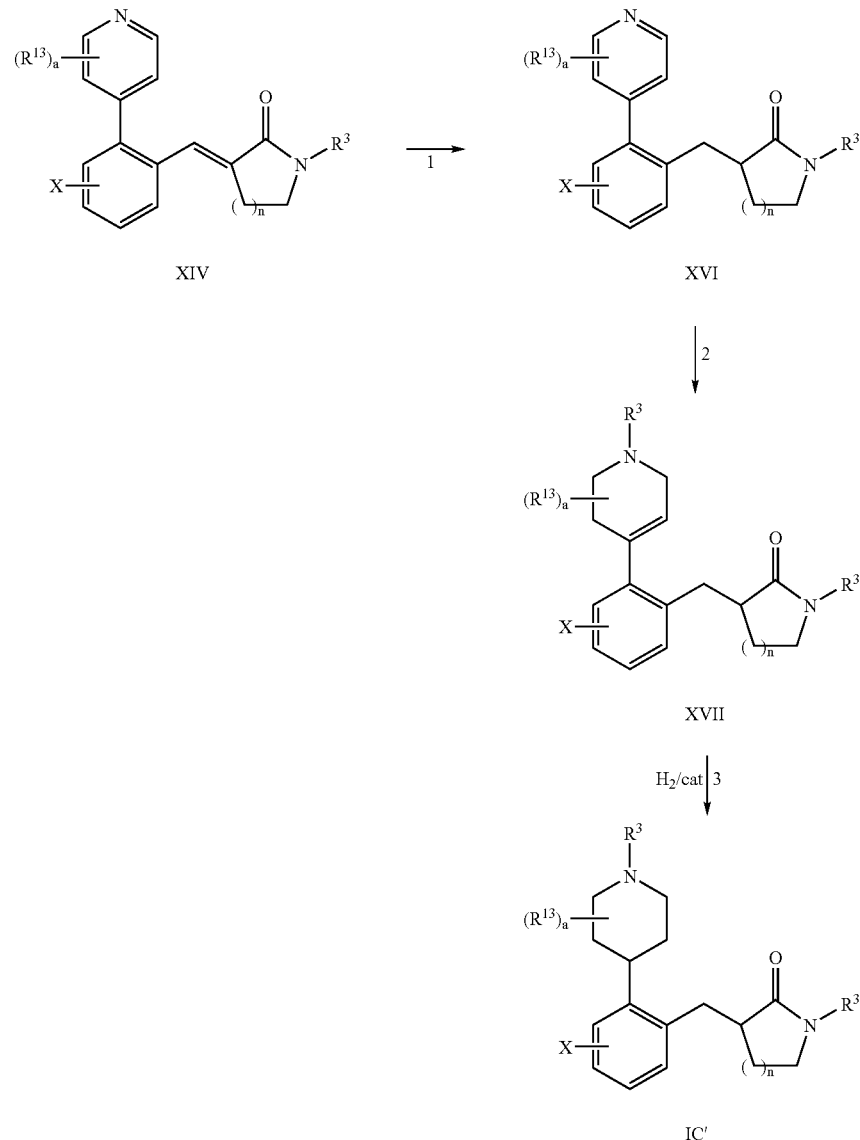

General methods for the preparation of aryl halides used in the N-arylation and N-heteroarylation coupling reactions described herein are given in Murugusan, N. U.S. Pat. No. 5,612,359; Guay, D. et al. *Biorg. Med. Chem. Lett.* 2002, 12, 1457-1461; Sall, D. J. et al. *J. Med. Chem.* 2000, 43, 649-663; Olah, G. A.; Porter, R. D. *J. Amer. Chem. Soc.* 1971, 93, 6877-6887; Brown, H. C. et al. *J. Amer. Chem. Soc.* 1957, 79, 1906-1909; Nenitzescu, C.; Necsoiu, I. *J. Amer. Chem. Soc.* 1950, 72, 3483-3486; Muci, A. R.; Buchwald, S. L. *Top. Curr. Chem.*; Springer-Verlag: Berlin Heidelberg, 2002; Vol. 219, pp. 131-209; Schefczik, E. DE 19650708; Howard, H. R.; Sarges, R. EP 104860; Wang, X et al. *Tetrahedron Lett.,* 2000, 41, 4335-4338 all of which are herein incorporated by reference in their entirety. Those skilled in the art will recognize that, where appropriate, hydroxyl groups on aryl or heteroaryl halides can be etherified by standard methods known in the art such as treatment with an alkali metal hydride or alkali metal hydroxide, such as sodium hydride, potassium hydride, sodium hydroxide, potassium hydroxide, or cesium hydroxide, preferably sodium hydride, in a solvent such as tetrahydrofuran, N,N-dimethylformamide, or dimethylsulfoxide, preferably tetrahydrofuran, at a temperature from about −20 to 50° C., followed by addition of an alkyl halide or tosylate, preferably an alkyl iodide.

The compounds of the formula I and their pharmaceutically acceptable salts (hereafter "the active compounds") can be administered via either the oral, transdermal (e.g., through the use of a patch), intranasal, sublingual, rectal, parenteral or topical routes. Transdermal and oral administration are preferred. These compounds are, most desirably, administered in dosages ranging from about 0.25 mg up to about 1500 mg per day, preferably from about 0.25 to about 300 mg per day in single or divided doses, although variations will necessarily occur depending upon the weight and condition of the subject being treated and the particular route of administration chosen. However, a dosage level that is in the range of about 0.01 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds can be administered alone or in combination with pharmaceutically acceptable carriers or diluents by any of the several routes previously indicated. More particularly, the active compounds can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tableting purposes. Solid compositions of a similar type may also be employed as fillers in gelatin capsules; preferred materials in this connection also include lactose or milk sugar] as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active compound in either sesame or peanut oil or in aqueous propylene glycol can be employed. The aqueous solutions should be suitably buffered (preferably pH greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active compounds topically and this can be done by way of creams, a patch, jellies, gels, pastes, ointments and the like, in accordance with standard pharmaceutical practice.

Bioloclical Assay

All tested compounds had $IC_{50}$ values of 1000 nM or less. The activity of the compounds of the present invention with respect to $5HT_{1B}$ (formerly $5HT_{1D}$) binding ability can be determined using standard radioligand binding assays as described in the literature. The $5\text{-}HT_{1A}$ affinity can be measured using the procedure of Hoyer et al. (*Brain Res.*, 376; 85 (1986)). The $5\text{-}HT_{1D}$ affinity can be measured using the procedure of Heuring and Peroutka (*J. Neurosci.*, 7, 894 (1987)).

The in vitro activity of the compounds of the present invention at the $5\text{-}HT_{1D}$ binding site may be determined according to the following procedure. Bovine caudate tissue is homogenized and suspended in 20 volumes of a buffer containing 50 mM TRIS.hydrochloride (tris[hydroxymethyl]aminomethane hydrochloride) at a pH of 7.7. The homogenate is then centrifuged at 45,000 G for 10 minutes. The supernatant is then discarded and the resulting pellet resuspended in approximately 20 volumes of 50 mM TRIS.hydrochloride buffer at pH 7.7. This suspension is then pre-incubated for 15 minutes at 37° C., after which the suspension is centrifuged again at 45,000 G for 10 minutes and the supernatant discarded. The resulting pellet (approximately 1 gram) is resuspended in 150 ml of a buffer of 15 mM TRIS.hydrochloride containing 0.01 percent ascorbic acid with a final pH of 7.7 and also containing 10 μM pargyline and 4 mM calcium chloride ($CaCl_2$). The suspension is kept on ice at least 30 minutes prior to use.

The inhibitor, control or vehicle is then incubated according to the following procedure. To 50 μl of a 20 percent dimethylsulfoxide (DMSO)/80 percent distilled water solution is added 200 μl of tritiated 5-hydroxytryptamine (2 nM) in a buffer of 50 mM TRIS.hydrochloride containing 0.01 percent ascorbic acid at pH 7.7 and also containing 10 μM pargyline and 4 μM calcium chloride, plus 100 nM of 8-hydroxy-DPAT (dipropylaminotetraline) and 100 nM of mesulergine. To this mixture is added 750 μl of bovine caudate tissue, and the resulting suspension is vortexed to ensure a homogenous suspension. The suspension is then incubated in a shaking water bath for 30 minutes at 25° C. After incubation is complete, the suspension is filtered using glass fiber filters (e.g., Whatman GF/BTM filters.). The pellet is then washed three times with 4 ml of a buffer of 50 mM TRIS.hydrochloride at pH 7.7. The pellet is then placed in a scintillation vial with 5 ml of scintillation fluid (Aquasol 2™) and allowed to sit overnight. The percent inhibition can be calculated for each dose of the compound. An $IC_{50}$ value can then be calculated from the percent inhibition values.

The activity of the compounds of the present invention for $5\text{-}HT_{1A}$ binding ability can be determined according to the following procedure. Rat brain cortex tissue is homogenized and divided into samples of 1 gram lots and diluted with 10 volumes of 0.32 M sucrose solution. The suspension is then centrifuged at 900G for 10 minutes and the supernate separated and recentrifuged at 70,000 G for 15 minutes. The supernate is discarded and the pellet re-suspended in 10 volumes of 15 mM TRIS.hydrochloride at pH 7.5. The suspension is allowed to incubate for 15 minutes at 37° C. After pre-incubation is complete, the suspension is centrifuged at 70,000 G for 15 minutes and the supernate discarded. The resulting tissue pellet is resuspended in a buffer of 50 mM TRIS.hydrochloride at pH 7.7 containing 4 mM of calcium chloride and 0.01 percent ascorbic acid. The tissue is stored at −70° C. until ready for an experiment. The tissue can be thawed immediately prior to use, diluted with 10 μm pargyline and kept on ice.

The tissue is then incubated according to the following procedure. Fifty microliters of control, inhibitor, or vehicle (1 percent DMSO final concentration) is prepared at various dosages. To this solution is added 200 µl of tritiated DPAT at a concentration of 1.5 nM in a buffer of 50 mM TRIS.hydrochloride at pH 7.7 containing 4 mM calcium chloride, 0.01 percent ascorbic acid and pargyline. To this solution is then added 750 µl of tissue and the resulting suspension is vortexed to ensure homogeneity. The suspension is then incubated in a shaking water bath for 30 minutes at 37° C. The solution is then filtered, washed twice with 4 ml of 10 mM TRIS.hydrochloride at pH 7.5 containing 154 mM of sodium chloride. The percent inhibition is calculated for each dose of the compound, control or vehicle. $IC_{50}$ values are calculated from the percent inhibition values.

The agonist and antagonist activities of the compounds of the invention at $5-HT_{1A}$ and $5-HT_{1D}$ receptors can be determined using a single saturating concentration according to the following procedure. Male Hartley guinea pigs are decapitated and $5-HT_{1A}$ receptors are dissected out of the hippocampus, while $5-HT_{1D}$ receptors are obtained by slicing at 350 mM on a McIlwain tissue chopper and dissecting out the substantia nigra from the appropriate slices. The individual tissues are homogenized in 5 mM HEPES buffer containing 1 mM EGTA (pH 7.5) using a hand-held glass-Teflon® homogenizer and centrifuged at 35,000 xg for 10 minutes at 4° C. The pellets are resuspended in 100 mM HEPES buffer containing 1 mM EGTA (pH 7.5) to a final protein concentration of 20 mg (hippocampus) or 5 mg (substantia nigra) of protein per tube. The following agents are added so that the reaction mix in each tube contained 2.0 mM $MgCl_2$, 0.5 mM ATP, 1.0 mM cAMP, 0.5 mM IBMX, 10 mM phosphocreatine, 0.31 mg/mL creatine phosphokinase, 100 µM GTP and 0.5-1 microcuries of $[^{32}P]$-ATP (30 Ci/mmol: NEG-003—New England Nuclear). Incubation is initiated by the addition of tissue to siliconized microfuge tubes (in triplicate) at 30° C. for 15 minutes. Each tube receives 20 µL tissue, 10 µL drug or buffer (at 10× final concentration), 10 µL 32 nM agonist or buffer (at 10× final concentration), 20 µL forskolin (3 µM final concentration) and 40 µL of the preceding reaction mix. Incubation is terminated by the addition of 100 µL 2% SDS, 1.3 mM cAMP, 45 mM ATP solution containing 40,000 dpm $[^3H]$-cAMP (30 Ci/mmol: NET-275—New England Nuclear) to monitor the recovery of cAMP from the columns. The separation of $[^{32}P]$-ATP and $[^{32}P]$-cAMP is accomplished using the method of Salomon et al., Analytical Biochemistry, 1974, 58, 541-548. Radioactivity is quantified by liquid scintillation counting. Maximal inhibition is defined by 10 µM (R)-8-OH-DPAT for $5-HT_{1A}$ receptors, and 320 nM 5-HT for $5-HT_{1D}$ receptors. Percent inhibitions by the test compounds are then calculated in relation to the inhibitory effect of (R)-8-OH-DPAT for $5-HT_{1A}$ receptors or 5-HT for $5-HT_{1D}$ receptors. The reversal of agonist induced inhibition of forskolin-stimulated adenylate cyclase activity is calculated in relation to the 32 nM agonist effect.

The in vitro activity of the compounds in the present invention at the human ether-a-go-go-related gene potassium channel (hERG) can be determined according to the following procedure. HEK-293 cells expressing the human ERG channel are grown according to standard cell culture techniques. Cells are collected, spun down and the resulting pellet is frozen for future use. On the day of the experiment, frozen cell pellet is weighed (100 mg per 96 well assay plate) and homogenized in 20 volumes of cold 50 mM Tris base containing 10 mM KCl and 1 mM MgCl2 (pH to 7.4 at 4 degrees C.). The homogenate is then centrifuged at 45,000 G for 10 minutes. The supernatant is decanted and the membrane pellet resuspended by Polytron in cold 50 mM Tris base containing 10 mM KCl and 1 mM $MgCl_2$ (pH to 7.4 at 4 degrees C.) to a 20 mg/mL concentration. PVT WGA SPA beads (PEI treated type A) are weighed out and added to diluted tissue, also to concentration of 20 mg/mL. The membrane/bead solution is then gently rotated (speed 2, high) in a cold room (4° C.) for 2 hours on a Roto-Torque (Cole-Palmer Model 7637). Following this preincubation, the bead slurry is then centrifuged at 1000 rpm for 5 min at 4° C. The supernatant is decanted and the pellet is resuspended to 5 mg/ml membrane and bead concentration in 50 mM Tris base containing 10 mM KCl and 1 mM MgCl2 (pH to 7.4 at 22 degrees C)). The resuspended SPA beads/membrane mixture is immediately used in the assay. Beads and membranes are used at a final concentration of 1 mg/well and 25 microgram protein/well, respectively. Dilutions of compounds are made in 10% DMSO/50 mM Tris buffer (pH 7.4) (at 10× final concentration —so that the final DMSO concentration is 1%). To 96 well SPA plates containing drug dilutions, radioligand is added (5 nM final concentration 3H-dofetilide). The incubation is initiated by the addition of tissue/bead slurry. Assay plates incubate for one hour and then radioactivity is quantified using a MicroBeta scintillation counter. The percent inhibition of specific binding can then be calculated.

The compounds of the invention can be tested for in vivo activity for antagonism of $5-HT_{1D}$ agonist-induced hypothermia in guinea pigs according to the following procedure.

Male Hartley guinea pigs from Charles River, weighing 250-275 grams on arrival and 300-600 grams at testing, serve as subjects in the experiment. The guinea pigs are housed under standard laboratory conditions on a 7 a.m. to 7 p.m. lighting schedule for at least seven days prior to experimentation. Food and water are available ad libitum until the time of testing.

The compounds of the invention can be administered as solutions in a volume of 1 ml/kg. The vehicle used is varied depending on compound solubility. Test compounds are typically administered either sixty minutes orally (p.o.) or 0 minutes subcutaneously (s.c.) prior to a $5-HT_{1D}$ agonist, such as [3-(1-methylpyrrolidin-2-ylmethyl)-1H-indol-5-yl]-(3-nitropyridin-3-yl)-amine, which can be prepared as described in PCT publication WO93/11106, published Jun. 10, 1993 which is administered at a dose of 5.6 mg/kg, s.c. Before a first temperature reading is taken, each guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional −30 minute reading is taken. The $5-HT_{1D}$ agonist is then administered at 0 minutes and temperatures are taken 30, 60, 120 and 240 minutes later. In subcutaneous screening experiments, a pre-drug baseline temperature reading is made at −30 minutes. The test compound and $5-HT_{1D}$ agonists are given concurrently and temperatures are taken at 30, 60, 120 and 240 minutes later.

Data are analyzed with two-way analysis of variants with repeated measures in Newman-Keuls post hoc analysis.

The active compounds of the invention can be evaluated as anti-migraine agents by testing the extent to which they mimic sumatriptan in contracting the dog isolated saphenous vein strip (P. Humphrey et al., *Br. J. Pharmacol.*, 94, 1128 (1988)). This effect can be blocked by methiothepin, a known serotonin antagonist. Sumatriptan is known to be useful in the treatment of migraine and produces a selective increase in carotid vascular resistance in the anesthetized dog. The pharmacological basis of sumatriptan efficacy has been discussed in W. Fenwick et al., *Br. J. PharmacoL*, 96, 83 (1989).

The serotonin 5-HT$_1$ agonist activity can be determined by the in vitro receptor binding assays, as described for the 5-HT$_{1A}$ receptor using rat cortex as the receptor source and [$^3$H]-8-OH-DPAT as the radioligand (D. Hoyer et al., *Eur. J. Pharm.*, 118, 13 (1985)) and as described for the 5-HT$_{1D}$ receptor using bovine caudate as the receptor source and [$^3$H]serotonin as the radioligand (R. E. Heuring and S. J. Peroutka, *J. Neuroscience*, 7, 894 (1987)).

The following experimental preparations and examples illustrate, but do not limit the scope of, this invention.

Preparation 1

2-(4-methylpiperazinyl)-benzaldehyde

A solution of 1-methylpiperazine (139.5 mL, 1.26 moles), potassium carbonate (145 g, 1.05 moles), and 2-fluorobenzaldehyde (73.7 mL, 0.7 moles) in water (700 mL) was heated at reflux for 18 hours. The solution was cooled to room temperature, extracted with methylene chloride (2×700 mL), and the combined organic layers were washed with water (2×700 mL). The organic layer was dried (MgSO$_4$), filtered, and the solvent was removed in vacuo to afford 140 g of a dark oil. 1H NMR (400 MHz, CDCl3) 7.79 (dd, J=1.2, 7.9 Hz, 1H), 7.52 (td, J=1.5, 7.5 Hz, 1H), 7.11 (m, 2H), 3.12 (t, J=4.8 Hz, 4H), 2.63 (brs, 4H), 2.39 (s, 3H); 13C NMR (100 MHz, CDCl3) 191.6, 155.8, 135.2, 130.0, 128.9, 122.8, 119.2, 55.3, 54.1, 46.3.

Preparation 2

2-(4-Benzyl-piperazin-1-yl)-benzaldehyde

The title compound was prepared using the method analogous to that used for Preparation 1. 13C NMR (100 MHz, CDCl3) 191.7, 156.0138.1, 135.2, 129.9, 129.5, 128.9, 128.6, 127.5, 122.8, 119.2; MS (AP/Cl) 281.2 (M+H)+.

Preparation 3

5-Methoxy-2-(4-methyl-piperazin-1-yl)-benzaldehyde

The title compound was prepared using the method analogous to that used for Preparation 1. 1H NMR (400 MHz, CDCl3) 2.36 (s, 3H), 2.61 (brs, 1h), 3.03 (m, 4Hz), 3.78 (s, 3H), 7.06-7.12 (m, 2H), 7.28 (m, 2H), 10.37 (s, 1H).

Preparation 4

2-(2,5-Dimethyl-piperazin-1-yl)-benzaldehyde

The title compound was prepared using the method analogous to that used for Preparation 1. 1H NMR (400 MHz, CDCl3) 1H NMR (400 MHz, CDCl3) 0.83 (d, 1H, J=5.8 Hz), 1.04 (d, 1H, J=6.6Hz), 2.20-2.30 (brs, 1H), 2.52 (dd, 1H, J=11.6 and 10.0 Hz), 2.72 (dd, 1H, J=13.2 and 10.8Hz), 2.89 (dd, 1H, J=11.6 and 2.8 Hz), 3.05-3.64 (m, 3H), 7.21-7.27 (m, 1H), 7.33 (d, 1H, J=5.5 Hz), 7.56-7.60 (m, 1H), 7.84 (dd, 1H, J=8.0 and 1.6 Hz), 10.6 (s, 1H); MS (AP/Cl) 219.2 (M+H)+.

Preparation 5

5-Fluoro-2-(4-methyl-piperazin-1-yl)-benzaldehyde

The title compound was prepared using the method analogous to that used for Preparation 1. 1H NMR (400 MHz, CDCl3) 2.35 (s, 3H), 2.55-2.65 (m, 4H), 3.00-3.10 (m, 4H), 7.11 (d, 1H, J=9.2 and 4.8 Hz), 7.19-7.25 (m, 1H), 7.46 (d, 1H, J=8.8 and 3.6 Hz); 10.38 (s, 1H).

Preparation 6

2-Fluoro-6-(4-methyl-piperazin-1-yl)-benzaldehyde

The title compound was prepared using the method analogous to that used for Preparation 1. 1H NMR (400 MHz, CDCl3) 2.37 (s, 3H), 2.62-2.64 (m, 4H), 3.11-3.14 (m, 4H), 6.74 (dd, 1H, J=10.4 and 8.4 Hz), 6.84 (d, 1H, J=8.4 Hz), 7.41-7.46 (m, 1H), 10.25 (s, 1H); MS (AP/Cl) 223.3 (M+H)+.

Preparation 7

5-Methyl-2-(4-methyl-piperazin-1-yl)-benzaldehyde

The title compound was prepared using the method analogous to that used for Preparation 1. 1H NMR (400 MHz, CDCl3) 2.32 (s, 3H), 2.38 (s, 3H), 2.55-2.65 (m, 4H), 3.05-3.09 (m, 4H), 7.04 (d, 1H, J=8.0 Hz), 7.32-7.34 (m, 1H), 7.61 (d, 1H, J=2.0 Hz) 10.30 (s, 1H); MS (AP/Cl) 219.2 (M+H)+.

Preparation 8

2-(3,5-Dimethyl-piperazin-1-yl)-benzaldehyde

The title compound was prepared using the method analogous to that used for Preparation 1. 1H NMR (400 MHz, CDCl3) 1.09 (d, 6H, J=6.4 Hz), 2.51 (t, 2H, J=11.2 Hz), 3.10-3.18 (m, 4H), 7.08 (dd, 1H, J=3.2 and 0.8 Hz), 7.48-7.51 (m, 1H), 7.78 (d, 1H, J=8.0 and 2.0 Hz), 10.30 (s, 1H); MS (AP/Cl) 219.2 (M+H)+.

Preparation 9

2-(3,4,5-Trimethyl-piperazin-1-yl)-benzaldehyde

The title compound was prepared using the method analogous to that used for Preparation 1. 1H NMR (400 MHz, CDCl3) 1.12 (d, 6H, J=6.4 Hz), 2.33 (s, 3H), 2.46-2.51 (m, 2H), 2.79 (dd, 2H, J=10.8 and 11.6 Hz), 3.06-3.09 (m, 2H), 7.07-7.11 (m, 1H), 7.48-7.53 (m, 1H), 7.78 (dd, 1H, J=7.6 and 1.6 Hz), 10.32 (s, 1H).

Preparation 10

2-(4-Methyl-[1,4]diazepan-1-yl)-benzaldehyde

The title compound was prepared using the method analogous to that used for Preparation 1. 1H NMR (400 MHz, CDCl3) 1.95 (p, 5.6 Hz, 2H), 2.38 (s, 3H), 2.67 (t, J=5.4 Hz, 2H), 2.73 (d, J=4.8 Hz, 2H), 3.45 (t, J=5.8 Hz, 2H), 3.50-3.52 (m, 2H), 6.92 (t, J=7.3 Hz, 1H), 7.02 (d, J=8.3 Hz, 1H), 7.39 (dt, J=7.1, 1.7 Hz, 1H), 7.70 (dd, J=7.9, 1.7 Hz, 1H), 10.15 (s, 1H).

Preparation 11

2-(4-Ethyl-piperazin-1-yl)-benzaldehyde

The title compound was prepared using the method analogous to that used for Preparation 1. 1H NMR (400 MHz, CDCl3) 1.11 (t, J=7.3 Hz, 3H), 2.59 (q, J=7.2 Hz, 2H), 2.65 (br s, 4H), 3.12 (t, J=4.8 Hz, 4H), 7.06-7.10 (m, 2H), 7.50 (dt, J=7.7, 1.7 Hz, 1H), 7.77 (dd, J=8.3, 1.9 Hz, 1H), 10.29 (s, 1H).

Preparation 12: General Aldol Procedure 1

3-[5-Fluoro-2-(4-methyl-piperazin-1-yl)-benzylidenel-pyrrolidin-2-one

A solution of 9.0 g (40.5 mmol) of 5-Fluoro-2-(4-methyl-piperazin-1-yl)-benzaldehyde and 5.1 g (40.5 mmol) of N-acetylpyrrolidinone in 80 mL of tetrahydrofuran is slowly added to a 0° C. solution of 5.4 g (133.6 mmol) of sodium hydride in 80 mL of tetrahydrofuran over a 2 hour period. After 2.5 hour at 0° C., the reaction is quenched with sat. ammonium chloride and extracted with methylene chloride. The organic layer is dried with magnesium sulfate and concentrated to provide a yellow solid. Recrystallization from ethyl acetate and diisopropyl ether provided 3.92 g (33%) of 3-[5-Fluoro-2-(4-methyl-piperazin-1-yl)-benzylidene]-pyrrolidin-2-one as a white solid. Diagnostic C13 NMR (100 MHz, CDCl3) 26.4, 39.9, 46.1, 52.9, 55.3, 115.2, 115.5, 115.8, 116.0, 120.2, 120.3, 126.7, 131.1, 148.9, 157.3, 159.7, 172.8; MS m/z 290.3 (M+1).

Preparation 13: General Aldol Procedure 2

3-[2-(4-methyl-piperazin-1-yl)-benzylidenel-pyrrolidin-2-one

To a solution of 1.0 M NaHMDS in anhydrous THF (30 mL, 30 mmol) at 0° C. under $N_2$ was added via an addition funnel a mixture of aldehyde from preparation 1 (2.02 g, 9.90 mmol) and pyrrolidinone II (R3=tert-butyl) (5.02 g, 29.6 mmol) in anhydrous THF (20 mL+5 mL rinse). After the addition was complete, the reaction mixture was warmed to room temperature and stirred at ambient temperature for 18 hours. Water (30 mL) was added to the reaction mixture. The mixture was extracted with $CH_2Cl_2$ (30 mL). The aqueous phase was extracted with additional $CH_2Cl_2$ (2×20 mL). The combined organic extracts were washed with brine, dried ($Na_2SO_4$) and concentrated to give a brown solid. The solid was triturated with ethyl acetate and hexanes for 3 hours then filtered to yield the desired product as beige solids (2.54 g, 95%). 13C NMR (100 MHz, CDCl3) 173.3, 152.1, 129.7, 129.0, 128.0, 122.5, 118.9, 55.4, 52.5, 46.2, 39.9, 26.6; MS (AP/Cl) 272.2 (M+H)+.

Preparation 14

3-[2-(4-Benzyl-piperazin-1-yl)-benzylidenel-pyrrolidin-2-one

The title compound was prepared in a procedure analogous to that described in Preparation 13. 13C NMR (100 MHz, CDCl3) d 173.3, 152.8, 138.4, 129.7, 129.63, 129.57, 129.0, 128.5, 128.0, 127.3, 122.3, 118.8, 63.3, 53.6, 52.7, 40.0, 26.6; MS (AP/Cl) 348.1 (M+H)+.

Preparation 15

3-[5-Methoxy-2-(4-methyl-pirerazin-1-yl)-benzylidenel-pyrrolidin-2-one

The title compound was prepared in a procedure analogous to that described in Preparation 13. 13C NMR (100 MHz, CDCl3) d 26.5, 40.0, 46.2, 53.0, 55.5, 55.7, 114.1, 114.9, 120.0, 127.5, 130.3, 131.2, 146.5, 155.1, 173.1; MS (AP/Cl) 302.3 (M+H)+.

Preparation 16

3-[2-(4-Methyl-piperazin-1-yl)-benzylidenel-piperidin-2-one

The title compound was prepared in a procedure analogous to that described in Preparation 13. 13C NMR (100 MHz, CDCl3) d 23.3, 26.6, 42.4, 46.2, 52.2, 55.5, 118.2, 121.8, 128.4, 129.3, 129.4, 130.3, 134.3, 152.4, 167.2; MS (AP/Cl) 286.3 (M+H)+.

Preparation 17

3-[2-(2,5-Dimethyl-Piperazin-1-yl)-benzylidenel-pyrrolidin-2-one

The title compound was prepared in a procedure analogous to that described in Preparation 13. 13C NMR (100 MHz, CDCl3) d 17.5, 19.6, 26.6, 40.0, 51.1, 53.8, 53.9, 63.8, 123.4, 124.3, 127.3, 128.9, 129.2, 130.4, 133.6, 151.6, 173.4; MS (AP/Cl) 286.3 (M+H)+.

Preparation 18

3-[5-Fluoro-2-(4-methyl-piperazin-1-yl)-benzylidenel-piperidin-2-one

The title compound was prepared in a procedure analogous to that described in Preparation 13. 13C NMR (100 MHz, CDCl3) d 23.3, 26.5, 42.4, 46.2, 52.5, 55.5, 115.4, 115.6, 116.6, 116.8, 119.5, 119.6, 129.4, 131.2, 131.2, 133.1, 148.7, 159.1, 166.7; MS (AP/Cl) 304.2 (M+H)+.

Preparation 19

3-[2-Fluoro-6-(4-methyl-piperazin-1-yl)-benzylidenel-pyrrolidin-2-one

The title compound was prepared in a procedure analogous to that described in Preparation 13. 13C NMR (100 MHz, CDCl3) d 25.2, 27.3, 40.7, 41.4, 46.2, 53.0, 55.7, 111.5, 111.7, 116.6, 116.6, 123.0, 123.2, 127.8, 127.9, 153.8, 153.9, 160.9, 163.4, 180.7; MS (AP/Cl) 292.3 (M+H)+.

Preparation 20

3-[2-(3,4,5-Trimethyl-piperazin-1-yl)-benzylidene]-pyrrolidin-2-one

The title compound was prepared in a procedure analogous to that described in Preparation 13. 13C NMR (100 MHz, CDCl3) d 18.3, 26.6, 29.9, 38.0, 39.9, 58.1, 60.2, 118.8, 122.4, 127.8, 129.0, 129.6, 152.2, 173.1.

Preparation 21

3-[5-Methyl-2-(4-methyl-piperazin-1-yl)-benzylidenel-pyrrolidin-2-one

The title compound was prepared in a procedure analogous to that described in Preparation 13. 13C NMR (100 MHz, CDCl3) d 23.0, 26.6, 39.9, 46.1, 52.7, 55.4, 118.8, 128.0, 129.3, 129.5, 129.6, 130.2, 131.8, 150.4, 173.0; MS (AP/Cl) 286.3 (M+H)+.

PreParation 22

3-[2-(4-Methyl-[1,4]diazepan-1-yl)-benzylidenel-pyrrolidin-2-one

The title compound was prepared in a procedure analogous to that described in Preparation 13. 1H NMR (400 MHz, CDCl3) 1.93 (p, J=5.9 Hz, 2H), 2.41 (s, 3H), 2.72-2.76 (m, 4H), 3.03 (dt, J=6.6, 2.8 Hz, 2H), 3.22-3.30 (m, 4H), 3.49 (t, J=6.4 Hz, 2H), 6.44 (s, 1H), 6.95 (t, J=7.5 Hz, 1H), 7.05 (dd, J=7.9, 1.0 Hz, 1H), 7.20-7.24 (m, 1H), 7.35 (dd, J=7.9, 1.2 Hz, 1H), 7.60 (t, J=2.9 Hz, 1H); MS (AP/Cl) 286.2 (M+H)+.

Preparation 23

3-[2-(4-Ethyl-piperazin-1-yl)-benzylidenel-pyrrolidin-2-one

The title compound was prepared in a procedure analogous to that described in Preparation 13. 1H NMR (400 MHz, CDCl3) 1.09 (t, J=7.1 Hz, 3H), 2.48 (q, J=7.2 Hz, 2H), 2.64 (br s, 4H), 2.98 (t, J=4.6 Hz, 4H), 3.07-3.11 (m, 2H), 3.49 (t, J=6.6 Hz, 2H), 6.50 (br s, 1H), 7.00-7.04 (m, 2H), 7.27 (t, J=8.5 Hz, 1H), 7.38 (d, J=7.9 Hz, 1H), 7.62 (t, J=2.7 Hz, 1H); MS (AP/Cl) 286.2 (M+H)+.

Preparation 24

3-[5-Fluoro-2-(4-methyl-piperazin-1-yl)-benzyl]-pyrrolidin-2-one

To a solution of 3.9 g (13.5 mmol) of 3-[5-Fluoro-2-(4-methyl-piperazin-1-yl)-benzylidene]-pyrrolidin-2-one in 150 mL of methanol is added 1.0 g of Pd/C. Hydrogenation at 50 psi with heating to 50° C. was complete after 24 hours. The reaction was filtered over Celite™ using methanol and concentrated. The resultant residue was purified by silica gel chromatography to provide 3.8 g (98% yield) of 3-[5-Fluoro-2-(4-methyl-piperazin-1-yl)-benzyl]-pyrrolidin-2-one. Diagnostic C13 NMR (100 MHz, CDCl3) 27.3, 31.7, 40.5, 42.1, 46.2, 53.0, 55.8, 113.7, 113.9, 116.6, 116.8, 122.3, 122.4, 137.9, 148.0, 161.0; MS m/z 292.2 (M+1).

Preparation 25

3-[2-(4-methyl-piperazin-1-yl)-benzyl]-pyrrolidin-2-one

A round bottom flask under $N_2$ was charged with 10% Pd/C (0.99 g) and ethyl alcohol (50 mL) followed by 3-[2-(4-methylpiperazin-1-yl)-benzylidene]-pyrrolidin-2-one (3.00 g, 11.1 mmol) and ammonium formate (6.97 g, 110.6 mmol). The reaction mixture was stirred at room temperature for 1 hour then heated to 50° C. for 3 hours. The reaction mixture was cooled to room temperature and filtered through Celite™ under $N_2$. The Celite™ pad was washed with ethyl alcohol (25 mL) and water (10 mL). The filtrate was evaporated to give white solids which were partitioned between ethyl acetate (25 mL) and $H_2O$ (10 mL). The aqueous layer was extracted with additional ethyl acetate (2×25 mL). The combined organic extracts were washed with brine, dried ($Na_2SO_4$) and concentrated to a white solid (2.90 g, 96%). The material could be used crude or triturated with ethyl acetate (5 vol) to give 80% recovery of improved purity of the title compound. 13C NMR (100 MHz, CDCl3) d 180.6, 152.1, 135.5, 130.4, 127.5, 124.5, 120.8, 55.9, 52.9, 46.4, 42.4, 40.6, 31.8, 27.3; MS (AP/Cl) 274.3 (M+H)+.

Preparation 26-34

3-[5-Methoxy-2-(4-methyl-piperazin-1-yl)-benzyl]-pyrrolidin-2-one
3-[2-(4-Methyl-piperazin-1-yl)-benzyl]-piperidin-2-one
3-[2-(2,5-Dimethyl-piperazin-1-yl)-benzyl]-pyrrolidin-2-one
3-[5-Fluoro-2-(4-methyl-piperazin-1-yl)-benzyl]-piperidin-2-one
3-[2-Fluoro-6-(4-methyl-piperazin-1-yl)-benzyl]-pyrrolidin-2-one
3-[5-Methyl-2-(4-methyl-piperazin-1-yl)-benzyl]-pyrrolidin-2-one
3-[2-(3,4,5-Trimethyl-piperazin-1-yl)-benzyl]-pyrrolidin-2-one
3-[2-(4-Methyl-[1,4]diazepan-1-yl)-benzyl]-pyrrolidin-2-one
3-[2-(4-Ethyl-piperazin-1-yl)-benzyl]-pyrrolidin-2-one The title compounds were prepared in a procedure analogous to that described in Preparation 25.

Preparation 35

3-(2-Piperazin-1-yl-benzyl)-pyrrolidin-2-one

A suspension of 3-[2-(4-benzyl-piperazin-1-yl)-benzylidene]-pyrrolidin-2-one (Preparation 15, 6.3 g, 18 mmol) and 10% palladium on carbon (1.5 g) in methanol (100 mL) was placed under a hydrogen atmosphere (50 psi) and was heated at 50° C. for 24 hours. The mixture was filtered through Celite™, fresh 10% palladium on carbon was added (2.0 g), and the mixture was placed under hydrogen (50 psi) and was heated at 60° C. for 7 hours. The mixture was filtered through Celite™, the solvent was removed in vacuo and the residue was purified by silica gel chromatography (20:1 chloroform-methanol w/1% ammonium hydroxide) to give 3.8 g (82% yield) of the title compound. 13C NMR (100 MHz, CDCl3) 180.7, 152.6, 135.5, 130.4, 127.5, 124.5, 120.8, 54.3, 46.8, 42.4, 40.7, 31.9, 27.3; MS (AP/Cl) 260.1 (M+H)+.

Preparation 36

2-(4-Bromo-Phenyl)-propan-2-ol

A solution of methyl p-bromobenzoate (3 g, 13.2 mmol) in tetrahydrofuran (14 mL) cooled to −30° C. was treated dropwise with methyl magnesium bromide (1 M in diethyl ether, 105.5 mmol, 105.5 mL). Upon completion of addition, the resulting suspension was allowed to warm to room temperature and was stirred for 5 hours. Saturated aqueous ammonium chloride (100 mL) was added slowly and the mixture was diluted with ethyl acetate (100 mL). The organic and aqueous layers were separated and the aqueous layer was extracted with ethyl acetate (3×50 mL). The combined organic layers were dried over magnesium sulfate, were filtered, and the solvent was removed in vacuo. Purification by silica gel chromatography (10:1 hexanes—ethyl acetate) gave 2.2 g (79% yield) of 2-(4-bromo-phenyl)-propan-2-ol. 13C NMR (100 MHz, CDCl3) d 148.4, 131.4, 126.6, 120.8, 72.5, 31.9; MS (AP/Cl) 197.1, 199.1 (M+H)+.

Preparations 37-40

2-(3-Bromo-phenyl)-propan-2-ol
1-(4-Bromo-phenyl)-2-methyl-propan-2-ol
2-(5-Bromo-pyridin-2-yl)-propan-2-ol
3-(5-Bromo-pyridin-2-yl)-pentan-3-ol The title compounds were prepared using methyl-3-bromobenzoate, methyl-4-bromophenyl acetate, ethyl-5-bromo-2-carboxypyridine or ethyl-5-bromo-2-carboxypyridine and ethyl magnesium bromide with methylene chloride as solvent, respectively, but otherwise followed the procedure detailed for Preparation 36.

Preparation 41

1-(5-Bromo-pyridin-2-yl)-cyclopentanol

The title compound was prepared using ethyl-5-bromo-2-carboxypyridine, 1,4-bis (bromomagnesium) butane and diethyl ether as solvent, but otherwise followed the general procedure for Preparation 36. 13C NMR (100 MHz, CDCl3) d 164.1, 148.9, 139.5, 120.9, 118.8, 83.2, 42.7, 24.9; MS (AP/Cl) 242.1, 244.1 (M+H)+.

Preparation 42

2-(6-Bromo-pyridin-3-yl)-propan-2-ol

The title compound was prepared using ethyl 5-bromo-2-carboxypyridine, but otherwise followed the general procedure for Preparation 36. 13C NMR (100 MHz, CDCl3) d 147.2, 144.1, 140.4, 135.8, 127.8, 21.3, 31.9; MS (AP/Cl) 216.2, 218.2 (M+H)+.

Preparation 43

1-(6-Bromo-pyridin-3-yl)-cyclopentanol

The title compound was prepared using ethyl 5-bromo-2-carboxypyridine, 1,4-bis (bromomagnesium) butane and diethyl ether as solvent, but otherwise followed the general procedure for Preparation 36. 13C NMR (100 MHz, CDCl3) d 147.5, 142.2, 140.3, 136.4, 127.8, 81.8, 42.3, 24.0; MS (AP/Cl) 242.2, 244.2 (M+H)+.

Preparation 44

1-(4-Bromo-phenyl)-cyclohexanol

4-Bromo-1-iodobenzene (5 g, 17.7 mmol) in tetrahydrofuran (20 mL) at −40° C. was treated dropwise with isopropyl magnesium chloride (2 M solution in tetrahydrofuran, 23 mmol, 11.5 mL) and following addition was stirred 1 hour. Cyclohexanone (1.5 mL, 14.75 mmol) in tetrahydrofuran (5 mL) was added and the solution was allowed to slowly warm to room temperature over 3 hours. Saturated aqueous ammonium chloride solution was added and the mixture was then diluted with ethyl acetate. The aqueous and organic layers were separated and the organic layer was washed with water (1×) and brine (1×). The combined aqueous layers were extracted with ethyl acetate (3×10 mL), the combined organic layers were dried over magnesium sulfate, were filtered, and the solvent was removed in vacuo. The residue was purified by silica gel chromatography (20:1 hexanes-ethyl acetate) to afford 3 g (67% yield) of 1-(4-bromo-phenyl)-cyclohexanol. 13C NMR (100 MHz, CDCl3) □ 148.8, 131.4, 126.8, 120.8, 73.2, 38.9, 25.6, 22.3.

Preparation 45

3-(4-Bromo-phenyl)-pentan-3-ol

The title compound was prepared using the procedure detailed for Preparation 44 with 3-pentanone in place of cyclohexanone. 1H NMR (400 MHz, CDCl3) d 7.45 (d, J=8.7 Hz, 2H), 7.24 (d, J=8.7 Hz, 2H), 1.8 (m, 4H), 1.59 (s, 1H), 0.74 (t, J=7.5 Hz, 6H); 13C NMR (100 MHz, CDCl3) d 145.0, 131.3, 127.7, 120.4, 77.5, 35.2, 8.0.

Preparation 46

1-(4-Bromo-phenyl)-cyclopentanol

The title compound was prepared using the procedure detailed for Preparation 44 with cyclopentanone in place of cyclohexanone. 1H NMR (400 MHz, CDCl3) d 7.44 (d, J=8.3 Hz, 2H), 7.35 (d, J=8.7 Hz, 2H), 1.9 (m, 6H), 1.8 (m, 2H), 1.75 (s, 1H); 13C NMR (100 MHz, CDCl3) d 146.4, 131.4, 127.2, 120.8, 83.4, 42.2, 24.1.

Preparation 49

1-(4-Bromo-phenyl)-cyclobutanol

A flame dried flask under $N_2$ was charged with 1,4-dibromobenzene (7.52 g, 31.9 mmol) and anhydrous THF (50 mL). The reaction mixture was cooled to −78° C. and 2.5 M n-BuLi in hexanes (12.8 mL, 32 mmol) was added keeping the temperature below −60° C. The reaction mixture was stirred-at −78° C. for 30 min and then cyclobutanone (2 mL, 26.8 mmol) was added slowly keeping the temp below −60° C. After one hour, the reaction was poured into a saturated $NH_4Cl$ solution (40 mL). The salts were filtered through Celite™ and washed with EtOAc (2×20 mL). The layers were separated and the aq. phase was extracted with additional EtOAc (20 mL). The combined organic layers were washed with brine, dried ($Na_2SO_4$) and concentrated to a pale yellow oil (5.51 g). The material could be used without further purification. 13C NMR (400 MHz, CDCl3) d 145.5, 131.7, 127.1, 121.3, 76.8, 37.2, 13.2; MS (AP/Cl) 209.0, 211.0 (M+H—H2O)+.

Preparation 50

4-(4-Bromo-phenyl)-tetrahydro-pyran-4-ol

The title compound was prepared using the procedure detailed for Preparation 44 with 4-oxopyran in place of cyclohexanone. 13C NMR (100 MHz, CDCl3) d 38.8, 63.9, 70.6, 121.3, 126.6, 131.7, 147.4.

Preparation 51

1-Bromo-4-(1-methoxy-1-methyl-ethyl)-benzene 2-(4-Bromo-phenyl)-propan-2-ol (Preparation 39, 1.77g, 8.2 mmol) and methyl iodide (0.5 mL, 8.2 mmol) in tetrahydrofuran (100 mL) were treated with sodium hydride (60% dispersion in mineral oil, 328 mg, 8.2 mmol). The mixture was stirred for 24 hours at room temperature, was poured into 0.5 M aqueous hydrochloric acid, and the mixture was extracted with ethyl acetate. The organic layer was washed with brine, was dried over magnesium sulfate, was filtered, and the solvent was removed in vacuo. The residue was purified by silica gel chromatography (200:1 hexanes-ethyl acetate) to afford 500 mg (27% yield) of the title compound. 13C NMR (100 MHz, CDCl3) d 145.4, 131.5, 127.9, 121.0, 76.7, 50.9, 28.1; MS (AP/Cl) 197.0, 199.0 (M+H—OMe)+.

Preparation 52

1-bromo-4-(1-methoxy-cyclobutyl)-benzene

The title compound was prepared using the procedure detailed for Preparation 51 on the corresponding hydroxyl compound prepared above. 13C NMR (100 MHz, CDCl3) d 142.5, 131.6, 128.4, 121.4, 81.3, 50.8, 33.0, 13.1; MS (AP/Cl) 209.1, 211.1 (M+H—OMe)+.

Preparation 53

1-Bromo-4-(2-methoxy-2-methyl-propyl)-benzene

The title compound was prepared using the procedure detailed for Preparation 51 on the corresponding hydroxyl compound prepared above. 13C NMR (100 MHz, CDCl3) d 137.6, 132.4, 131.1, 120.3, 75.2, 49.7, 45.9, 24.9; MS (AP/Cl) 211.1, 213.1 (M+H—OMe)+.

Preparation 54

5-Bromo-2-(tetrahydro-pyran-4-yloxy)-pyridine

A solution of 2,5-dibromopyridine (9.5 g, 40 mmol) in N,N-dimethylformamide (100 mL) was treated with sodium hydride (60% dispersion in mineral oil, 2.4 g, 60 mmol). The mixture was cooled to 0° C. and 4-hydroxypyran (3.8 mL, 40 mmol) was added slowly. The resultant mixture was stirred at room temperature for 24 hours, then was added to dilute brine solution and was extracted with ethyl acetate. The organic layer was dried over magnesium sulfate, was filtered, and the solvent was removed in vacuo. The residue was purified by silica gel chromatography (40:1 hexanes-ethyl acetate) to afford 9.0 g (87% yield) of the title compound. 13C NMR (100 MHz, CDCl3) d 162.0, 147.6, 141.5, 113.5, 111.7, 70.3, 65.7, 32.1; MS (AP/Cl) 258.2, 260.2 (M+H)+.

Preparation 55

4-(5-Bromo-pyridin-2-yl)-morpholine 2,5-Dibromopyridine (7.1 g, 30 mmol), morpholine (1.74 mL, 20 mmol), cesium carbonate (9.1 g, 28 mmol), tris(dibenzylideneacetone)dipalladium(0) (183 mg, 0.2 mmol), and racemic 2,2'-bis(diphenylphosphino)-1,1'-binaphthyl (374 mg, 0.6 mmol) in toluene (20 mL) was heated at 120° C. for 24 hours. After cooling to room temperature, the mixture was filtered through Celite™ and the Celite™ pad was washed with chloroform. The solution was concentrated in vacuo and was purified by silica gel chromatography (200:1 chloroform-methanol) to give 2.9 g (60% yield) of the title compound. 13C NMR (100 MHz, CDCl3) d 158.3, 148.7, 140.0, 108.4, 66.8, 45.7; MS (AP/Cl) 243.0, 245.0 (M+H)+.

Preparation 56

4-(4-Bromo-phenyl)-morpholine

The title compound was prepared using 1,4-dibromobenzene, but otherwise followed the procedure for Preparation 55. 1H NMR (400 MHz, CDCl3) d 7.35 (d, J=9.1 Hz, 2H), 6.77 (d, J=9.1 Hz, 2H), 3.85 (t, J=5.0 Hz, 4H), 3.12 (t, J=4.8 Hz, 4H); MS (AP/Cl) 242.1, 244.0 (M+H)+.

General Palladium Mediated Coupling Procedure

The following general procedure illustrates the method used for Pd mediated N-arylation of the pyrrolidin-2-one moiety with the corresponding aryl bromide: To a sealed tube was added 3-[5-fluoro-2-(4-methyl-piperazin-1-yl)-benzyl]-pyrrolidin-2-one (Preparation 13), aryl bromide (1.2 equiv), dipalladium tris(dibenzylideneacetone) (0.05 equiv), 9,9-dimethyl-4,5-bis(diphenylphosphino)xanthene (XANTPHOS) (0.15 equiv), cesium carbonate (1.5 equiv), and dioxane (7 volumes). The mixture was heated at 100° C. for 12 to 24 hours. After cooling to room temperature, the mixture was concentrated in vacuo and was purified by silica gel chromatography.

The following compounds were prepared via the general procedure above:

EXAMPLE 1

3-[5-Fluoro-2-(4-methyl-piperazin-1-yl)-benzyl]-1-[4-(1-hydroxy-1-methyl-ethyl)-phenyl]-pyrrolidin-2-one:

3-[5-Fluoro-2-(4-methyl-piperazin-1-yl)-benzyl]-1-[4-(1-hydroxy-1-methyl-ethyl)-phenyl]-phenyl]-pyrrolidin-2-one: 13C NMR (100 MHz, CDCl3) d 24.8, 31.9, 32.5, 44.7, 46.0, 46.9, 52.9, 55.7, 72.4, 113.9, 114.1, 116.8, 117.1, 119.7, 1222.4, 122.5, 125.2, 137.8, 137.9, 138.2, 145.6, 147.9, 158.6, 161.1, 175.5; MS (AP/Cl) 426.3 (M+H)+. The enantiomers were separable by HPLC (90/10 heptane/ethanol; Chiralcel OD, 10 cm×50 cm; 275 mL/minute). Approximate retention times: t1=12.7 minutes; t2=14.8 minutes.

EXAMPLE 2

4-{3-[2-(4-Methyl-piperazin-1-yl)-benzyl]-2-oxo-pyrrolidin-1-yl}-benzoic acid ethyl ester:

4-{3-[2-(4-Methyl-piperazin-1-yl)-benzyl]-2-oxo-pyrrolidin-1-yl}-benzoic acid ethyl ester: 13C NMR (100 MHz, CDCl3) d 176.46, 166.86, 152.14, 143.83, 134.97, 130.70, 130.55, 127.73, 125.58, 124.55, 120.86, 118.68; Anal. calcd. for C25H31N3O3: C, 71.2; H, 7.4; N, 10.0; Found: C, 70.9;H, 7.4; N, 10.1.

EXAMPLE 3

3-[2-(4-Methyl-piperazin-1-yl)-benzyl]-1-(6-morpholin-4-yl-pyridin-3-yl)-pyrrolidin-2-one:

3-[2-(4-Methyl-piperazin-1-yl)-benzyl]-1-(6-morpholin-4-yl-pyridin-3-yl)-pyrrolidin-2-one: 13C NMR (100 MHz, CDCl3) d 175.90, 156.93, 152.14, 139.17, 135.15, 130.75, 130.52, 128.27, 127.64, 124.53, 120.79, 107.02, 66.93, 55.91, 52.96, 46.82, 46.36, 46.18, 44.34, 32.40, 24.75; MS (AP/Cl) 436.2 (M+H)+. The enantiomers were separable by HPLC (70/30 heptane/ethanol with 0.025% diethylamine;

EXAMPLE 4

1-[4-(1-Hydroxy-1-methyl-ethyl)-phenyl]-3-[2-(4-methyl-piperazin-1-yl)-benzyl]-pyrrolidin-2-one:

1-[4-(1-Hydroxy-1-methyl-ethyl)-phenyl]-3-[2-(4-methyl-piperazin-1-yl)-benzyl]-pyrrolidin-2-one: 13C NMR (100 MHz, CDCl3) d 175.99, 152.05, 145.55, 138.33, 135.23, 130.54, 127.62, 125.16, 124.56, 120.83, 119.64, 72.38, 55.84, 52.80, 47.01, 46.27, 44.89, 32.51, 32.01, 24.71; MS (AP/Cl) 408.4 (M+H)+, 390.3 (M+H—H2O)+. The enantiomers were separable by HPLC (95/5 acetonitrile/methanol; Chiralpak AD, 10 cm×50 cm; 250 mL/minute). Approximate retention times: t1=25 minutes; t2=40 minutes.

EXAMPLE 5

3-[2-(4-Methyl-piperazin-1-yl)-benzyl]-1-(4-morpholin-4-yl-phenyl)-pyrrolidin-2-one:

3-[2-(4-Methyl-piperazin-1-yl)-benzyl]-1-(4-morpholin-4-yl-phenyl)-pyrrolidin-2-one: 13C NMR (100 MHz, CDCl3) d 175.57, 152.04, 148.43, 135.35, 132.70, 130.55, 127.58, 124.54, 121.18, 120.79, 116.29, 67.10, 55.84, 52.82, 49.89, 47.19, 46.26, 44.76, 32.54, 24.73; MS (AP/Cl) 435.2 (M+H)+.

EXAMPLE 6

1-[4-(1-Hydroxy-cyclopentyl)-phenyl]-3-[2-(4-methyl-piperazin-1-yl)-benzyl]-pyrrolidin-2-one:

1-[4-(1-Hydroxy-cyclopentyl)-phenyl]-3-[2-(4-methyl-piperazin-1-yl)-benzyl]-pyrrolidin-2-one: 13C NMR (100 MHz, CDCl3) d 175.94, 152.15, 143.44, 138.45, 135.25, 130.36, 127.47, 125.83, 124.51, 120.79, 119.63, 83.11, 55.91, 52.94, 47.00, 46.37, 44.90, 42.04, 32.46, 24.69, 24.03; MS (AP/Cl) 416.1 ((M+H)—H2O)+; 434.1 (M+H)+. The enantiomers were separable by HPLC (85/15 acetonitrile/methanol; Chiralpak AD, 2.1 cm×25 cm; 20 mL/minute). Retention times: t1=7 minutes; t2=11 minutes.

EXAMPLE 7

1-[4-(1-Hydroxy-cyclohexyl)-phenyl-3-[2-(4-methyl-piperazin-1-yl)-benzyl]-pyrrolidin-2-one:

1-[4-(1-Hydroxy-cyclohexyl)-phenyl]-3-[2-(4-methyl-piperazin-1-yl)-benzyl]-pyrrolidin-2-one: 2-one: 1H NMR (400 MHz, CDCl3) d 7.63 (d, J=8.7 Hz, 2H), 7.51 (d, J=9.1 Hz, 2H), 7.2 (m, 2H), 7.14 (dd, J=1.2, 7.9 Hz, 1H), 7.05 (m, 1H), 3.7 (m, 2H), 3.38 (m, 1H), 3.06 (m, 1H), 2.94 (m, 4H), 2.78 (dd, J=10.6, 13.5 Hz, 1H), 2.60 (brs, 4H), 2.35 (s, 3H), 2.06 (m, 1H), 1.9-1.6 (m, 10H), 1.3 (m, 1H); MS (AP/Cl) 448.2 (M+H)+, 430.2 (M+H—H2O)+.

EXAMPLE 8

1-[4-(1-Ethyl-1-hydroxy-propyl)-phenyl]-3-[2-(4-methyl-piperazin-1-yl)-benzyl]-pyrrolidin-2-one:

1-[4-(1-Ethyl-1-hydroxy-propyl)-phenyl]-3-[2-(4-methyl-piperazin-1-yl)-benzyl]-pyrrolidin-2-one: 13C NMR (100 MHz, CDCl3) d 175.91, 152.15, 141.99, 138.08, 135.29, 130.55, 127.59, 126.22, 124.50, 120.77, 119.28, 76.98, 55.91, 52.95, 46.96, 46.38, 44.97, 35.21, 32.53, 24.75, 8.06; MS (AP/Cl) 436.1 (M+H)+, 418.1 (M+H—H20)+. The enantiomers were separable by HPLC (methanol; Chiralpak AD, 10 cM×50 cm; 250 mL/min). Approximate retention times: t1=35 minutes; t2=68 minutes (flow rate increased to 290 mL/minute after 46 minutes).

EXAMPLE 9

1-[3-(1-Hydroxy-1-methyl-ethyl)-phenyl]-3-[2-(4-methyl-piperazin-1-yl)-benzyl]-pyrrolidin-2-one 1-[3-(1-Hydroxy-1-methyl-ethyl)-phenyl]-3-[2-(4-methyl-piperazin-1-yl)-benzyl]-pyrrolidin-2-one: 13C NMR (100 MHz, CDCl3) d 176.0, 152.0, 150.3, 139.7, 135.2, 130.6, 128.9, 127.6, 124.6, 120.8, 118.3, 116.4, 72.7, 55.8, 52.8, 47.1, 46.2, 44.9, 32.6, 32.0, 24.8; MS (AP/Cl) 408.1 (M+H)+.

EXAMPLE 10

1-[4-(2-Hydroxy-2-methyl-propyl)-phenyl]-3-[2-(4-methyl-piperazin-1-yl)-benzyl]-pyrrolidin-2-one:

1-[4-(2-Hydroxy-2-methyl-propyl)-phenyl]-3-[2-(4-methyl-piperazin-1-yl)-benzyl]-pyrrol-idin-2-one: 13C NMR (100 MHz, CDCl3) d 175.9, 152.0, 138.3, 135.2, 134.1, 131.0, 130.6, 127.6, 124.6, 120.8, 119.7, 71.0, 55.8, 52.8, 49.4, 47.0, 46.2, 44.9, 32.6, 29.4, 24.7; MS (AP/Cl) 422.5 (M+H)+. The enantiomers were separable by HPLC (methanol; Chiralpak AD, 10 cm×50 cm; 250 mL/min). Approximate retention times: t1=20 minutes; t2=38 minutes.

EXAMPLE 11

1-[6-(1-Hydroxy-1-methyl-ethyl)-pyridin-3-yl]-3-[2-(4-methyl-piperazin-1-yl)-benzyl]-pyrrolidin-2-one:

1-[6-(1-Hydroxy-1-methyl-ethyl)-pyridin-3-yl]-3-[2-(4-methyl-piperazin-1-yl)-benzyl]-pyrrolidin-2-one: 13C NMR (100 MHz, CDCl3) d 176.5, 161.9, 152.1, 138.2, 124.9, 134.9, 130.5, 128.2, 127.8, 124.6, 120.9, 118.7, 71.9, 55.9, 52.9, 46.3, 44.4, 32.4, 30.9, 24.7; MS (AP/Cl) 409.4 (M+H)+. The enantiomers were separable by HPLC (95/5 acetonitrile/methanol; Chiralpak AD, 10 cm×50 cm; 250 mL/min). Approximate retention times: t1=26 minutes; t2=37 minutes.

EXAMPLE 12

2,2-Dimethyl-3-(4-}3-[2-(4-methyl-piperazin-1-yl)-benzyl]-2-oxo-pyrrolidin-1-yl}-phenyl)-propionitrile:

2,2-Dimethyl-3-(4-{3-[2-(4-methyl-piperazin-1-yl)-benzyl]-2-oxo-pyrrolidin-1-yl}-phenyl)-propionitrile: 13C NMR (100 MHz, CDCl3) d 176.0, 152.1, 139.1, 135.2, 130.6, 127.6, 125.0, 124.5, 120.8, 119.6, 55.9, 53.0, 46.9, 46.37, 46.30, 45.0, 33.8, 32.5, 26.7, 24.7; MS (AP/Cl) 431.3 (M+H)+.

EXAMPLE 13

1-[4-(1-Methoxy-1-methyl-ethyl)-phenyl]-3-[2-(4-methyl-piperazin-1-yl)-benzyl]-pyrrolidin-2-one:

1-[4-(1-Methoxy-1-methyl-ethyl)-phenyl]-3-[2-(4-methyl-piperazin-1-yl)-benzyl]-pyrrolidin-2-one: 13C NMR (100 MHz, CDCl3) d 175.9, 152.1, 142.1, 138.6, 135.3, 130.5, 127.6, 126.6, 124.5, 120.8, 119.6, 76.7, 55.9, 53.0, 50.9, 47.0, 46.4, 44.9, 32.5, 28.2, 24.7; MS (AP/Cl) 422.2 (M+H)+.

EXAMPLE 14

1-[4-(2-Methoxy-2-methyl-propyl)-phenyl]-3-[2-(4-methyl-piperazin-1-yl )-benzyl]-pyrrolidin-2-one:

1-[4-(2-Methoxy-2-methyl-propyl)-phenyl]-3-[2-(4-methyl-piperazin-1-yl)-benzyl]-pyrrolidin-2-one: 13C NMR (100 MHz, CDCl3) d 175.8, 152.1, 138.0, 135.3, 131.0, 130.5, 129.0, 127.6, 124.5, 120.8, 119.3, 75.5, 55.9, 53.0, 49.6, 47.0, 46.4, 45.9, 45.0, 32.5, 24.9, 24.7; MS (AP/Cl) 436.4 (M+H)+.

EXAMPLE 15

1-[4-(1-Methoxy-cyclobutyl)-phenyl]-3-[2-(4-methyl-piperazin-1-yl)-benzyl]-pyrrolidin-2-one:

1-[4-(1-Methoxy-cyclobutyl)-phenyl]-3-[2-(4-methyl-piperazin-1-yl)-benzyl]-pyrrolidin-2-one: 13C NMR (100 MHz, CDCl3) d 176.0, 152.1, 139.2, 138.8, 135.2, 130.5, 127.6, 127.1, 124.5, 120.8, 119.6, 81.3, 55.9, 53.0, 50.7, 47.0, 46.4, 44.9, 33.1, 32.5, 24.7, 13.1; MS (AP/Cl) 434.4 (M+H)+.

EXAMPLE 16

3-[2-(4-Methyl-piperazin-1-yl)-benzyl]-1-(4-pyridin-4-yl-phenyl)-pyrrolidin-2-one:

3-[2-(4-Methyl-piperazin-1-yl)-benzyl]-1-(4-pyridin-4-yl-phenyl)-pyrrolidin-2-one: 13C NMR (100 MHz, CDCl3) d 176.2, 152.1, 150.5, 147.7, 140.7, 135.1, 133.7, 130.6, 127.7, 127.6, 124.6, 121.4, 120.9, 120.0, 55.9, 52.9, 46.8, 46.3, 45.0, 32.5, 24.6; MS (AP/Cl) 427.3 (M+H)+.

EXAMPLE 17

1-[4-(1-Hydroxy-cyclopentyl)-phenyl]-3-(2-piperazin-1-yl-benzyl)-pyrrolidin-2-one:

1-[4-(1-Hydroxy-cyclopentyl)-phenyl]-3-(2-piperazin-1-yl-benzyl)-pyrrolid in-2-one: 13C NMR (100 MHz, CDCl3) d 176.0, 152.4, 143.5, 138.3, 135.2, 130.6, 127.6, 125.8, 124.6, 120.9, 119.7, 83.3, 54.1, 47.1, 46.6, 44.9, 42.0, 32.44, 24.7, 24.0; MS (AP/Cl) 420.1 (M+H)+.

EXAMPLE 18

1-[4-(1-Hydroxy-cyclobutyl)-phenyl]-3-(2-piperazin-1-yl-benzyl)-pyrrolidin-2-one:

1-[4-(1-Hydroxy-cyclobutyl)-phenyl]-3-(2-piperazin-1-yl-benzyl)-pyrrolidin-2-one: 13C NMR (100 MHz, CDCl3) d 176.0, 152.4, 142.7, 138.8, 135.2, 130.6, 127.6, 124.6, 120.9, 119.8, 76.7, 54.0, 47.0, 46.6, 45.0, 37.2, 32.5, 24.7, 13.2; MS (AP/Cl) 406.2 (M+H)+.

EXAMPLE 19

1-[4-(1-Hydroxy-cyclohexyl)-phenyl]-3-(2-piperazin-1-yl-benzyl)-pyrrolidin-2-one:

1-[4-(1-Hydroxy-cyclohexyl)-phenyl]-3-(2-piperazin-1-yl-benzyl)-pyrrolidin-2-one: 13C NMR (100 MHz, CDCl3) d 175.9, 152.6, 145.8, 138.3, 135.3, 130.5, 127.6, 125.3, 124.5, 120.9, 119.7, 73.1, 54.2, 47.0, 46.8, 45.0, 39.1, 32.4, 25.7, 24.7, 22.4; MS (AP/Cl) 434.3 (M+H)+, 416.3 (M+H—H2O)+.

EXAMPLE 20

1-[4-(1-Ethyl-1-hydroxy-propyl)-phenyl]-3-(2-piperazin-1-yl-benzyl)-pyrrolidin-2-one:

1-[4-(1-Ethyl-1-hydroxy-propyl)-phenyl]-3-(2-piperazin-1-yl-benzyl)-pyrrolidin-2-one: 13C NMR (100 MHz, CDCl3) d 175.9, 152.6, 141.9, 138.1, 135.3, 130.6, 127.6, 126.2, 124.5, 120.8, 119.3, 77.4, 54.2, 47.0, 46.8, 45.0, 35.2, 32.5, 24.7, 8.1; MS (AP/Cl) 422.3 (M+H)+, 404.3 (M+H—H20)+.

EXAMPLE 21

1-[4-(1-Hydroxy-1-methyl-ethyl)-phenyl]-3-(2-piperazin-1-yl-benzyl)-pyrrolidin-2-one:

1-[4-(1-Hydroxy-1-methyl-ethyl)-phenyl]-3-(2-piperazin-1-yl-benzyl)-pyrrolidin-2-one: 13C NMR (100 MHz, CDCl3) d 176.0, 152.6, 145.5, 138.4, 135.3, 130.6, 127.6, 125.1, 124.5, 120.9, 119.7, 72.5, 54.1, 47.0, 46.7, 45.0, 32.5, 32.0, 24.7; MS (AP/Cl) 394.2 (M+H)+, 376.2 (M+H—H2O)+.

EXAMPLE 22

1-[4-(1-Hydroxy-1-methyl-ethyl)-phenyl]-3-[2-(4-methyl-piperazin-1-yl)-benzylidene]-pyrrolidin-2-one:

1-[4-(1-Hydroxy-1-methyl-ethyl)-phenyl]-3-[2-(4-methyl-piperazin-1-yl)-benzylidene]-pyrrolidin-2-one: 13C NMR (100 MHz, CDCl3) d 168.8, 152.9, 145.6, 138.5, 129.8, 129.5, 129.1, 128.9, 125.2, 122.4, 119.5, 119.0, 72.4, 55.5, 52.7, 46.2, 45.8, 32.0, 24.3; MS (AP/Cl) 406.1 (M+H)+.

EXAMPLE 23

3-[5-Fluoro-2-(4-methyl-piperazin-1-yl)-benzyl]-1-[4-(1-hydroxy-cyclopentyl)-phenyl]-pyrrolidin-2-one:

3-[5-Fluoro-2-(4-methyl-piperazin-1-yl)-benzyl]-1-[4-(1-hydroxy-cyclopentyl)-phenyl]-pyrrolidin-2-one: 13C NMR (100 MHz, CDCl3) d 24.0, 24.7, 32.4, 42.1, 44.7, 46.2, 46.9, 53.0, 55.8, 113.8, 114.0, 116.8, 117.0, 119.6, 122.3, 122.4, 125.8, 137.7, 138.3, 143.5, 148.0, 158.6, 175.0; MS (AP/Cl) 452.3 (M+H)+. The enantiomers were separable by HPLC (90/10 heptane/ethanol; Chiralcel OD, 10 cm×50 cm; 275 mL/min). Approximate retention times: t1=13.7 minutes; t2=16.2 minutes.

EXAMPLE 24

1-[4-(1-Hydroxy-cyclopentyl)-phenyl]-3-[5-methyl-2-(4-methyl-piperazin-1-yl)-benzyl]-pyrrolidin-2-one:

1-[4-(1-Hydroxy-cyclopentyl)-phenyl]-3-[5-methyl-2-(4-methyl-piperazin-1-yl)-benzyl]-pyrrolidin-2-one: 13C NMR (100 MHz, CDCl3) d 21.1, 24.0, 24.6, 32.4, 41.7, 42.0, 45.0, 46.2, 47.0, 52.8, 55.9, 83.3, 119.6, 120.7, 125.8, 128.2, 131.2, 134.0, 135.1, 138.4, 143.3, 149.5, 176.0; MS (AP/Cl) 448.4 (M+H)+.

EXAMPLE 25

1-[4-(1-Hydroxy-1-methyl-ethyl)-phenyl]-3-[5-methyl-2-(4-methyl-piperazin-1-yl)-benzyl]-pyrrolidin-2-one:

1-[4-(1-Hydroxy-1-methyl-ethyl)-phenyl]-3-[5-methyl-2-(4-methyl-piperazin-1-yl)-benzyl]-pyrrolidin-2-one: 13C NMR (100 MHz, CDCl3) d 21.1, 24.6, 31.9, 32.4, 45.0, 46.2, 47.0, 52.9, 55.9, 72.4, 119.6, 120.7, 125.1, 128.1, 131.2, 134.0, 135.1, 138.3, 145.5, 149.5, 176.0; MS (AP/Cl) 422.3 (M+H)+.

EXAMPLE 26

1-[4-(1-Hydroxy-cyclopentyl)-phenyl]-3-[2-(4-methyl-piperazin-1-yl)-benzyl]-piperidin-2-one:

1-[4-(1-Hydroxy-cyclopentyl)-phenyl]-3-[2-(4-methyl-piperazin-1-yl)-benzyl]-piperidin-2-one: 13C NMR (100 MHz, CDCl3) 22.1, 24.0, 25.8, 33.1, 42.0, 43.2, 46.2, 51.9, 52.7, 55.8, 83.3, 120.7, 124.4, 126.0, 126.1, 127.3, 130.9, 135.8, 142.3, 145.7, 152.2, 173.0; MS (AP/Cl) 448.3 (M+H)+. The enantiomers were separable by HPLC (60/40 heptane/ethanol; Chiralpak AD, 10 cm×50 cm; 275 mL/min). Approximate retention times: t1=8.3 minutes; t2=10.7 minutes.

EXAMPLE 27

1-[4-(1-Hydroxy-1-methyl-ethyl)-phenyl]-3-[2-(4-methyl-piperazin-1-yl)-benzyl]-piperidin-2-one:

1-[4-(1-Hydroxy-1-methyl-ethyl)-phenyl]-3-[2-(4-methyl-piperazin-1-yl)-benzyl]-piperidin-2-one: 13C NMR (100 MHz, CDCl3) 22.1, 25.8, 31.9, 33.1, 43.2, 46.2, 51.9, 52.7, 55.8, 72.4, 120.8, 124.4, 125.5, 126.0, 127.3, 130.9, 135.9, 142.2, 147.7, 152.2, 173.0; MS (AP/Cl) 422.3 (M+H)+. The enantiomers were separable by HPLC (60/40 heptane/ethanol; Chiralpak AD, 10 cm×50 cm; 275 mL/min). Approximate retention times: t1=6.9 minutes; t2=10.3 minutes.

EXAMPLE 28

1-[4-(1-Hydroxy-1-methyl-ethyl)-phenyl]-3-[5-methoxy-2-(4-methyl-piperazin-1-yl)-benzyl]-Pyrrolidin-2-one:

1-[4-(1-Hydroxy-1-methyl-ethyl)-phenyl]-3-[5-methoxy-2-(4-methyl-piperazin-1-yl)-benzyl]-pyrrolidin-2-one: 13C NMR (100 MHz, CDCl3) 24.5, 31.9, 32.4, 45.0, 46.2, 47.0, 53.1, 55.5, 55.8, 72.3, 112.3, 115.9, 119.6, 122.1, 125.1, 136.9, 138.2, 145.2, 145.7, 156.5, 175.9; MS (AP/Cl)438.3 (M+H)+.

EXAMPLE 29

1-[4-(1-Hydroxy-cyclopentyl)-phenyl]-3-[5-methoxy-2-(4-methyl-piperazin-1-yl)-benzyl]-pyrrolidin-2-one:

1-[4-(1-Hydroxy-cyclopentyl)-phenyl]-3-[5-methoxy-2-(4-methyl-piperazin-1-yl)-benzyl]-pyrrolidin-2-one: 13C NMR (100 MHz, CDCl3) 24.0, 24.5, 32.4, 42.0, 45.0, 46.0, 47.0, 52.9, 55.5, 55.8, 83.2, 112.2, 115.9, 119.6, 122.1, 125.8, 136.9, 138.2, 143.6, 145.1, 156.6, 175.9; MS (AP/Cl) 464.4 (M+H)+.

EXAMPLE 30

3-[2-Fluoro-6-(4-methyl-piperazin-1-yl)-benzyl]-1-[4-(1-hydroxy-cyclopentyl)-phenyl]-pyrrolidin-2-one:

3-[2-Fluoro-6-(4-methyl-piperazin-1-yl)-benzyl]-1-[4-(1-hydroxy-cyclopentyl)-phenyl]-pyrrolidin-2-one: 13C NMR (100 MHz, CDCl3) 24.0, 24.9, 25.7, 42.0, 43.9, 46.2, 46.8, 53.0, 55.7, 83.2, 111.5, 111.7, 116.6, 119.5, 122.7, 122.9, 125.8, 128.0, 128.1, 138.4, 143.4, 153.9, 153.9, 161.0, 163.4, 175.6; MS (AP/Cl)464.3 (M+H)+.

EXAMPLE 31

1-[4-(1-Hydroxy-cyclopentyl)-phenyl]-3-[2-(3,4,5-trimethyl-piperazin-1-yl)-benzyl]-pyrrolidin-2-one:

1-[4-(1-Hydroxy-cyclopentyl)-phenyl]-3-[2-(3,4,5-trimethyl-piperazin-1-yl)-benzyl]-pyrrolidin-2-one: 1H NMR (400 MHz, CDCl3) 1.13 (s, 6H), 1.51-1.69 (m, 2H), 1.80-1.89 (m, 4H), 1.98 (s, 3H), 2.31-2.51 (m, 4H), 2.60-2.71 (m, 2H), 2.79 (dd, 1H, J=10.4 and 13.6 Hz), 7.05 (dd, 1H, J=7.6 and 7.2 Hz); 7.11 (d, 1H, J=7.6 Hz0, 7.19-7.23 (m, 2h), 7.49 (d, 2H, J=9.2 Hz), 7.61 (d, 2H, J=8.8 Hz); MS (AP/Cl) 462.4 (M+H)+.

EXAMPLE 32

1-[4-(1-Hydroxy-1-methyl-ethyl)-phenyl]-3-[2-(3,4,5-trimethyl-piperazin-1-yl)-benzyl]-pyrrolidin-2-one:

1-[4-(1-Hydroxy-1-methyl-ethyl)-phenyl]-3-[2-(3,4,5-trimethyl-piperazin-1-yl)-benzyl]-pyrrolidin-2-one: 13C NMR (100 MHz, CDCl3) 18.1, 24.7, 31.9, 32.4, 38.0, 44.9, 47.0, 58.7, 60.4, 60.7, 72.5, 119.6, 120.5, 124.5, 125.1, 127.6, 130.5, 135.1, 138.3, 145.3, 151.6, 175.9; MS (AP/Cl) 436.2 (M+H)+.

EXAMPLE 33

1-[4-(4-Hydroxy-tetrahydro-pyran-4-yl)-phenyl]-3-[2-(3,4,5-trimethyl-piperazin-1-yl)-benzyl]-pyrrolidin-2-one:

1-[4-(4-Hydroxy-tetrahydro-pyran-4-y)-phenyl]-3-[2-(3,4,5-trimethyl-piperazin-1-yl)-benzyl]-pyrrolidin-2-one: 13C NMR (100 MHz, CDCl3) diagnostic peaks: 24.6, 39.0, 44.9, 46.9, 64.1, 119.8, 125.2, 127.7, 130.5; MS (AP/Cl)478.4 (M+H)+.

EXAMPLE 34

1-[4-(4-Hydroxy-tetrahdro-pyran-4-yl)-phenyl]-3-2-(4-methyl-piperazin-1-yl)-benzyl]-piperidin-2-one:

1-[4-(4-Hydroxy-tetrahydro-pyran-4-yl)-phenyl]-3-[2-(4-methyl-piperazin-1-yl)-benzyl]-piperidin-2-one: 13C NMR (100 MHz, CDCl3) 22.1, 25.8, 33.1, 38.9, 43.2, 46.2, 51.8, 52.7, 55.8, 64.1, 70.6, 120.8, 124.4, 125.6, 126.3, 127.4, 130.9, 135.8, 142.7, 146.7, 152.2, 173.0; MS (AP/Cl) 464.4 (M+H)+. The enantiomers were separable by HPLC (75/25 heptane/ethanol with 0.2% diethylamine; Chiralpak OJ, 10 cm×50 cm; 275 mL/min). Approximate retention times: t1=6.8 minutes; t2=10.6 minutes.

EXAMPLE 35

1-[4-(1-Hydroxy-1-methyl-ethyl)-phenyl]-3-[2-(3,4,5-trimethyl-piperazin-1-yl)-benzyl]-piperidin-2-one:

1-[4-(1-Hydroxy-1-methyl-ethyl)-phenyl]-3-[2-(3,4,5-trimethyl-piperazin-1-yl)-benzyl]-piperidin-2-one: 13C NMR (100 MHz, CDCl3) 18.2, 18.3, 22.2, 25.8, 31.9, 33.0, 38.0, 43.3, 51.9, 58.7, 60.3, 60.9, 72.5, 120.4, 124.4, 125.5, 126.1, 127.3, 130.9, 135.8, 1423.3, 147.6, 151.9, 173.0; MS (AP/Cl) 450.5 (M+H)+.

EXAMPLE 36

1-[4-(1-Hydroxy-cyclopentyl)-phenyl]-3-[2-(3,4,5-trimethyl-piperazin-1-yl)-benzyl]-piperidin-2-one:

1-[4-(1-Hydroxy-cyclopentyl)-phenyl]-3-[2-(3,4,5-trimethyl-piperazin-1-yl)-benzyl]-piperidin-2-one: 13C NMR (100 MHz, CDCl3) 18.1, 18.2, 22.2, 24.0, 25.8, 33.0, 38.0, 42.1, 43.3, 51.9, 58.7, 58.8, 60.3, 60.9, 83.4, 120.4, 124.4, 126.1, 126.2, 127.3, 130.9, 135.8, 142.4, 145.6, 151.9, 173.0; MS (AP/Cl) 476.5 (M+H)+.

EXAMPLE 37

3-[5-Fluoro-2-(3,4,5-trimethyl-piperazin-1-yl)-benzyl]-1-[4-(1-hydroxy-1-methyl-ethyl)-phenyl]-piperidin-2-one:

3-[5-Fluoro-2-(3,4,5-trimethyl-piperazin-1-yl)-benzyl]-1-[4-(1-hydroxy-1-methyl-ethyl)-phenyl]-piperidin-2-one: 13C NMR (100 MHz, CDCl3) 18.1, 22.3, 25.9, 31.9, 32.9, 37.9, 43.2, 51.8, 58.8, 60.6, 61.0, 72.5, 113.5, 113.7, 117.1, 117.3, 121.9, 125.5, 126.0, 138.5, 142.2, 147.7, 147.8, 172.6; MS (AP/Cl) 468.5 (M+H)+.

EXAMPLE 38

3-[5-Fluoro-2-(3,4,5-trimethyl-piperazin-1-yl)-benzyl]-1-[4-(1-hydroxy-cyclopentyl)-phenyl]-piperidin-2-one:

3-[5-Fluoro-2-(3,4,5-trimethyl-piperazin-1-yl)-benzyl]-1-[4-(1-hydroxy-cyclopentyl)-phenyl]-piperidin-2-one: 13C NMR (100 MHz, CDCl3) 18.1, 18.2, 22.3, 24.0, 25.9, 32.8, 38.0, 42.1, 43.2, 51.8, 58.7, 58.8, 60.6, 61.1, 83.3, 113.5, 113.7, 117.0, 117.2, 121.9, 122.0, 126.0, 126.1, 126.4, 129.3, 138.4, 138.5, 142.2, 145.7, 147.9, 158.5, 160.9, 172.6; MS (AP/Cl) 494.5 (M+H)+.

EXAMPLE 39

3-[2-(4-Methyl-piperazin-1-yl)-benzyl[-1-[4-(2-oxo-pyrrolidin-1-ylmethyl)-phenyl]-piperidin-2-one:

3-[2-(4-Methyl-piperazin-1-yl)-benzyl]-1-[4-(2-oxo-pyrrolidin-1-ylmethyl)-phenyl]-piperidin-2-one: 13C NMR (100 MHz, CDCl3) 17.9, 22.2, 25.8, 31.1, 33.1, 43.2, 46.2, 46.3, 46.8, 51.8, 52.8, 55.8, 120.8, 124.4, 126.6, 127.4, 129.0, 130.9, 135.0, 135.8, 143.2, 152.2, 173.0, 175.2; MS (AP/Cl) 461.5 (M+H)+.

EXAMPLE 40

3-[2-(4-Methyl-piperazin-1-yl)-benzyl]-1-(3-oxo-1,3-dihydro-isobenzofuran-5-yl)-piperidin-2-one:

3-[2-(4-Methyl-piperazin-1-yl)-benzyl]-1-(3-oxo-1,3-dihydro-isobenzofuran-5-yl)-piperidin-2-one: 13C NMR (100 MHz, CDCl3) 22.1, 25.8, 33.0, 43.3, 46.3, 51.8, 52.2, 52.8, 55.5, 55.9, 69.8, 120.8, 122.7, 122.8, 124.6, 127.0, 127.5, 130.9, 133.3, 135.5, 144.5, 144.9, 12.2, 170.7, 173.3; MS (AP/Cl) 420.5 (M+H)+.

EXAMPLE 41

3-[5-Fluoro-2-(4-methyl-piperazin-1-yl)-benzyl]-1-[4-(1-hydroxy-cyclobutyl)-phenyl]-piperidin-2-one:

3-[5-Fluoro-2-(4-methyl-piperazin-1-yl)-benzyl]-1-[4-(1-hydroxy-cyclobutyl)-phenyl]-piperidin-2-piperidin-2-one: 13C NMR (100 MHz, CDCl3) 13.1, 22.2, 26.0, 33.0, 37.1, 43.2, 46.0, 51.8, 52.9, 55.7, 113.6, 113.9, 117.1, 117.4, 122.3, 122.4, 126.1, 126.3, 142.7, 161.0, 172.6; MS (AP/Cl) 452.5 (M+H)+.

EXAMPLE 42

3-[2-(4-Methyl-piperazin-1-yl)-benzyl]-1-(3-1,3,4]oxadiazol-2-yl-phenyl)-pyrrolidin-2-one 3-[2-(4-Methyl-piperazin-1-yl)-benzyl]-1-(3-[1,3,4]oxadiazol-2-yl-phenyl)-pyrrolidin-2-one: 13C NMR (100 MHz, CDCl3) 24.6, 32.6, 44.9, 46.1, 46.8, 52.7, 53.0, 55.7, 112.4, 117.6, 120.9, 122.9, 123.2, 124.6, 127.8, 129.9, 130.5, 134.9, 140.6, 151.9, 152.9, 164.8, 176.3; MS (AP/Cl) 418.3 (M+H)+.

EXAMPLE 43

6'-(1-Hydroxy-1-methyl-ethyl)-3-[2-(4-methyl-piperazin-1-yl)-benzyl]-3,4,5,6-tetrahydro-[1,3']bipyridinyl-2-one:

6'-(1-Hydroxy-1-methyl-ethyl)-3-[2-(4-methyl-piperazin-1-yl)-benzyl]-3,4,5,6-tetrahydro-[1,3']bipyridinyl-2-one: 13C NMR (100 MHz, CDCl3) 22.1, 25.8, 30.8, 30.9, 33.1, 43.2, 46.2, 51.7, 52.8, 55.9, 118.9, 120.8, 124.5, 127.5, 130.9, 135.0, 135.5, 138.6, 114.9, 152.2, 163.9, 173.4; MS (AP/Cl) 423.4 (M+H)+. The enantiomers were separable by HPLC (70/30 heptane/ethanol; Chiralpak AD, 10 cm×50 cm; 85 mL/min). Approximate retention times: t1=11.8 minutes; t2=14.6 minutes.

EXAMPLE 44

3-[5-Fluoro-2-(4-methyl-piperazin-1-yl)-benzyl]-1-[6-(1-hydroxy-1-methyl-ethyl)-pyridin-3-yl]-pyrrolidin-2-one:

3-[5-Fluoro-2-(4-methyl-piperazin-1-yl)-benzyl]-1-[6-(1-hydroxy-1-methyl-ethyl)-pyridin-3-yl]-pyrrolidin-2-one: 13C NMR (100 MHz, CDCl3) 24.8, 30.8, 32.2, 44.3, 46.2, 53.1, 55.8, 71.9, 114.0, 114.2, 116.8, 117.0, 118.7, 122.4, 122.5, 128.3, 134.9, 137.3, 137.4, 138.1, 148.0, 148.1, 158.5, 160.9, 161.8, 176.0; MS (AP/Cl) 464.3 (M+H)+. The enantiomers were separable by HPLC (85/15 heptane/isopropanol; Chiralcel AD, 10 cm×50 cm; 85 mL/min). Approximate retention times: t1=16.1 minutes; t2=18.0 minutes.

EXAMPLE 45

3-[2-Fluoro-6-(4-methyl-piperazin-1-yl)-benzyl]-1-[6-(1-hydroxy-1-methyl-ethyl)-pyridin-3-yl]-pyrrolidin-2-one:

3-[2-Fluoro-6-(4-methyl-piperazin-1-yl)-benzyl]-1-[6-(1-hydroxy-1-methyl-ethyl)-pyridin-3-yl]-pyrrolidin-2-one: 13C NMR (100 MHz, CDCl3) 24.9, 25.5, 30.8, 43.4, 46.2, 53.0, 55.6, 71.9, 111.5, 111.7, 116.7, 118.7, 122.3, 122.5, 128.1, 128.2, 134.9, 138.1, 153.8, 153.9, 160.9, 161.8, 163.3, 176.1; MS (AP/Cl) 427.3 (M+H)+. The enantiomers were separable by HPLC (70/30 heptane/ethanol; Chiralpak AD, 10 cm×50 cm; 250 mL/min). Approximate retention times: t1=8.4 minutes; t2=12.9 minutes.

EXAMPLE 46

1-[6-(1-Hydroxy-1-methyl-ethyl)-pyridin-3-yl]-3-[2-(3,4,5-trimethyl-piperazin-1-yl)-pyrrolidin-2-one:

1-[6-(1-Hydroxy-1-methyl-ethyl)-pyridin-3-yl]-3-[2-(3,4,5-trimethyl-piperazin-1-yl)-benzyl]-pyrrolidin-2-one: 1H NMR (400 MHz, CDCl3) 1.10 (d, 3H, J=6.4 Hz), 1.12 (d, 3H, J=6.4 Hz), 1.54 (s, 6H), 1.86-1.95 (m, 1H), 2.07-2.15 (m, 1H), 2.32 (s, 3H), 2.35-2.42 (m, 1H), 2.62-2.68 (m, 1H), 2.79-2.85 (m, 2H), 2.90 (dt, 1H, J=11.2 and 2.4 Hz), 3.08 (ddd, 1H, J=14.4, 10.4, and 4.0 Hz), 3.86 (dd, 1H, J=14.0 and 4.0 Hz), 3.68-3.73 (m, 2H), 7.04 (dt, 1H, J=7.6 and 1.2 Hz), 7.10-7.13 (m, 1h), 7.20-7.24 (m, 2H), 8.29 (dd, 1H, J=8.8 and 2.8 Hz), 8.59 (d, 1H, J=2.4 Hz); MS (AP/Cl) 437.4 3 (M+H)+.

EXAMPLE 47

6'-(1-Hydroxy-1-methyl-ethyl)-3-[2-(3,4,5-trimethyl-piperazin-1-yl)-benzyl]-3,4,5,6-tetrahydro-[1,3']bipyridinyl-2-one:

6'-(1-Hydroxy-1-methyl-ethyl)-3-[2-(3,4,5-trimethyl-piperazin-1-yl)-benzyl]-3,4,5,6-tetrahydro-[1,3']bi-pyridinyl-2-one: 13C NMR (100 MHz, CDCl3) 18.1, 22.2, 25.8, 30.8, 33.1, 38.0, 43.3, 51.7, 58.8, 58.9, 60.3, 60.7, 72.0, 118.9, 120.6, 124.4, 127.5, 130.9, 135.0, 135.4, 138.6, 144.9, 151.8, 163.8, 173.4; MS (AP/Cl) 451.3 (M+H)+.

EXAMPLE 48

3-[5-Fluoro-2-(3,4,5-trimethyl-piperazin-1-yl)-benzyyl-6'-(1-hydroxy-1-methyl-ethyl)-3,4,5,6-tetrahydro-[1,3']bipyridinyl-2-one:

3-[5-Fluoro-2-(3,4,5-trimethyl-piperazin-1-yl)-benzyl]-6'-(1-hydroxy-1-methyl-ethyl)-3,4,5,6-tetrahydro-[1,3']bi-pyridinyl-2-one: 13C NMR (100 MHz, CDCl3) 18.0, 21.5, 22.2, 25.9, 30.8, 32.9, 37.8, 43.2, 51.7, 58.9, 59.0, 60.6, 60.9, 72.0, 113.7, 113.9, 117.1, 118.9, 122.1, 122.2, 135.0, 1338.0, 138.1, 138.5, 144.9, 147.7, 158.5, 160.9, 164.0, 173.0; MS (AP/Cl) 469.5 (M+H)+.

EXAMPLE 49

3-[5-Fluoro-2-(4-methyl-piperazin-1-yl)-benzyl]-6'-(1-hydroxy-1-methyl-ethyl)-3,4,5,6-tetrahydro-[1,3'] bipyridinyl-2-one:

3-[5-Fluoro-2-(4-methyl-piperazin-1-yl )-benzyl]-6'-(1-hydroxy-1-methyl-ethyl)-3,4,5,6-tetrahydro-[1,3'] bipyridinyl-2-one:

13C NMR (100 MHz, CDCl3) 22.2, 25.8, 30.8, 32.8, 43.1, 46.2, 46.3, 51.6, 53.1, 55.8, 72.0, 113.7, 113.9, 117.0, 117.2, 118.9, 122.3, 122.4, 134.9, 138.1, 138.2, 138.4, 144.9, 148.2, 148.3, 160.9, 164.0, 173.0; MS (AP/Cl) 441.5 (M+H)+. The enantiomers were separable by HPLC (50/50 heptane/ethanol with 1% TFA; Chiralpak AD, 5 cm×50 cm; 100 mL/min). Approximate retention times: t1=12.1 minutes; t2=16.1 minutes.

EXAMPLE 50

1-[4-(1-Hydroxy-cyclopentyl)-phenyl]-3-[2-(4-methyl-[1,4]diazepan-1-yl)-benzyl]-pyrrolidin-2-one:

1-[4-(1-Hydroxy-cyclopentyl)-phenyl]-3-[2-(4-methyl-[1,4]diazepan-1-yl)-benzyl]-pyrrolidin-2-one: 1H NMR (400 MHz, CDCl3) 1.80-1.89 (m, 1H), 1.96 (br s, 8H), 2.03-2.20 (m, 2H), 2.55-2.64 (m, 4H), 2.80-3.40 (m, 10H), 3.50 (dd, J=13.3, 2.9 Hz, 1H), 3.71 (dd, J=8.3, 5.6 Hz, 2H), 7.03 (dt, J=7.3, 1.2 Hz, 1H), 7.13-7.22 (m, 3H), 7.48 (d, J=9.1 Hz, 2H), 7.58 (d, J=8.7 Hz, 2H); MS (AP/Cl) 448.3 (M+H)+.

EXAMPLE 51

1-[4-(1-Hydroxy-1-methyl-ethyl)-phenyl]-3-[2-(4-methyl-[1,4]diazepan-1-yl)-benzyl]-pyrrolidin-2-one:

1-[4-(1-Hydroxy-1-methyl-ethyl)-phenyl]-3-[2-(4-methyl-[1,4]diazepan-1-yl)-benzyl]-pyrrolidin-2-one: 1H NMR (400 MHz, CDCl3) 1.55 (s, 6H), 1.80-1.88 (m, 1H), 1.97-2.11 (m, 3H), 2.44 (s, 3H), 2.68 (dd, J=13.3, 10.6 Hz, 1H), 2.75-2.90 (m, 4H), 2.95-3.25 (m, 5H), 3.45 (dd, J=13.7, 3.7 Hz, 1H), 3.68-3.72 (m, 2H), 6.99 (dt, J=7.3, 1.2 Hz, 1H), 7.11-7.20 (m, 3H), 7.47 (d, J=8.7 Hz, 2H), 7.58 (d, J=8.7 Hz, 2H); MS (AP/Cl) 422.3 (M+H)+.

EXAMPLE 52

3-[2-(4-Ethyl-piperazin-1-yl)-benzyl]-1-[4-(1-hydroxy-1-methyl-ethyl)-phenyl]-pyrrolidin-2-one:

3-[2-(4-Ethyl-piperazin-1-yl)-benzyl]-1-[4-(1-hydroxy-1-methyl-ethyl)-phenyl]-pyrrolidin-2-one: 1H NMR (400 MHz, CDCl3) 1.15-1.20 (m, 3H), 1.55 (s, 6H), 1.77-1.87 (m, 1H), 2.03-2.11 (m, 1H), 2.30-2.90 (br m, 7H), 2.93-3.15 (m, 5H), 3.37 (dd, J=13.3, 5.5 Hz, 1H), 3.62-3.72 (m, 2H), 7.04 (dt, J=7.5, 1.6 Hz, 1H), 7.14 (dd, J=7.9, 1.5 Hz, 1H), 7.18-7.22 (m, 2H), 7.47 (d, J=9.1 Hz, 2H), 7.58 (d, J=8.7 Hz, 2H); mp=135-137° C.

EXAMPLE 53

3-[2-(2,5-Dimethyl-piperazin-1-yl)-benzyl]-1-[4-(1-hydroxy-cyclopentyl)-phenyl]-pyrrolidin-2-one:

3-[2-(2,5-Dimethyl-piperazin-1-yl)-benzyl]-1-[4-(1-hydroxy-cyclopentyl)-phenyl]-pyrrolidin-2-one: 13C NMR (100 MHz, CDCl3) 17.4, 19.5; 19.6, 24.0, 24.9, 31.1, 33.0, 42.0, 44.2, 45.2, 46.9, 47.0, 51.5, 51.6, 54.1, 54.3, 54.5, 83.1, 119.5, 123.4, 123.5, 125.2, 125.8, 127.2, 127.5, 129.8, 130.8, 137.3, 137.5, 138.3, 143.5, 143.6, 150.3, 150.4, 175.9, 176.0; MS (AP/Cl) 448.4 (M+H)+.

EXAMPLE 61

General Procedure For Copper-Mediated Coupling

A mixture of 3-[2-(4-methylpiperazin-1-yl)-benzyl]-pyrrolidin-2-one, 1 equivalent of the aryl bromide corresponding to the aryl group of the N-arylated product, copper (I) iodide (0.1 equivalent), potassium carbonate (1.5 equivalents), and N-N'-dimethylethylendiamine (0.1 equivalent) in toluene (5 volumes) containing water (0.05-0.5 volume) were stirred at reflux until HPLC analysis showed disappearance of the starting aryl bromide. The mixture was cooled to room temperature and filtered through a pad of Celite™ and washed with toluene. The filtrate was washed with water and the organic extracts were washed with brine and concentrated to provide the crude arylated product.

The following compounds (Examples 62-71) were made using the same general procedure as for Example 6.

EXAMPLE 62

1-[6-(1-Ethyl-1-hydroxy-propyl)-pyridin-3-yl]-3-[2-(4-methyl-piperazin-1-yl)-benzyl]-pyrrolidin-2-one:

1-[6-(1-Ethyl-1-hydroxy-propyl)-pyridin-3-yl]-3-[2-(4-methyl-piperazin-1-yl)-benzyl]-pyrrolidin-2-one: 13C NMR (100 MHz, CDCl3) 176.5, 159.0, 152.0, 137.5, 134.9, 130.6, 128.2, 127.8, 124.6, 120.9, 119.6, 76.6, 55.9, 52.9, 46.3, 44.6, 34.95, 34.89, 32.5, 24.8, 8.0; MS (AP/Cl) 437.3 (M+H)+. The enantiomers were separable by HPLC (92/8 acetonitrile/methanol; Chiralpak AD, 10 cm×50 cm; 275 mL/min). Approximate retention times: t1=25 minutes; t2=50 minutes.

EXAMPLE 63

3-[2-(4-Methyl-piperazin-1-yl)-benzyl]-1-[6-(tetrahydro-pyran-4-yloxy)-pyridin-3-yl]-pyrrolidin-2-one:

3-[2-(4-Methyl-piperazin-1-yl)-benzyl]-1-[6-(tetrahydro-pyran-4-yloxy)-pyridin-3-yl]-pyrrolidin-2-one: 13C NMR (100 MHz, CDCl3) d 176.0, 159.9, 152.0, 137.8, 135.0, 132.0, 130.7, 130.5, 127.7, 124.6, 120.9, 111.6, 69.9, 65.8, 55.8, 52.8, 46.8, 46.2, 44.3, 32.5, 32.2, 24.8; MS (AP/Cl) 451.5 (M+H)+.

EXAMPLE 64

1-[6-(1-Hydroxy-cyclopentyl)-pyridin-3-yl]-3-[2-(4-methyl-piperazin-1-yl)-benzyl]-pyrrolidin-2-one:

1-[6-(1-Hydroxy-cyclopentyl)-pyridin-3-yl]-3-[2-(4-methyl-piperazin-1-yl)-benzyl]-pyrrolidin-2-one: 13C NMR (100 MHz, CDCl3) d 176.5, 160.7, 152.0, 138.1, 134.9, 130.5, 128.2, 127.8, 124.6, 120.9, 119.2, 82.9, 55.8, 46.4, 46.3, 44.5, 42.8, 32.5, 25.0, 24.8; MS (AP/Cl) 435.5 (M+H)+.

EXAMPLE 65

1-[4-(1-Hydroxy-cyclobutyl)-phenyl]-3-[2-(4-methyl-piperazin-1-yl)-benzyl]-pyrrolidin-2-one:

1-[4-(1-Hydroxy-cyclobutyl)-phenyl]-3-[2-(4-methyl-piperazin-1-yl)-benzyl]-pyrrolidin-2-one: 13C NMR (100 MHz, CDCl3) d 176.00, 152.08, 142.59, 138.82, 135.22, 130.54, 127.63, 125.79, 124.55, 120.83, 119.81, 76.76, 55.85, 52.84, 47.00, 46.27, 44.91, 37.20, 32.51, 24.70, 13.13; MS (AP/Cl) 420.3 (M+H)+. The enantiomers were separable by HPLC (92/8 acetonitrile/methanol; Chiralpak AD, 10 cm×50 cm; 275 mL/min). Approximate retention times: t1=30 minutes; t2=49 minutes.

EXAMPLE 66

1-[5-(1-Hydroxy-1-methyl-ethyl)-pyridin-2-yl]-3-[2-(4-methyl-piperazin-1-yl)-benzyl]-pyrrolidin-2-one:

1-[5-(1-Hydroxy-1-methyl-ethyl)-pyridin-2-yl]-3-[2-(4-methyl-piperazin-1-yl)-benzyl]-pyrrolidin-2-one: 13C NMR (100 MHz, CDCl3) d 176.7, 152.0, 150.8, 144.2, 140.3, 135.2, 134.6, 130.5, 127.7, 124.6, 120.9, 114.2, 71.2, 55.8, 52.7, 46.2, 45.8, 45.6, 32.5, 31.9, 24.5; MS (AP/Cl) 409.5 (M+H)+.

EXAMPLE 67

1-[5-(1-Hydroxy-cyclopentyl)-pyridin-2-yl]-3-[2-(4-methyl-piperazin-1-yl)-benzyl]-pyrrolidin-2-one:

1-[5-(1-Hydroxy-cyclopentyl)-pyridin-2-yl]-3-[2-(4-methyl-piperazin-1-yl)-benzyl]-pyrrolidin-2-one: 13C NMR (100 MHz, CDCl3) d 176.7, 152.0, 150.9, 144.7, 138.3, 135.22, 135.18, 130.5, 127.7, 124.6, 120.9, 114.2, 81.9, 55.8, 52.7, 46.2, 45.7, 45.6, 41.9, 32.5, 24.5, 23.9; MS (AP/Cl) 435.4 (M+H)+.

EXAMPLE 68

3-[2-(4-Methyl-piperazin-1-yl)-benzyl]-1-(4-oxazol-4-yl-phenyl)-piperidin-2-one:

3-[2-(4-Methyl-piperazin-1-yl)-benzyl]-1-(4-oxazol-4-yl-phenyl)-piperidin-2-one: 13C NMR (100 MHz, CDCl3) 22.2, 25.8, 33.0, 43.3, 46.3, 51.7, 52.9, 55.9, 120.7, 124.4, 126.4, 126.7, 127.3, 129.0, 130.9, 134.0, 135.8, 140.1, 143.7, 151.5, 152.3, 173.0; MS (AP/Cl) 431.3 (M+H)+.

EXAMPLE 69

3-[2-(4-Methyl-piperazin-1-yl)-benzyl-1-(4-pyrazol-1-yl-phenyl)-piperidin-2-one: 3-[2-(4-Methyl-piperazin-1-yl)-benzyl]-1-(4-pyrazol-1-yl-phenyl)-piperidin-2-one: 13C NMR (100 MHz, CDCl3) 22.2, 25.6, 25.8, 33.0, 43.3, 46.3, 51.8, 52.9, 55.9, 107.9, 119.9, 120.7, 124.4, 127.0, 127.3, 127.4, 130.9, 135.8, 138.4, 141.3, 142.0, 152.3, 173.1; MS (AP/Cl) 430.3 (M+H)+.

EXAMPLE 70

1-[4-(2-Methyl-oxazol-4-yl)-phenyl]-3-[2-(4-methyl-piperazin-1-yl)-benzyl]-piperidin-2-one:

1-[4-(2-Methyl-oxazol-4-yl)-phenyl]-3-[2-(4-methyl-piperazin-1-yl)-benzyl]-piperidin-2-one: 13C NMR (100 MHz, CDCl3) 14.2, 22.2, 25.8, 33.0, 43.3, 46.3, 51.7, 52.8, 55.9, 120.7, 124.4, 126.2, 126.6, 127.3, 129.5, 130.9, 133.4, 135.8, 143.3, 152.2, 17,3.0; MS (AP/Cl) 445.3 (M+H)+.

EXAMPLE 71

3-[2-(4-Methyl-piperazin-1-yl)-benzyl]-1-(4-oxazol-5-yl-phenyl)-piperidin-2-one:

13C NMR (100 MHz, CDCl3) 22.2, 25.8, 29.9, 33.0, 43.3, 46.4, 51.6, 52.9, 55.9, 120.7, 121.7, 124.4, 125.2, 126.0, 126.8, 127.4, 130.9, 135.8, 144.0, 150.7, 152.4, 173.1; MS (AP/Cl) 431.5 (M+H)+.

EXAMPLE 72

3-[2-(4-Methyl-piperazin-1-yl)-benzyl-1-[4-(morpholine-4-carbonyl)-phenyl]-pyrrolidin-2-one:

Trimethyl aluminum (2 M in toluene, 700 uL, 1.4 mmol) was added dropwise to a solution of morpholine (124 uL, 1.4 mmol) in 1,2-dichloroethane (4 mL) at 0° C. Upon completion of addition, the cold bath was removed and the solution was stirred 30 minutes at 23° C. A solution of 4-{3-[2-(4-methyl-piperazin-1-yl)-benzyl]-2-oxo-pyrrolidin-1yl}-benzoic acid ethyl ester (Example 2, 150 mg, 0.36 mmol) in 1,2-dichloroethane (2 mL) was then added and the solution was heated at 70° C. for ca. 18 hours. The solution was cooled to room temperature, methanol was carefully added to quench excess methyl aluminum species, and the mixture was then treated with sodium sulfate decahydrate (1.5 g). The mixture was stirred rapidly for 3 hours, the salts were filtered off, the solvent was removed in vacuo and the residue was purified by silica gel chromatography (20:1 chloroform-methanol w/1% ammonium hydroxide) to afford 160 mg (96% yield) of the title compound. 13C NMR (100 MHz, CDCl3) d 176.28, 170.23, 152.12, 141.26, 135.00, 130.88, 130.52, 128.25, 127.71, 124.54, 120.84, 119.35, 67.14, 67.09, 55.90, 54.36, 52.97, 46.81, 46.36, 44.91, 32.48, 24.58; MS (AP/CI) 463.2 (M+H)+. The enantiomers were separated by HPLC (60/40 heptane/ethanol; Chiralcel OJ, 10 cm×50 cm; 27.5 mL/min). Approximate retention times: t1=45 minutes; t2=60 minutes.

The following compounds (Examples 73-74) were prepared in an analogous manner.

EXAMPLE 73

1-[4-(4-Methyl-piperazine-1-carbonyl)-phenyl]-3-[2-(4-methyl-piperazin-1-yl)-benzyl]-pyrrolidin-2-one:

1-[4-(4-Methyl-piperazine-1-carbonyl)-phenyl]-3-[2-(4-methyl-piperazin-1-yl)-benzyl]-pyrrolidin-2-one: 13C NMR (100 MHz, CDCl3) d 176.24, 170.11, 152.03, 141.05, 135.03, 131.48, 130.54, 128.28, 127.71, 124.59, 120.86, 119.33, 77.52, 55.85, 55.21, 52.86, 46.83, 46.27, 44.91, 32.52, 24.62; MS (AP/CI) 476.2 (M+H)+.

EXAMPLE 74

3-[2-(4-Methyl-piperazin-1-yl)-benzyl]-1-[4-(piperidine-1-carbonyl)-phenyl]-pyrrolidin-2-one:

3-[2-(4-Methyl-piperazin-1-yl)-benzyl]-1-[4-(piperidine-1-carbonyl)-phenyl]-pyrrolidin-2-one: 13C NMR (100 MHz, CDCl3) d 176.2, 170.1, 152.0, 140.8, 135.1, 132.3, 130.6, 128.0, 127.7, 124.6, 120.9, 119.3, 55.8, 52.8, 49.1, 46.9, 46.2, 44.9, 43.5, 32.5, 26.8, 25.9, 24.8, 24.6; MS (AP/CI) 461.2 (M+H)+. The enantiomers were separable by HPLC (5/95 acetonitrile/methanol; Chiralpak AD, 4.6 mm×25 cm; 1 mL/min). Retention times: t1=8.9 minutes; t2=19.1 minutes.

EXAMPLE 75

3-(2-pyridin-4-yl-benzylidene)-pyrrolidin-2-one:

The title compound was prepared via reaction between 2-pyridin-4-yl-benzaldehyde and N-acetylpyrrolidinone using General Aldol Procedure 1. 13C NMR (100 MHz, CDCl3) d 172.6, 149.9, 148.5, 140.0, 133.7, 132.8, 130.3, 128.9, 128.7, 128.4, 124.8, 40.0, 26.4; MS (AP/CI) 252.1 (M+H)+.

EXAMPLE 76

3-[2-(1-Methyl-1,2,3,6-tetrahydro-pyridin-4-yl)-benzylidenel-pyrrolidin-2-one:

A solution of 3-(2-pyridin-4-yl-benzylidene)-pyrrolidin-2-one (Example 77, 500 mg, 2 mmol) and methyl iodide (150 uL, 2.4 mmol) in acetonitrile (5 mL) was stirred at room temperature for 1 hour. Methanol (5 mL) was added to improve solubility then 10 equiv methyl iodide was added. The mixture was heated at 40° C. for 18h, then was heated at 75° C. for 18 hours. The solvent was removed in vacuo, methanol was added and the process was repeated three times (to remove methyl iodide). The residue was dissolved in methanol (20 mL), was cooled to 0° C., and sodium borohydride (151 mg, 4.0 mmol) was added in small portions. After addition was completed, the mixture was stirred at room temperature for 2 hours. The solvent was removed in vacuo, water was added, and the mixture was extracted with diethyl ether (5x). The organic layer was dried over magnesium sulfate, was filtered, and the solvent was removed in vacuo. The residue was purified by silica gel chromatography (50:1 chloroform-methanol w/1% ammonium hydroxide) to afford 313 mg (58% yield) of the title compound. 13C NMR (100 MHz, CDCl3) d 172.9, 144.4, 135.8, 133.4, 130.9, 129.5, 128.8, 128.5, 128.3, 127.0, 126.1, 54.8, 52.2, 45.9, 40.0, 31.5, 26.5; MS (AP/CI) 269.2 (M+H)+.

EXAMPLE 77

3-[2-(1-Methyl-piperidin-4-yl)-benzyl]-pyrrolidin-2-one:

A mixture of 3-[2-(1-Methyl-1,2,3,6-tetrahydro-pyridin-4-yl)-benzylidene]-pyrrolidin-2-one (Example 78), 308 mg, 1.15 mmol) and 10% palladium on carbon (300 mg) in methanol (20 mL) was placed under 50 psi hydrogen and was heated at 50° C. for 8 hours. The mixture was cooled to room temperature, was filtered through Celite™, and the solvent was removed in vacuo to afford 310 mg (99% yield) of the title compound. 13C NMR (100 MHz, CDCl3) d 180.1, 144.5, 136.8, 129.9, 127.1, 126.6, 126.2, 56.7, 46.7, 42.7, 40.6, 37.2, 33.9, 33.6, 33.5, 27.7; MS (AP/CI) 273.2 (M+H)+.

The compounds in examples 80-83 were prepared from the corresponding N-arylated 3-(2-pyridin-4-yl-benzylidene)-pyrrolidin-2-one using procedures analogous to that used for Examples 1-62 general palladium mediated coupling conditions.

EXAMPLE 78

1-[4-(1-Hydroxy-cyclobutyl)-phenyl]-3-[2-(1-methyl-piperidin-4-yl)-benzyl]-pyrrolidin-2-one:

1-[4-(1-Hydroxy-cyclobutyl)-phenyl]-3-[2-(1-methyl-piperidin-4-yl)-benzyl]-pyrrolidin-2-one: 13C NMR (100 MHz, CDCl3) d 175.3, 144.4, 142.9, 138.6, 136.7, 130.0, 127.2, 126.8, 126.2, 125.8, 119.8, 76.6, 56.6, 46.9, 46.5, 45.4, 37.2, 34.0, 33.8, 33.3, 25.1, 13.2; MS (AP/CI) 419.3 (M+H)+.

EXAMPLE 79

1-[4-(1-Hydroxy-cyclohexyl)-phenyl-3-[2-(1-methyl-piperidin-4-yl)-benzyyl-pyrrolidin-2-one:

13C NMR (100 MHz, CDCl3) d 175.3, 146.0, 144.4, 138.1, 136.7, 130.0, 127.2, 126.8, 126.2, 125.4, 119.6, 73.1, 56.6, 46.9, 46.6, 45.4, 37.2, 34.0, 33.8, 33.3, 25.72, 25.1, 22.4; MS (AP/Cl) 447.3 (M+H)+, 429.3 (M+H—H2O)+.

EXAMPLE 80

1-[4-(1-Hydroxy-1-methyl-ethyl)-phenyl]-3-[2-(1-methyl-piperidin-4-yl)-benzyl]-pyrrolidin-2-one:

1-[4-(1-Hydroxy-1-methyl-ethyl)-phenyl]-3-[2-(1-methyl-piperidin-4-yl)-benzyl]-pyrrol-idin-2-one: 13C NMR (100 MHz, CDCl3) d 175.3, 145.7, 144.4, 138.2, 126.7, 130.0, 127.2, 126.8, 126.2, 125.2, 119.7, 72.4, 56.6, 46.9, 46.6, 45.4, 37.2, 34.0, 33.8, 33.3, 25.1; MS (AP/Cl) 407.3 (M+H)+, 389.3 (M+H—H2O)+.

EXAMPLE 81

1-[4-(1-Hydroxy-cyclopentyl)-phenyl]-3-[2-(1-methyl-piperidin-4-yl)-benzyl]-pyrrolidin-2-one: 13C NMR (100 MHz, CDCl3) d 175.3, 144.4, 143.6, 138.3, 136.7, 130.0, 127.2, 126.8, 126.2, 125.8, 119.7, 56.6, 46.9, 46.6, 45.4, 42.1, 37.2, 34.0, 33.8, 33.3, 25.1, 24.0; MS (AP/Cl) 433.3 (M+H)+, 415.3 (M+H—H2O)+.

The invention claimed is:

1. A compound of the formula I

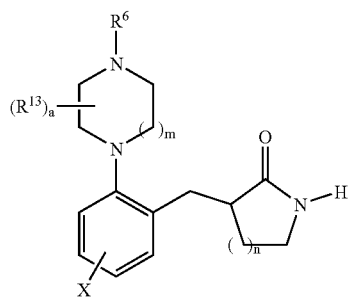

wherein $R^1$ is a group of the formula $G^1$ depicted below,

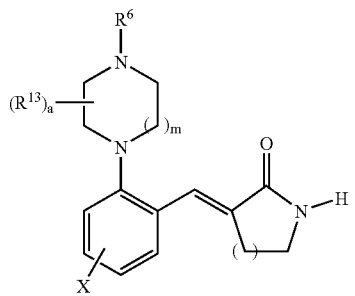

a is zero to eight;
m is one;
$R^1$ is selected from the group consisting of hydrogen, $(C_1-C_6)$alkyl optionally substituted with $(C1-C_6)$alkoxy or one to three fluorine atoms, or $((C_1-C_4)$alkyl)aryl wherein the aryl moiety is phenyl, naphthyl, or heteroaryl-(CH2)q-, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, cyano and -S01$(C_1-C_6)$alkyl, wherein t is zero, one or two;

each $R^{13}$ is, independently, $(C_1-C_4)$;

X is hydrogen, chioro, fluoro, bromo, iodo, cyano, $(C_1-C_6)$ alkyl, hydroxy, $(C_1-C_6)$alkoxy, $-SO_t(C_1-C_6)$alkyl wherein t is zero, one or two, $-CO_2R^{10}$ or $-CONR^{11}R^{12}$; each of $R^{10}$, $R^{11}$ and $R^{12}$ is selected, independently, from hydrogen, $(C_1-C_4)$alkyl, phenyl and naphthyl, wherein said phenyl or naphthyl may optionally be substituted with one or more substituents independently selected from chloro, fluoro, bromo, iodo, $(C_1-C_6)$alkyl, $(C_1-C_6)$alkoxy, trifluoromethyl, cyano and $-SO_t(C_1-C_6)$alkyl wherein t is zero, one or two; or $R^{11}$ and $R^{12}$, together with the nitrogen to which they are attached, form a 5- to 7-membered heteroalkyl ring that may contain from zero to four heteroatoms selected from nitrogen, sulfur and oxygen;

$R^3$ is $-(CH_2)_gB$, wherein g is zero to three and B is phenyl or pyridyl, and wherein phenyl or pyridyl each ring is substituted with one to three substituents independently selected from $(C_1-C_8)$hydroxyalkyl-, $(C_1-C_8)$alkoxy-$(C_1-C_8)$alkyl-, $(C_3-C_8)$hydroxycycloalkyl-, $(C_3-C_8)$cycloalkoxy-, $(C_1-C_8)$alkoxy-$(C_3-C_8)$cycloalkyl-, heterocycloalkyl, hydroxyheterocycloalkyl, and $(C_1-C_8)$ alkoxy-heterocycloalkyl, wherein each $(C_3-C_8)$ cycloalkyl or heterocycloalkyl moiety may be independently substituted with from one to three $(C_1-C_6)$alkyl or benzyl groups; or when B is a phenyl or pyridyl, each said ring is substituted with one to three substituents independently selected from phenyl, naphthyl and a 5- to 6-membered heteroaryl ring containing from one to four heteroatoms selected from oxygen, nitrogen and sulfur, with the proviso that said heteroaryl ring cannot contain two adjacent oxygen atoms or two adjacent sulfur atoms, and wherein each independently selected phenyl, naphthyl or heteroaryl substituent may itself be substituted with from one to three $(C_1-C_8)$alkyl or $C_3-C_8$ cycloalkyl substituents; or when B is a phenyl or pyridyl, each said ring is substituted with one to three substituents independently selected from (a) lactone formed from $(CH_2)_tOH$ with an ortho -COOH, wherein t is one, two or three; (b) $-CONR^{14}R^{15}$, wherein $R^{14}$ and $R^{15}$ are independently selected from $(C_1-C_8)$alkyl and benzyl, or $R^{14}$ and $R^{15}$ together with the nitrogen to which they are attached form a 5- to 7-membered heteroalkyl ring that may contain from zero to three heteroatoms selected from nitrogen, sulfur and oxygen in addition to the nitrogen of the $-CONR^{14}R^{15}$ group, wherein when any of said heteroatoms is nitrogen it may be optionally substituted with $(C_1-C_8)$alkyl or benzyl, with the proviso that said ring cannot contain two adjacent oxygen atoms or two adjacent sulfur atoms; (c) $-(CH_2)_vNCOR^{16}R^{17}$ wherein v is zero, one, two or three and $-COR^{16}$ and $R^{17}$ taken together with the nitrogen to which they are attached form a 4- to 6-membered lactam ring; and, (d) $-(C_1-C_8)NR^{18}R^{19}$ where each of $R^{18}$ and $R^{19}$ is selected, independently, from hydrogen and $(C_1-C_4)$ alkyl, or $R^{18}$ and $R^{19}$, together with the nitrogen to which they are attached, form a 4- to 7-membered heteroalkyl ring that may contain from zero to four heteroatoms selected from nitrogen, sulfur and oxygen;

wherein the broken lines indicate optional double bonds;
n is one, two, or three; or
a pharmaceutically acceptable salt thereof or optical isomer of said compound or salt thereof.

2. A compound according to claim 1 wherein $R^3$ is $(CH_2)_gB$ wherein g is zero and B is selected from phenyl and pyridyl, or pharmaceutically acceptable salt thereof or optical isomer of said compound or salt thereof.

3. A compound according to claim 2, wherein B is phenyl and wherein the compound is selected from the group consisting of:

3-[5-Fluoro-2-(4-methyl-piperazin-1-yl)-benzyl]-1-[4-(1-hydroxy-1-methyl-ethyl)-phenyl]-pyrrolidin-2-one,
1-[4-(1-Hydroxy-1-methyl-ethyl)-phenyl]-3-[2-(4-methyl-piperazin-1-yl)-benzyl]-pyrrolidin-2-one,
1-[4-(1-Ethyl-1-hydroxy-propyl)-phenyl]-3-[2-(4-methyl-piperazin-1-yl)-benzyl]-pyrrolidin-2-one,
1-[3-(1-Hydroxy-1-methyl-ethyl)-phenyl]-3-[2-(4-methyl-piperazin-1-yl)-benzyl]-pyrrolidin-2-one,
1-[4-(2-Hydroxy-2-methyl-propyl)-phenyl]-3-[2-(4-methyl-piperazin-1-yl)-benzyl]-pyrrolidin-2- one,
1-[4-(1-Methoxy-1-methyl-ethyl)-phenyl]-3-[2-(4-methyl-piperazin-1-yl)-benzyl]-pyrrolidin-2- one,
1-[4-(2-Methoxy-2-methyl-propyl)-phenyl]-3-[2-(4-methyl-piperazin-1-yl)-benzyl]-pyrrolidin-2- one,
1-[4-(1-Ethyl-1-hydroxy-propyl)-phenyl]-3-(2-piperazin-1-yl-benzyl)-pyrrolidin-2-one,
1-[4-(1-Hydroxy-1-methyl-ethyl)-phenyl]-3-(2-piperazin-1-yl-benzyl)-pyrrolidin-2-one,
1-[4-(1-Hydroxy-1-methyl-ethyl)-phenyl]-3-[2-(4-methyl-piperazin-1-yl)-benzylidene]-pyrrolidin-2-one,
1-[4-(1-Hydroxy-1-methyl-ethyl)-phenyl]-3-[5-methyl-2-(4-methyl-piperazin-1-yl)-benzyl]-pyrrolidin-2-one,
1-[4-(1-Hydroxy-1-methyl-ethyl)-phenyl]-3-[2-(4-methyl-piperazin-1-yl)-benzyl]-piperidin-2-one,
1-[4-(1-Hydroxy-1-methyl-ethyl)-phenyl]-3-[5-methoxy-2-(4-methyl-piperazin-1-yl)-benzyl]-pyrrolidin-2-one,
1-[4-(1-Hydroxy-1-methyl-ethyl)-phenyl]-3-[2-(3,4,5-trimethyl-piperazin-1-yl)-benzyl]-pyrrolidin-2-one,
1-[4-(1-Hydroxy-1-methyl-ethyl)-phenyl]-3-[2-(3,4,5-trimethyl-piperazin-1-yl)-benzyl]-piperidin-2-one,
3-[5-Fluoro-2-(3,4,5-trimethyl-piperazin-1-yl)-benzyl]-1-[4-(1-hydroxy-1-methyl-ethyl)-phenyl]-piperidin-2-one,
3-[2-(4-Ethyl-piperazin-1-yl)-benzyl]-1-[4-(1-hydroxy-1-methyl-ethyl)-phenyl]-pyrrolidin-2-one,
or a pharmaceutically acceptable salt thereof or optical isomer of said compound or salt thereof.

4. A compound according to claim 2, wherein B is phenyl and wherein the compound is selected from the group consisting of:

1-[4-(1-Hydroxy-1-methyl-ethyl)-phenyl]-3-[2-(4-methyl-piperazin-1-yl)-benzyl]-pyrrolidin-2-one,
1-[4-(1-Ethyl-1-hydroxy-propyl)-phenyl]-3-[2-(4-methyl-piperazin-1-yl)-benzyl]-pyrrolidin-2- one,
1-[4-(2-Hydroxy-2-methyl-propyl)-phenyl]-3-[2-(4-methyl-piperazin-1-yl)-benzyl]-pyrrolidin-2-one,
1-[4-(1-Methoxy-1-methyl-ethyl)-phenyl]-3-[2-(4-methyl-piperazin-1-yl)-benzyl]-pyrrolidin-2-one,
1-[4-(1-Hydroxy-1-methyl-ethyl)-phenyl]-3-[2-(4-methyl-piperazin-1-yl)-benzyl]-piperidin-2-one, or a pharmaceutically acceptable salt thereof or optical isomer of said compound or salt thereof.

5. A compound according to claim 4 that is 1-[4-(1-Hydroxy-1-methyl-ethyl)-phenyl]-3-[2-(4-methyl-piperazin-1-yl)-benzyl]-pyrrolidin-2-one, or a pharmaceutically acceptable salt thereof or optical isomer of said compound or salt thereof.

6. A compound according to claim 4 that is 1-[4-(1-Ethyl-1-hydroxy-propyl)-phenyl]-3-[2-(4-methyl-piperazin-1-yl)-benzyl]-pyrrolidin-2-one, or a pharmaceutically acceptable salt thereof or optical isomer of said compound or salt thereof.

7. A compound according to claim 4 that is 1-[4-(2-Hydroxy-2-methyl-propyl)-phenyl]-3-[2-(4-methyl-piperazin-1-yl)-benzyl]-pyrrolidin-2-one, or a pharmaceutically acceptable salt thereof or optical isomer of said compound or salt thereof.

8. A compound according to claim 4 that is 1-[4-(1-Methoxy-1-methyl-ethyl)-phenyl]-3-[2-(4-methyl-piperazin-1-yl)-benzyl]-pyrrolidin-2-one, or a pharmaceutically acceptable salt thereof or optical isomer of said compound or salt thereof.

9. A compound according to claim 4 that is 1-[4-(1-Hydroxy-1-methyl-ethyl)-phenyl]-3-[2-(4-methyl-piperazin-1-yl)-benzyl]-piperidin-2-one, or a pharmaceutically acceptable salt thereof or optical isomer of said compound or salt thereof.

10. A compound according to claim 2, wherein B is pyridyl and wherein the compound is selected from the group consisting of:

1-[6-(1-Hydroxy-1-methyl-ethyl)-pyridin-3-yl]-3-[2-(4-methyl-piperazin-1-yl)-benzyl]-pyrrolidin-2-one,
6'-(1-Hydroxy-1-methyl-ethyl)-3-[2-(4-methyl-piperazin-1-yl)-benzyl]-3,4,5,6-tetrahydro-[1,3]bibyridinyl-2-one,
3-[5-Fluoro-2-(4-methyl-piperazin-1-yl)-benzyl]-1-[6-(1-hydroxy-1-methyl-ethyl)-pyridin-3-yl]-pyrrolidin-2-one,
3-[2-Fluoro-6-(4-methyl-piperazin-1-yl)-benzyl]-1-[6-(1-hydroxy-1-methyl-ethyl)-pyridin-3-yl]-pyrrolidin-2-one,
1-[6-(1-Hydroxy-1-methyl-ethyl)-pyridin-3-yl]-3-[2-(3,4,5-trimethyl-piperazin-1-yl)-benzyl]-pyrrolidin-2-one,
6'-(1-Hydroxy-1-methyl-ethyl)-3-[2-(3,4,5-trimethyl-piperazin-1-yl)-benzyl]-3,4,5,6-tetrahydro-[1,3']bi-pyridinyl-2-one,
3-[5-Fluoro-2-(3,4,5-trimethyl-piperazin-1-yl)-benzyl]-6'-(1-hydroxy-1-methyl-ethyl)-3,4,5,6-tetrahydro-[1,3']bipyridinyl-2-one,
3-[5-Fluoro-2-(4-methyl-piperazin-1-yl)-benzyl]-6'-(1-hydroxy-1-methyl-ethyl)-3,4,5,6-tetrahydro-[1,3']bipyridinyl-2-one,
1-[6-(1-Ethyl-1-hydroxy-propyl)-pyridin-3-yl]-3-[2-(4-methyl-piperazin-1-yl)-benzyl]- pyrrolidin-2-one,
1-[5-(1-Hydroxy-1-methyl-ethyl)-pyridin-2-yl]-3-[2-(4-methyl-piperazin-1-yl)-benzyl]-pyrrolidin-2-one, or a pharmaceutically acceptable salt thereof or optical isomer of said compound or salt thereof.

11. A compound according to claim 10 that is 1-[6-(1-Hydroxy-1-methyl-ethyl)-pyridin-3-yl]-3-[2-(4-methyl-piperazin-1-yl)-benzyl]-pyrrolidin-2-one, or a pharmaceutically acceptable salt thereof or optical isomer of said compound or salt thereof.

12. A compound according to claim 10 that is 6'-(1-Hydroxy-1-methyl-ethyl)-3-[2-(4-methyl-piperazin-1-yl)-benzyl]-3,4,5,6-tetrahydro-[1,3']bipyridinyl-2-one, or a pharmaceutically acceptable salt thereof or optical isomer of said compound or salt thereof.

13. A compound according to claim 10 that is 3-[5-Fluoro-2-(4-methyl-piperazin-1-yl)-benzyl]-1-[6-(1-hydroxy-1-methyl-ethyl)-pyridin-3-yl]-pyrrolidin-2-one, or a pharmaceutically acceptable salt thereof or optical isomer of said compound or salt thereof.

14. A compound according to claim 10 that is 3-[2-Fluoro-6-(4-methyl-piperazin-1-yl)-benzyl]-1-[6-(1-hydroxy-1-methyl-ethyl)-pyridin-3-yl]-pyrrolidin-2-one, or a pharmaceutically acceptable salt thereof or optical isomer of said compound or salt thereof.

15. A compound according to claim 10 that is 1-[6-(1-Hydroxy-1-methyl-ethyl)-pyridin-3-yl]-3-[2-(3 ,4,5-trimethyl-piperazin-1-yl)-benzyl]-pyrrolidin-2-one, or a pharmaceutically acceptable salt thereof or optical isomer of said compound or salt thereof.

16. A compound according to claim 10 that is 1-[6-(1-Ethyl-1-hydroxy-propyl)-pyridin-3-yl]-3-[2-(4-methyl-piperazin-1-yl)-benzyl]-pyrrolidin-2-one, or apharmaceutically acceptable salt thereof or optical isomer of said compound or salt thereof.

17. A compound according to claim 1 wherein said ($C_3$-$C_8$)cycloalkyl moiety of said ($C_3$-$C_8$)hydroxycycloalkyl-, ($C_3$-$C_8$)cycloalkoxy-, or ($C_1$-$C_8$)alkoxy ($C_3$-$C_8$)cycloalkyl-substituents is selected from cyclobutyl, cyclopentyl and cyclohexyl, or a pharmaceutically acceptable salt thereof or optical isomer of said compound or salt thereof.

18. A compound according to claim 17, wherein the compound is selected from the group consisting of:
1-[4-(1-Hydroxy-cyclopentyl)-phenyl]-3-[2-(4-methyl-piperazin-1-yl)-benzyl]-pyrrolidin-2-one,
1-[4-(1-Hydroxy-cyclohexyl)-phenyl]-3-[2-(4-methyl-piperazin-1-yl)-benzyl]-pyrrolidin-2-one,
1-[4-(1-Methoxy-cyclobutyl)-phenyl]-3-[2-(4-methyl-piperazin-1-yl)-benzyl]-pyrrolidin-2-one,
1-[4-(1-Hydroxy-cyclopentyl)-phenyl]-3-(2-piperazin-1-yl-benzyl)-pyrrolidin-2-one,
1-[4-(1-Hydroxy-cyclobutyl)-phenyl]-3-(2-piperazin-1-yl-benzyl)-pyrrolidin-2-one,
1-[4-(1-Hydroxy-cyclohexyl)-phenyl]-3-(2-piperazin-1-yl-benzyl)-pyrrolidin-2-one,
3-[5-Fluoro-2-(4-methyl-piperazin-1-yl)-benzyl]-1-[4-(1-hydroxy-cyclopentyl)-phenyl]-pyrrolidin-2-one,
1-[4-(1-Hydroxy-cyclopentyl)-phenyl]-3-[5-methyl-2-(4-methyl-piperazin-1-yl)-benzyl]-pyrrolidin-2-one,
1-[4-(1-Hydroxy-cyclopentyl)-phenyl]-3-[2-(4-methyl-piperazin-1-yl)-benzyl]-piperidin-2-one,
1-[4-(1-Hydroxy-cyclopentyl)-phenyl]-3-[5-methoxy-2-(4-methyl-piperazin-1-yl)-benzyl]-pyrrolidin-2-one,
3-[2-Fluoro-6-(4-methyl-piperazin-1-yl)-benzyl]-1-[4-(1-hydroxy-cyclopentyl)-phenyl]-pyrrolidin-2-one,
1-[4-(1-Hydroxy-cyclopentyl)-phenyl]-3-[2-(3 ,4,5-trimethyl-piperazin-1-yl)-benzyl]-pyrrolidin-2-one,
1-[4-(1-Hydroxy-cyclopentyl)-phenyl]-3-[2-(3 ,4,5-trimethyl-piperazin-1-yl)-benzyl]-piperidin-2-one,
3-[5-Fluoro-2-(3 ,4 ,5-trimethyl-piperazin-1-yl)-benzyl]-1-[4-(1-hydroxy-cyclopentyl)-phenyl]-piperidin-2-one,
3-[5-Fluoro-2-(4-methyl-piperazin-1-yl)-benzyl]-1-[4-(1-Hydroxy-cyclobutyl)-phenyl]-piperidin-2-one, 1-[4-(1-Hydroxy-cyclopentyl)-phenyl]-3-[2-(4-methyl-[1 ,4]diazepan-1-yl)-benzyl]-pyrrolidin-2-one,
3-[2-(2,5-Dimethyl-piperazin-1-yl)-benzyl]-1-[4-(1-hydroxy-cyclopentyl)-phenyl]-pyrrolidin-2-one,
1-[6-(1-Hydroxy-cyclopentyl)-pyridin-3-yl]-3-[2-(4-methyl-piperazin-1-yl)-benzyl]-pyrrolidin-2-one,
1-[4-(1-Hydroxy-cyclobutyl)-phenyl]-3-[2-(4-methyl-piperazin-1-yl)-benzyl]-pyrrolidin-2-one,
1-[5-(1-Hydroxy-cyclopentyl)-pyridin-2-yl]-3-[2-(4-methyl-piperazin-1-yl)-benzyl]-pyrrolidin-2-one,
1-[4-(1-Hydroxy-cyclobutyl) phenyl]-3-[2(1 methyl piperidin 4 yl) benzyl]pyrrolidin 2 one,
1-[1-(1 Hydroxy-cyclohexyl) phenyl]-3-[2(1 methyl piperidin I yl) benzyl]pyffolidin 2 one, or a pharmaceutically acceptable salt thereof or optical isomer of said compound or salt thereof.

19. A compound according to claim 17, wherein the compound is selected from the group consisting of:
1-[4-(1-Hydroxy-cyclopentyl)-phenyl]-3-[2-(4-methyl-piperazin-1-yl)-benzyl]-piperidin-2-one,
3-[2-Fluoro-6-(4-methyl-piperazin-1-yl)-benzyl]-1-[4-(1-hydroxy-cyclopentyl)-phenyl]-pyrrolidin-2-one,
1-[4-(1-Hydroxy-cyclopentyl)-phenyl]-3-[2-(3 ,4,5-trimethyl-piperazin-1-yl)-benzyl]-pyrrolidin-2-one,
3-[5-Fluoro-2-(4-methyl-piperazin-1-yl)-benzyl]-1-[4-(1-hydroxy-cyclobutyl)-phenyl]-piperidin-2-one,
1-[4-(1-Hydroxy-cyclobutyl)-phenyl]-3-[2-(4-methyl-piperazin-1-yl)-benzyl]-pyrrolidin-2-one, or a pharmaceutically acceptable salt thereof or optical isomer of said compound or salt thereof.

20. A compound according to claim 1 wherein said heterocycloalkyl of said one to three optional substituents, is selected from tetrahydropyranyl, morpholinyl, azetidinyl, pyrrolidinyl, piperidyl, piperazinyl, thiomorpholinyl, hexahydroazepinyl, diazepinyl, oxazepinyl, thiazepinyl, oxetanyl and tetrahydrofiaranyl, or a pharmaceutically acceptable salt thereof or optical isomer of said compound or salt thereof.

21. A compound according to claim 20, wherein the compound is selected from the group consisting of:
3-[2-(4-Methyl-piperazin-1-yl)-benzyl]-1-(6-morpholin-4-yl-pyridin-3-yl)-pyrrolidin-2-one,
3-[2-(4-Methyl-piperazin-1-yl)-benzyl]-1-(4-morpholin-4-yl-phenyl)-pyrrolidin-2-one,
1-[4-(4-Hydroxy-tetrahydro-pyran-4-yl)-phenyl]-3-[2-(3,4,5-trimethyl-piperazin-1-yl)-benzyl]-pyrrolidin-2-one,
1-[4-(4-Hydroxy-tetrahydro-pyran-4-yl)-phenyl]-3-[2-(4-methyl-piperazin-1-yl)-benzyl]-piperidin-2-one, or a pharmaceutically acceptable salt thereof or optical isomer of said compound or salt thereof.

22. A compound according to claim 1 wherein said 5-to 6-membered heteroaryl ring of said one to three optional substituents is selected from pyridyl, pyrrolyl, pyrazolyl, imidazolyl, triazolyl, tetrazolyl, oxazolyl and oxadiazolyl, or a pharmaceutically acceptable salt thereof or optical isomer of said compound or salt thereof.

23. A compound according to claim 22, wherein the compound is selected from the group consisting of:
3-[2-(4-Methyl-piperazin-1-yl)-benzyl]-1-(4-pyridin-4-yl-phenyl)-pyrrolidin-2-one,
3-[2-(4-Methyl-piperazin-1-yl)-benzyl]-1-(3-[1,3 ,4]oxadiazol-2-yl-phenyl)-pyrrolidin-2-one,
3-[2-(4-Methyl-piperazin-1-yl)-benzyl]-1-(4-oxazol-4-yl-phenyl)-piperidin-2-one,
1-[4-(2-Methyl-oxazol-4-yl)-phenyl]-3-[2-(4-methyl-piperazin-1-yl)-benzyl]-piperidin-2-one,
1-[4-(2-Methyl-oxazol-4-yl)-phenyl]-3-[2-(4-methyl-piperazin-1-yl)-benzyl]-piperidin-2-one,
3-[2-(4-Methyl-piperazin-1-yl)-benzyl]-1-(4-oxazol-5-yl-phenyl)-piperidin-2-one, or a pharmaceutically acceptable salt thereof or optical isomer of said compound or salt thereof.

24. A compound according to claim 1 wherein said $R^{14}$ and said $R^{15}$ groups of said —$CONR^{14}R^{15}$ substituent together with the nitrogen to which they are attached form a 6-membered heteroalkyl ring selected from piperidine, N-($C_0$-$C_6$)

alkylpiperazine and morpholine, or a pharmaceutically acceptable salt thereof or optical isomer of said compound or salt thereof.

25. A compound according to claim 24, wherein the compound is selected from the group consisting of:
3-[2-(4-Methyl-piperazin-1-yl)-benzyl]-1-[4-(morpholine-4-carbonyl)-phenyl]-pyrrolidin-2-one,
1-[4-(4-Methyl-piperazine-1-carbonyl)-phenyl]-3-[2-(4-methyl-piperazin-1-yl)-benzyl]-pyrrolidin-2-one
3-[2-(4-Methyl-piperazin-1-yl)-benzyl]-1-[4-(piperidine-1-carbonyl)-phenyl]-pyrrolidin-2-one, or a pharmaceutically acceptable salt thereof or optical isomer of said compound or salt thereof.

26. A compound according to claim 1 wherein said —COR$^{16}$ and R$^{17}$ groups of said (CH$_2$)$_v$NCOR$^{16}$R$^{17}$ substituent together with the nitrogen to which they are attached form a 5-or 6-membered lactam ring, v is 1, or a pharmaceutically acceptable salt thereof or optical isomer of said compound or salt thereof.

27. A compound according to claim 26 that is 3-[2-(4-Methyl-piperazin-1-yl)-benzyl]-1-[4-(2-oxo-pyrrolidin-1-ylmethyl)-phenyl]-piperidin-2-one, or a pharmaceutically acceptable salt thereof or optical isomer of said compound or salt thereof.

28. A compound according to claim 1 wherein a lactone is formed from said —CH$_2$OH substituent, with said ortho —COOH substituent, or a pharmaceutically acceptable salt thereof or optical isomer of said compound or salt thereof.

29. A compound according to claim 28 that 3-[2-(4-Methyl-piperazin-1-yl)-benzyl]-1-(3-oxo-1,3-dihydro-isobenzofuran-5-yl)-piperidin-2-one, or a pharmaceutically acceptable salt thereof or optical isomer of said compound or salt thereof.

30. A compound according to claim 1 wherein R$^6$ is selected from hydrogen, methyl, ethyl and benzyl, R$^{13}$ is methyl, X is fluoro, methyl, or methoxy, a is 1 or 2, m is 1 or 2, n is 1 or 2, or a pharmaceutically acceptable salt thereof or optical isomer of said compound or salt thereof.

31. A compound according to claim 1 selected from the group consisting of
(R)-3-[5-Fluoro-2-(4-methyl-piperazin-1-yl)-benzyl]-1-[4-(1-hydroxy-1-methyl-ethyl)-phenyl]-pyrrolidin-2-one,
(R)-3-[2-(4-Methyl-piperazin-1-yl)-benzyl]-1-(6-morpholin-4-yl-pyridin-3-yl)-pyrrolidin-2-one,
(R)-1-[4-(1-Hydroxy-1-methyl-ethyl)-phenyl]-3-[2-(4-methyl-piperazin-1-yl)-benzyl]-pyrrolidin-2-one,
(R)-3-[2-(4-Methyl-piperazin-1-yl)-benzyl]-1-(4-morpholin-4-yl-phenyl)-pyrrolidin-2-one,
(R)-1-[4-(1-Hydroxy-cyclopentyl)-phenyl]-3-[2-(4-methyl-piperazin-1-yl)-benzyl]-pyrrolidin-2-one,
(R)-1-[4-(1-Hydroxy-cyclohexyl)-phenyl]-3-[2-(4-methyl-piperazin-1-yl)-benzyl]-pyrrolidin-2-one,
(R)-1-[4-(1-Ethyl-1-hydroxy-propyl)-phenyl]-3-[2-(4-methyl-piperazin-1-yl)-benzyl]-pyrrolidin-2-one,
(R)-1-[3-(1-Hydroxy-1-methyl-ethyl)-phenyl]-3-[2-(4-methyl-piperazin-1-yl)-benzyl]-pyrrolidin-2-one,
(R)-1-[4-(2-Hydroxy-2-methyl-propyl)-phenyl]-3-[2-(4-methyl-piperazin-1-yl)-benzyl]-pyrrolidin-2-one,
(R)-1-[6-(1-Hydroxy-1-methyl-ethyl)-pyridin-3-yl]-3-[2-(4-methyl-piperazin-1-yl)-benzyl]-pyrrolidin-2-one,
(R)-3-[5-fluoro-2-(4-methylpiperazin-1-yl)benzyl]-1-[4-(1-hydroxycyclopentyl)phenyl]pyrrolidin-2-one,
(R)-1-[4-(1-hydroxycyclopentyl)phenyl]-3-[2-(4-methylpiperazin-1-yl)benzyl]piperidin-2-one,
(R)-1-[4-(1-hydroxy-1-methylethyl)phenyl]-3-[2-(4-methylpiperazin-1-yl)benzyl]piperidin-2-one,
(R)-1-[4-(4-hydroxytetrahydro-2H-pyran-4-yl)phenyl]-3-[2-(4-methylpiperazin-1-yl)benzyl]piperidin-2-one,
(R)-1-[6-(1-hydroxy-1-methylethyl)pyridin-3-yl]-3-[2-(4-methylpiperazin-1-yl)benzyl]piperidin-2-one,
(R)-3-[5-fluoro-2-(4-methylpiperazin-1-yl)benzyl]-1-[6-(1-hydroxy-1-methylethyl)pyridin-3-yl]pyrrolidin-2-one,
(R)-3-[2-fluoro-6-(4-methylpiperazin-1-yl)benzyl]-1-[6-(1-hydroxy-1-methylethyl)pyridin-3-yl]pyrrolidin-2-one,
(R)-1-[6-(1-hydroxy-1-methylethyl)pyridin-3-yl]-3-{2-[(3R,5S)-3,4,5-trimethylpiperazin-1-yl]benzyl}pyrrolidin-2-one,
(R)-3-[5-fluoro-2-(4-methylpiperazin-1-yl)benzyl]-1-[6-(1-hydroxy-1-methylethyl)pyridin-3-yl]piperidin-2-one,
(R)-1-[6-(1-Ethyl-1-hydroxy-propyl)-pyridin-3-yl]-3-[2-(4-methyl-piperazin-1-yl)-benzyl]-pyrrolidin-2-one,
(R)-1-[4-(1-Hydroxy-cyclobutyl)-phenyl]-3-[2-(4-methyl-piperazin-1-yl)-benzyl]-pyrrolidin-2-one,
(R)-3-[2-(4-methylpiperazin-1-yl)benzyl]-1-[4-(piperidin-1-ylcarbonyl)phenyl]pyrrolidin-2-one, or a pharmaceutically acceptable salt thereof.

32. A compound according to claim 31 selected from the group consisting of
(R)-1-[4-(1-Hydroxy-1-methyl-ethyl)-phenyl]-3-[2-(4-methyl-piperazin-1-yl)-benzyl]-pyrrolidin-2-one,
(R)-1-[4-(1-Hydroxy-cyclopentyl)-phenyl]-3-[2-(4-methyl-piperazin-1-yl)-benzyl]-pyrrolidin-2-one,
(R)-1-[4-(1-Ethyl-1-hydroxy-propyl)-phenyl]-3-[2-(4-methyl-piperazin-1-yl)-benzyl]-pyrrolidin-2-one,
(R)-1-[4-(2-Hydroxy-2-methyl-propyl)-phenyl]-3-[2-(4-methyl-piperazin-1-yl)-benzyl]-pyrrolidin-2-one,
(R)-1-[6-(1-Hydroxy-1-methyl-ethyl)-pyridin-3-yl]-3-[2-(4-methyl-piperazin-1-yl)-benzyl]-pyrrolidin-2-one,
(R)-1-[4-(1-hydroxy-1-methylethyl)phenyl]-3-[2-(4-methylpiperazin-1-yl)benzyl]piperidin-2-one,
(R)-1-[6-(1-hydroxy-1-methylethyl)pyridin-3-yl]-3-[2-(4-methylpiperazin-1-yl)benzyl]piperidin-2-one,
(R)-3-[5-fluoro-2-(4-methylpiperazin-1-yl)benzyl]-1-[6-(1-hydroxy-1-methylethyl)pyridin-3-yl]pyrrolidin-2-one,
(R)-3-[2-fluoro-6-(4-methylpiperazin-1-yl)benzyl]-1-[6-(1-hydroxy-1-methylethyl)pyridin-3-yl]pyrrolidin-2-one,
(R)-1-[6-(1-hydroxy-1-methylethyl)pyridin-3-yl]-3-{2-[(3R,5S)-3,4,5-trimethylpiperazin-1-yl]benzyl}pyrrolidin-2-one,
(R)-1-[6-(1-Ethyl-1-hydroxy-propyl)-pyridin-3-yl]-3-[2-(4-methyl-piperazin-1-yl)-benzyl]-pyrrolidin-2-one,
(R)-1-[4-(1-Hydroxy-cyclobutyl)-phenyl]-3-[2-(4-methyl-piperazin-1-yl)-benzyl]-pyrrolidin-2-one, or a pharmaceutically acceptable salt thereof.

33. A compound according to claim 31 that is (R)-1-[4-(1-Hydroxy-1-methyl-ethyl)-phenyl]-3-[2-(4-methyl-piperazin-1-yl)-benzyl]-pyrrolidin-2-one, or a pharmaceutically acceptable salt thereof.

34. A compound according to claim 31 that is (R)-1-[4-(1-Ethyl-1-hydroxy-propyl)-phenyl]-3-[2-(4-methyl-piperazin-1-yl)-benzyl]-pyrrolidin-2-one, or a pharmaceutically acceptable salt thereof.

35. A compound according to claim 31 that is (R)-1-[4-(2-Hydroxy-2-methyl-propyl)-phenyl]-3-[2-(4-methyl-piperazin-1-yl)-benzyl]-pyrrolidin-2-one, or a pharmaceutically acceptable salt thereof.

36. A compound according to claim 31 that is (R)-1-[6-(1-Hydroxy-1-methyl-ethyl)-pyridin-3-yl]-3-[2-(4-methyl-piperazin-1-yl)-benzyl]-pyrrolidin-2-one, or a pharmaceutically acceptable salt thereof.

37. A compound according to claim 31 that is (R)-3-[5-Fluoro-2-(4-methyl-piperazin-1-yl)-benzyl]-1-[6-(1-hydroxy-1-methyl-ethyl)-pyridin-3-yl]-pyrrolidin-2-one, or a pharmaceutically acceptable salt thereof.

38. A compound according to claim 31 that is (R)-3-[2-Fluoro-6-(4-methyl-piperazin-1-yl)-benzyl]-1-[6-(1-hydroxy-1-methyl-ethyl)-pyridin-3-yl]-pyrrolidin-2-one, or a pharmaceutically acceptable salt thereof.

39. A compound according to claim 31 that is (R)-1-[6-(1-Hydroxy-1-methyl-ethyl)-pyridin-3-yl]-3-[2-(3  ,4,5-trimethyl-piperazin-1-yl)-benzyl]-pyrrolidin-2-one, or a pharmaceutically acceptable salt thereof.

40. A compound according to claim 31 that is (R)-1-[6-(1-Ethyl-1-hydroxy-propyl)-pyridin-3-yl]-3-[2-(4-methyl-piperazin-1-yl)-benzyl]-pyrrolidin-2-one, or a pharmaceutically acceptable salt thereof.

41. A compound according to claim 1 selected from the group consisting of
- (S)-3-[5-Fluoro-2-(4-methyl-piperazin-1-yl)-benzyl]-1-[4-(1-hydroxy-1-methyl-ethyl)-phenyl]-pyrrolidin-2-one,
- (S)-3-[2-(4-Methyl-piperazin-1-yl)-benzyl]-1-(6-morpholin-4-yl-pyridin-3-yl)-pyrrolidin-2-one,
- (S)-1-[4-(1-Hydroxy-1-methyl-ethyl)-phenyl]-3-[2-(4-methyl-piperazin-1-yl)-benzyl]-pyrrolidin-2-one,
- (S)-3-[2-(4-Methyl-piperazin-1-yl)-benzyl]-1-(4-morpholin-4-yl-phenyl)-pyrrolidin-2-one,
- (S)-1-[4-(1-Hydroxy-cyclopentyl)-phenyl]-3-[2-(4-methyl-piperazin-1-yl)-benzyl]-pyrrolidin-2-one,
- (S)-1-[4-(1-Hydroxy-cyclohexyl)-phenyl]-3-[2-(4-methyl-piperazin-1-yl)-benzyl]-pyrrolidin-2-one,
- (S)-1-[4-(1-Ethyl-1-hydroxy-propyl)-phenyl]-3-[2-(4-methyl-piperazin-1-yl)-benzyl]-pyrrolidin-2-one,
- (S)-1-[3-(1-Hydroxy-1-methyl-ethyl)-phenyl]-3-[2-(4-methyl-piperazin-1-yl)-benzyl]-pyrrolidin-2-one,
- (S)-1-[4-(2-Hydroxy-2-methyl-propyl)-phenyl]-3-[2-(4-methyl-piperazin-1-yl)-benzyl]-pyrrolidin-2-one,
- (S)-1-[6-(1-Hydroxy-1-methyl-ethyl)-pyridin-3-yl]-3-[2-(4-methyl-piperazin-1-yl)-benzyl]-pyrrolidin-2-one,
- (S)-3-[5-fluoro-2-(4-methylpiperazin-1-yl)benzyl]-1-[4-(1-hydroxycyclopentyl)phenyl]pyrrolidin-2-one,
- (S)-1-[4-(1-hydroxycyclopentyl)phenyl]-3-[2-(4-methylpiperazin-1-yl)benzyl]piperidin-2-one,
- (S)-1-[4-(1-hydroxy-1-methylethyl)phenyl]-3-[2-(4-methylpiperazin-1-yl)benzyl]piperidin-2-one,
- (S)-1-[4-(4-hydroxytetrahydro-2H-pyran-4-yl)phenyl]-3-[2-(4-methylpiperazin-1-yl)benzyl]piperidin-2-one,
- (S)-1-[6-(1-hydroxy-1-methylethyl)pyridin-3-yl]-3-[2-(4-methylpiperazin-1-yl)benzyl]piperidin-2-one,
- (S)-3-[5-fluoro-2-(4-methylpiperazin-1-yl)benzyl]-1-[6-(1-hydroxy-1-methylethyl)pyridin-3-yl]pyrrolidin-2-one,
- (S)-3-[2-fluoro-6-(4-methylpiperazin-1-yl)benzyl]-1-[6-(1-hydroxy-1-methylethyl)pyridin-3-yl]pyrrolidin-2-one,
- (S)-1-[6-(1-hydroxy-1-methylethyl)pyridin-3-yl]-3-{2-[(3R,5S)-3,4,5-trimethylpiperazin-1-yl]benzyl}pyrrolidin-2-one,
- (S)-3-[5-fluoro-2-(4-methylpiperazin-1-yl)benzyl]-1-[6-(1-hydroxy-1-methylethyl)pyridin-3-yl]piperidin-2-one,
- (S)-1-[6-(1-Ethyl-1-hydroxy-propyl)-pyridin-3-yl]-3-[2-(4-methyl-piperazin-1-yl)-benzyl]-pyrrolidin-2-one,
- (S)-1-[4-(1-Hydroxy-cyclobutyl)-phenyl]-3-[2-(4-methyl-piperazin-1-yl)-benzyl]-pyrrolidin-2-one,
- (S)-3-[2-(4-methylpiperazin-1-yl)benzyl]-1-[4-(piperidin-1-ylcarbonyl)phenyl]pyrrolidin-2-one, or a pharmaceutically acceptable salt thereof.

42. A compound according to claim 41 (S)-4 that is (S)-1-[4-(1-Hydroxy-1-methyl-ethyl)-phenyl]-3-[2-(4-methyl-piperazin-1-yl)-benzyl]-pyrrolidin-2-one, or a pharmaceutically acceptable salt thereof.

43. A compound according to claim 41 that is (S)-1-[4-(1-Ethyl-1-hydroxy-propyl)-phenyl]-3-[2-(4-methyl-piperazin-1-yl)-benzyl]-pyrrolidin-2-one, or a pharmaceutically acceptable salt thereof.

44. A compound according to claim 41 that is (S)-1-[4-(2-Hydroxy-2-methyl-propyl)-phenyl]-3-[2-(4-methyl-piperazin-1-yl)-benzyl]-pyrrolidin-2-one, or a pharmaceutically acceptable salt thereof.

45. A compound according to claim 41 that is (S)-1-[6-(1-Hydroxy-1-methyl-ethyl)-pyridin-3-yl]-3-[2-(4-methyl-piperazin-1-yl)-benzyl]-pyrrolidin-2-one, or a pharmaceutically acceptable salt thereof.

46. A compound according to claim 41 that is (S)-3-[5-Fluoro-2-(4-methyl-piperazin-1-yl)-benzyl]-1-[6-(1-hydroxy-1-methyl-ethyl)-pyridin-3-yl]-pyrrolidin-2-one, or a pharmaceutically acceptable salt thereof.

47. A compound according to claim 41 that is (S)-3-[2-Fluoro-6-(4-methyl-piperazin-1-yl)-benzyl]-1-[6-(1-hydroxy-1-methyl-ethyl)-pyridin-3-yl]-pyrrolidin-2-one, or a pharmaceutically acceptable salt thereof.

48. A compound according to claim 41 that is (S)-1-[6-(1-Hydroxy-1-methyl-ethyl)-pyridin-3-yl]-3-[2-(3  ,4,5-trimethyl-piperazin-1-yl)-benzyl]-pyrrolidin-2-one, or a pharmaceutically acceptable salt thereof.

49. A compound according to claim 41 that is (S)-1-[6-(1-Ethyl-1-hydroxy-propyl)-pyridin-3-yl]-3-[2-(4-methyl-piperazin-1-yl)-benzyl]-pyrrolidin-2-one, or a pharmaceutically acceptable salt thereof.

50. A method of preparing a compound having the formula 1A':

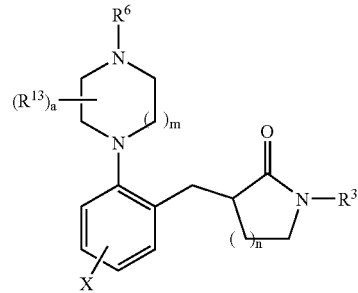

or a pharmaceutically acceptable salt thereof
wherein a is zero to eight;
m is one;
$R^6$ is selected from the group consisting of hydrogen, $(C_1-C_6)$alkyl optionally substituted with $(C_1-C_6)$alkoxy or one to three fluorine atoms, or $((C_1-C_4)$alkyl)aryl wherein the aryl moiety is phenyl, naphthyl, or heteroaryl-$(CH_2)q$-, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, cyano and —$SO_t(C_1-C_6)$alkyl, wherein t is zero, one or two;

each $R^{13}$ is, independently, $(C_1-C_4)$alkyl;

X is hydrogen, chloro, fluoro, bromo, iodo, cyano, $(C_1-C_6)$alkyl, hydroxy, $(C_1-C_6)$alkoxy, —$SO_t(C_1-C_6)$alkyl wherein t is zero, one or two, —$CO_2R^{10}$ or —$CONR^{11}R^{12}$, each of $R^{10}$, $R^{11}$ and $R^{12}$ is selected, independently, from hydrogen, $(C_1-C_4)$alkyl, phenyl and naphthyl, wherein said phenyl or naphthyl may optionally be substituted with one or more substituents independently selected from chloro, fluoro, bromo, iodo, $(C_1-C_6)$alkyl, $(C_1-C_6)$alkoxy, trifluoromethyl, cyano and —$SO_t(C_1-C_6)$alkyl wherein t is zero to two; or $R^{11}$ and $R^{12}$, together with the nitrogen to which they are attached, form a 4 to 7-membered heteroalkyl ring that may contain from zero to four heteroatoms selected from nitrogen, sulfur and oxygen;

$R^3$ is phenyl or pyridyl substituted with one to three substituents independently selected from $(C_1-C_8)$hydroxyalkyl-, $(C_1-C_8)$alkoxy-$(C_1-C_8)$alkyl-, $(C_3-C_8)$hydroxycycloalkyl-, $(C_3-C_8)$cycloalkoxy-, $(C_1-C_8)$alkoxy-$(C_3-C_8)$cycloalkyl-, heterocycloalkyl, hydroxyheterocycloalkyl, and $(C_1-C_8)$alkoxy-heterocycloalkyl, wherein each $(C_3-C_8)$cycloalkyl or heterocycloalkyl moiety may be independently substituted with from one to three $(C_1-C_6)$alkyl or benzyl groups; or substituted with one to three substituents independently selected from phenyl, naphthyl and a 5- to 6-membered heteroaryl ring containing from one to four heteroatoms selected from oxygen, nitrogen and sulfur, with the proviso that said heteroaryl ring cannot contain two adjacent oxygen atoms or two adjacent sulfur atoms, and wherein each independently selected phenyl, naphthyl or heteroaryl substituent may itself be substituted with from one to three $(C_1-C_8)$alkyl or $C_3-C_8$ cycloalkyl substituents; or substituted with one to three substituents independently selected from (a) lactone formed from —$CH_2)_tOH$ with an ortho —COOH, wherein t is one, two or three; (b) —$CONR^{14}R^{15}$ wherein $R^{14}$ and $R^{15}$ are independently selected from $(C_1-C_8)$alkyl and benzyl, or $R^{14}$ and $R^{15}$ together with the nitrogen to which they are attached form a 5- to 7-membered heteroalkyl ring that may contain from zero to three heteroatoms selected from nitrogen, sulfur and oxygen in addition to the nitrogen of the —$CONR^{14}R^{15}$ group, wherein when any of said heteroatoms is nitrogen it may be optionally substituted with $(C_1-C_8)$alkyl or benzyl, with the proviso that said ring cannot contain two adjacent oxygen atoms or two adjacent sulfur atoms; (c) —$(CH_2)_v$ $NCOR^{16}R^{17}$ wherein v is zero, one, two or three and —$COR^{16}$ and $R^{17}$ taken together with the nitrogen to which they are attached form a 4- to 6-membered lactam ring; and, (d) —$(C_1-C_8)NR^{18}R^{19}$ where each of $R^{18}$ and $R^{19}$ is selected, independently, from hydrogen and $(C_1-C_4)$alkyl, or $R^{18}$ and $R^{19}$, together with the nitrogen to which they are attached, form a 4- to 7-membered heteroalkyl ring that may contain from zero to four heteroatoms selected from nitrogen, sulfur and oxygen;

wherein the broken lines indicate optional double bonds; and, n is one, two, or three; or, a pharmaceutically acceptable salt or optical isomer thereof which comprises (a) preparing a compound having the formula 1B':

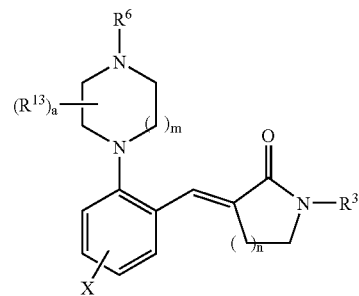

and either (b) treating the compound prepared in step (a) with hydrogen gas in a reaction-inert solvent selected from the group consisting of a lower alcohol, THF, dioxane, ethyl acetate, methanol and ethanol, in the presence of a noble metal catalyst on a solid support selected from the group consisting of palladium on carbon (Pd/C), palladium on barium sulfate (Pd/BaSO$_4$), platinum on carbon (Pt/C), tris (triphenylphosphine) rhodium chloride (Wilkinson's catalyst), and 1000 palladium on carbon, at a pressure of from about 1 to about 5 atmospheres, preferably about 3 to about 4 atmospheres, at a temperature of about 10° C. to about 100° C., under conditions suitable to form the compound having the formula 1A; or, (b') treating the compound prepared in step (a) under transfer hydrogenation conditions with a hydride donor selected from the group consisting of cyclohexadiene and ammonium formate, in a reaction-inert solvent selected from a lower alcohol, THF, dioxane, ethyl acetate, methanol and ethanol, in the presence of a noble metal catalyst on a solid support selected from the group consisting of palladium on carbon (Pd/C), palladium on barium sulfate (Pd/BaSO$_4$), platinum on carbon (Pt/C), tris(triphenylphosphine) rhodium chloride (Wilkinson's catalyst), and 10% palladium on carbon, at a temperature of about 20° C. to about 150° C., under conditions suitable to form the compound having the formula 1A, optionally preparing a pharmaceutically acceptable salt thereof.

51. A method of preparing a compound having formula 1B':

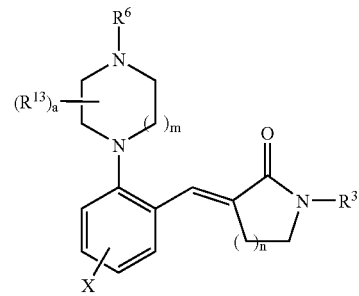

wherein a is zero to eight;

m is one;

$R^6$ is selected from the group consisting of hydrogen, $(C_1-C_6)$alkyl optionally substituted with $(C_1-C_6)$alkoxy or one to three fluorine atoms, or $((C_1-C_4)$alkyl)aryl wherein the aryl moiety is phenyl, naphthyl, or heteroaryl-$(CH_2)_q$-, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, cyano and —$SO_t(C_1-C_6)$alkyl, wherein t is zero, one or two;

each $R^{13}$ is, independently, $(C_1-C_4)$alkyl;

X is hydrogen, chloro, fluoro, bromo, iodo, cyano, $(C_1-C_6)$ alkyl, hydroxy, $(C_1-C_6)$alkoxy, —$SO_t(C_1-C_6)$alkyl wherein t is zero, one or two, —$CO_2R^{10}$ or —$CONR^{11}R^{12}$; each of $R^{10}$, $R^{11}$ and $R^{12}$ is selected, independently, from hydrogen, $(C_1-C_4)$alkyl, phenyl and naphthyl, wherein said phenyl or naphthyl may optionally be substituted with one or more substituents independently selected from chloro, fluoro, bromo, iodo, $(C_1-C_6)$alkyl, $(C_1-C_6)$alkoxy, trifluoromethyl, cyano and —$SO_t(C_1-C_6)$alkyl wherein t is zero to two; or $R^{11}$ and $R^{12}$, together with the nitrogen to which they are attached, form a 4 to 7-membered heteroalkyl ring that may contain from zero to four heteroatoms selected from nitrogen, sulfur and oxygen;

$R^3$ is phenyl or pyridyl substituted with one to three substituents independently selected from $(C_1-C_8)$hydroxyalkyl-, $(C_1-C_8)$alkoxy-$(C_1-C_8)$alkyl-, $(C_3-C_8)$hydroxycycloalkyl-, $(C_3-C_8)$cycloalkoxy-, $(C_1-C_8)(C^3-C_8)$ cycloalkyl-, heterocycloalkyl, hydroxyheterocycloalkyl, and $(C_1-C_8)$alkoxy-heterocycloalkyl, wherein each $(C_3-C_8)$cycloalkyl or heterocycloalkyl moiety may be independently substituted with from one to three $(C_1-C_6)$alkyl or benzyl groups; or substituted with one to three substituents independently selected from phenyl, naphthyl and a 5- to 6-membered heteroaryl ring containing from one to four heteroatoms selected from oxygen, nitrogen and sulfur, with the proviso that said heteroaryl ring cannot contain two adjacent oxygen atoms or two adjacent sulfur atoms, and wherein each independently selected phenyl, naphthyl or heteroaryl substituent may itself be substituted with from one to three $(C_1-C_8)$alkyl or $C_3-C_8$ cycloalkyl substituents; or substituted with one to three substituents independently selected from (a) lactone formed from —$CH_3)_tOH$ with an ortho —COOH, wherein t is one, two or three; (b) —$CONR^{14}R^{15}$ wherein $R^{14}$ and $R^{15}$ are independently selected from $(C_1-C_8)$alkyl and benzyl, or $R^{14}$ and $R^{15}$ together with the nitrogen to which they are attached form a 5- to 7-membered heteroalkyl ring that may contain from zero to three heteroatoms selected from nitrogen, sulfur and oxygen in addition to the nitrogen of the —$CONR^{14}R^{15}$ group, wherein when any of said heteroatoms is nitrogen it may be optionally substituted with $(C_1-C_8)$alkyl or benzyl, with the proviso that said ring cannot contain two adjacent oxygen atoms or two adjacent sulfur atoms; (c) —$(CH_2)_vNCOR^{16}R^{17}$ wherein v is zero, one, two or three and —$COR^{16}$ and $R^{17}$ taken together with the nitrogen to which they are attached form a 4- to 6-membered lactam ring; and, (d) —$C_1-C_8)NR^{18}R^{19}$ where each of $R^{18}$ and $R^{19}$ is selected, independently, from hydrogen and $(C_1-C_4)$ alkyl, or $R^{18}$ and $R^{19}$, together with the nitrogen to which they are attached, form a 4- to 7-membered heteroalkyl ring that may contain from zero to four heteroatoms selected from nitrogen, sulfur and oxygen;

wherein the broken lines indicate optional double bonds; and, n is one, two, or three; or, a pharmaceutically acceptable salt or optical isomer thereof which comprises (a) preparing a compound having the formula 1B:

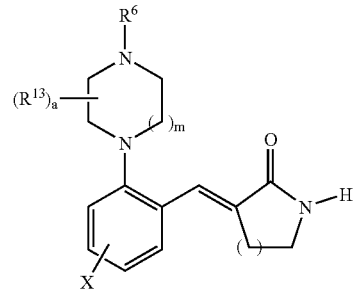

and treating the compound prepared in step (a) with a reagent $R^3$-Y, wherein $R^3$ is as defined above and Y is chloro, bromo, fluoro, iodo or sulfonate, in a suitable reaction inert solvent selected from the group consisting of 1,2-dimethoxyethane, diglyme, t-butyl methyl ether, tetrahydrofuran, benzene and toluene, in the presence of (1) a base selected from the group consisting of potassium phosphate, potassium carbonate, sodium carbonate, thallium carbonate, cesium carbonate, potassium tert-butoxide, lithium tert-butoxide, or sodium tert-butoxide, a diamine, 1,2-ethylenediamine, N,N'-dimethylethylenediamine, N,N-dimethylethylenediamine, and cis-1,2-diaminocyclohexane, (2) a copper(I) salt selected from the group consisting of cuprous chloride, cuprous bromide and cuprous iodide, and (3) an amount of water comprising from about 10% to about 4% w/w, optionally in the presence of a polar co-solvent selected from the group consisting of N,N-dimethyl formamide and N,N-dimethyl acetamide in the order of 5-15% v/v relative to the first solvent, at a temperature from about 40° C. to about 150° C., under suitable conditions to form the compound having formula 1B".

52. A method of preparing a compound having formula 1A':

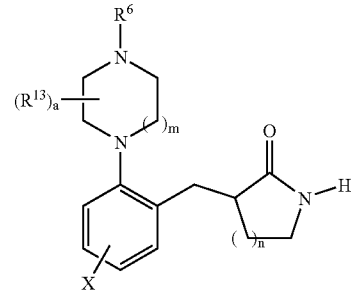

or a pharmaceutically acceptable salt thereof;
wherein a is zero to eight;
m is one;
$R^6$ is selected from the group consisting of hydrogen, $(C_1-C_6)$alkyl optionally substituted with $(C_1-C_6)$alkoxy or one to three fluorine atoms, or $((C_1-C_4)$alkyl)aryl wherein the aryl moiety is phenyl, naphthyl, or heteroaryl-$(CH_2)$q-, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, cyano and —SO$_t$(C$_1$-C$_6$)alkyl, wherein t is zero, one or two;

each $R^{13}$ is, independently, $(C_1-C_4)$alkyl;

X is hydrogen, chloro, fluoro, bromo, iodo, cyano, $(C_1-C_6)$ alkyl, hydroxy, $(C_1-C_6)$alkoxy, —SO$_t$(C$_1$-C$_6$)alkyl wherein t is zero, one or two, —CO$_2$R$^{10}$ or —CONR$^{11}$R$^{12}$; each of R$^{10}$, R$^{11}$ and R$^{12}$ is selected, independently, from hydrogen, $(C_1-C_4)$alkyl, phenyl and naphthyl, wherein said phenyl or naphthyl may optionally be substituted with one or more substituents independently selected from chloro, fluoro, bromo, iodo, $(C_1-C_6)$alkyl, $(C_1-C_6)$alkoxy, trifluoromethyl, cyano and —SO$_t$(C$_1$-C$_6$)alkyl wherein t is zero to two; or R$^{11}$ and R$^{12}$, together with the nitrogen to which they are attached, form a 4 to 7-membered heteroalkyl ring that may contain from zero to four heteroatoms selected from nitrogen, sulfur and oxygen;

R$^1$ is phenyl or pyridyl substituted with one to three substituents independently selected from $(C_1-C_8)$hydroxyalkyl-, $(C_1-C_8)$alkoxy-$(C_1-C_8)$alkyl-, $(C_3-C_8)$hydroxycycloalkyl-, $(C_3-C_8)$cycloalkoxy-, $(C_1-C_8)$alkoxy-$(C_3-C_8)$cycloalkyl-, heterocycloalkyl-, hydroxyheterocycloalkyl, and $(C_1-C_8)$alkoxy-heterocycloalkyl, wherein each $(C_3-C_8)$cycloalkyl or heterocycloalkyl moiety may be independently substituted with from one to three $(C_1-C_6)$alkyl or benzyl groups; or substituted with one to three substituents independently selected from phenyl, naphthyl and a 5- to 6-membered heteroaryl ring containing from one to four heteroatoms selected from oxygen, nitrogen and sulfur, with the proviso that said heteroaryl ring cannot contain two adjacent oxygen atoms or two adjacent sulfur atoms, and wherein each independently selected phenyl, naphthyl or heteroaryl substituent may itself be substituted with from one to three $(C_1-C_8)$alkyl or C$_3$-C$_8$ cycloalkyl substituents; or substituted with one to three substituents independently selected from (a) lactone formed from —(CH$_2$)$_t$OH with an ortho —COOH, wherein t is one, two or three; (b) —CONR$^{14}$R$^{15}$, wherein R$^{14}$ and R$^{15}$ are independently selected from $(C_1-C_8)$alkyl and benzyl, or R$^{14}$ and R$^{15}$ together with the nitrogen to which they are attached form a 5- to 7-membered heteroalkyl ring that may contain from zero to three heteroatoms selected from nitrogen, sulfur and oxygen in addition to the nitrogen of the —CONR$^{14}$R$^{15}$ group, wherein when any of said heteroatoms is nitrogen it may be optionally substituted with $(C_1-C_8)$alkyl or benzyl, with the proviso that said ring cannot contain two adjacent oxygen atoms or two adjacent sulfur atoms; (c) —(CH$_2$)$_v$NCOR$^{16}$ R$^{17}$ wherein v is zero, one two or three and —COR$^{16}$ and R$^{17}$ taken together with the nitrogen to which they are attached form a 4- to 6-membered lactam ring; and, (d) —(C$_1$-C$_8$)NR$^{18}$R$^{19}$, where each of R$^{18}$ and R$^{19}$ is selected, independently, from hydrogen and $(C_1-C_4)$ alkyl, or R$^{18}$ and R$^{19}$, together with the nitrogen to which they are attached, form a 4- to 7-membered heteroalkyl ring that may contain from zero to four heteroatoms selected from nitrogen, sulfur and oxygen;

wherein the broken lines indicate optional double bonds; and, n is one, two, or three; or, a pharmaceutically acceptable salt or optical isomer thereof; which comprises (a) preparing a compound having the formula 1A:

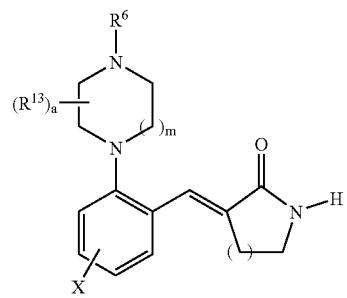

and treating the compound prepared in step (a) with a reagent R$^3$-Y, wherein R$^3$ is as defined above and Y is chloro, bromo, fluoro, iodo or sulfonate, in a suitable reaction inert solvent selected from the group consisting of 1,2-dimethoxyethane, diglyme, t-butyl methyl ether, tetrahydrofuran, benzene and toluene, in the presence of (1) a base selected from the group consisting of potassium phosphate, potassium carbonate, sodium carbonate, thallium carbonate, cesium carbonate, potassium tert-butoxide, lithium tert-butoxide, or sodium tert-butoxide, a diamine, 1,2-ethylenediamine, N,N'-dimethylethylenediamine, N,N-dimethylethylenediamine, and cis-1,2-diaminocyclohexane, (2) a copper(I) salt selected from the group consisting of cuprous chloride, cuprous bromide and cuprous iodide, and (3) an amount of water comprising from about 1% to about 4% w/w, optionally in the presence of a polar co-solvent selected from the group consisting of N,N-dimethyl formamide and N,N-dimethyl acetamide in the order of 5-15% v/v relative to the first solvent, at a temperature from about 40° C. to about 150° C., under suitable conditions to form the compound having formula 1A', optionally preparing a pharmaceutically acceptable salt thereof.

* * * * *

UNITED STATES PATENT AND TRADEMARK OFFICE
CERTIFICATE OF CORRECTION

PATENT NO. : 7,479,559 B2
APPLICATION NO. : 11/083188
DATED : January 20, 2009
INVENTOR(S) : Michael A. Brodney et al.

Page 1 of 2

It is certified that error appears in the above-identified patent and that said Letters Patent is hereby corrected as shown below:

Title Page:

Item (57) In the abstract, the formula $G^2$ should be deleted.

In the Claims:

Column 57, lines 26-39, claim 1, the formula I should be replaced by:

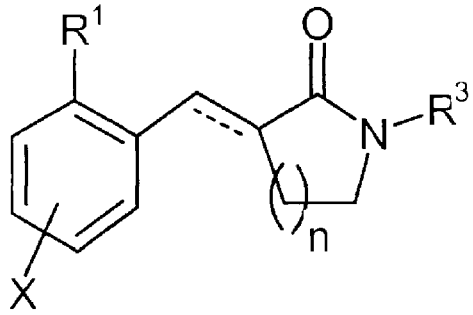

I

Column 57, lines 42-55, formula $G^1$ should be replaced by:

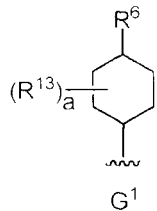

$G^1$

Column 57, line 58, the substitute "$R^1$" should read --$R^6$--.

Signed and Sealed this
Twenty-eighth Day of May, 2013

Teresa Stanek Rea
*Acting Director of the United States Patent and Trademark Office*

Column 58, line 3, the formula reading "-S01(C$_1$-C$_6$)alkyl" should read --SO$_1$(C$_1$-C$_6$)alkyl--; line 5, the formula reading "(C$_1$-C$_4$)" should read --(C$_1$-C$_4$)alkyl--; and line 6, the formula reading "chioro" should be changed --chloro--.

Column 67, line 6, the formula reading "chioro" should be changed --chloro--.

Column 59, lines 46, the compound of --1-[4-(1-Hydroxy-1-methyl-ethyl)-phenyl]-3-[2-(4-methyl-[1,4]diazepan-1-yl)-benzyl]-pyrrolidin-2-one-- should be inserted here.

Column 62, lines 1-4, two compounds: "1-[4-(1-Hydroxy-cyclobutyl)-phenyl]-3-[2-(1-methyl-piperidin-4-yl)-benzyl]-pyrrolidin-2-one and 1-[4-(1-Hydroxy-cyclohexyl)-phenyl]-3-[2-(1-methyl-piperidin I yl)-benzyl]-pyffolidin-2-one" should be deleted.